United States Patent
Barth et al.

(10) Patent No.: US 7,538,111 B2
(45) Date of Patent: May 26, 2009

(54) BENZENESULPHONAMIDE DERIVATIVES, METHOD FOR PRODUCTION AND USE THEREOF FOR TREATMENT OF PAIN

(75) Inventors: Martine Barth, Asnieres-les-Dijon (FR); Michel Bondoux, Fontaine-les-Dijon (FR); Pierre Dodey, Fontaine-les-Dijon (FR); Christine Massardier, Dijon (FR); Didier Thomas, Saint-Apollinaire (FR); Jean-Michel Luccarini, Dijon (FR)

(73) Assignee: Laboratoires Fournier S.A., Dijon (FR)

( * ) Notice: Subject to any disclaimer, the term of this patent is extended or adjusted under 35 U.S.C. 154(b) by 15 days.

(21) Appl. No.: 10/549,546

(22) PCT Filed: Mar. 24, 2004

(86) PCT No.: PCT/FR2004/000723

§ 371 (c)(1),
(2), (4) Date: Sep. 14, 2005

(87) PCT Pub. No.: WO2004/087700

PCT Pub. Date: Oct. 14, 2004

(65) Prior Publication Data

US 2006/0178360 A1    Aug. 10, 2006

(30) Foreign Application Priority Data

Mar. 25, 2003 (FR) ................................ 03 03602
Apr. 11, 2003 (FR) ................................ 03 04530

(51) Int. Cl.
*A01N 43/58* (2006.01)
*A01N 43/60* (2006.01)
*A61K 31/50* (2006.01)
*A61K 31/495* (2006.01)

(52) U.S. Cl. .................. 514/250; 544/392; 544/359
(58) Field of Classification Search ................ 514/250
See application file for complete search history.

(56) References Cited

U.S. PATENT DOCUMENTS

| 4,791,102 A | 12/1988 | Bernat et al. |
| 4,977,168 A | 12/1990 | Bernat et al. |
| 5,506,258 A | 4/1996 | Christophe et al. |

FOREIGN PATENT DOCUMENTS

| CA | 2091024 | 9/1993 |
| EP | 0 236 163 | 9/1987 |
| EP | 0 236 164 | 9/1987 |
| EP | 0 558 961 A2 | 9/1993 |
| EP | 0 614 911 A1 | 9/1994 |
| WO | WO 92/16549 | 10/1992 |
| WO | WO 9610022 | * 9/1995 |
| WO | WO 96/40639 | 12/1996 |
| WO | WO 97/09346 | 3/1997 |
| WO | 97/25315 | 7/1997 |
| WO | WO 97/24349 | 7/1997 |
| WO | WO 9807697 | * 7/1997 |
| WO | WO 98/03503 | 1/1998 |
| WO | 98/17655 | 4/1998 |
| WO | WO 98/24783 | 6/1998 |
| WO | WO 99/03387 | 1/1999 |
| WO | WO 01/05783 A1 | 1/2001 |
| WO | 01/30734 A1 | 5/2001 |
| WO | 02/053516 A2 | 7/2002 |
| WO | 02/089792 A1 | 11/2002 |
| WO | WO 02/099388 A2 | 12/2002 |

OTHER PUBLICATIONS

Etemad-Moghodam, et. al., European Journal of Medicinal Chemistry, (1988), 23, 577-85.*
Calheiros, et. al., Bioorganic & Medicinal Chemistry Letters (1995), 5(9), 937-40.*
Shibata et al., "Modified formalin test: characteristic biphasic pain response." *Pain* 38(1989): 347-352.
Wagner et al., "Synthese von Nα-(Tosyl-β-alanyl)-und Nα-(Tosyl-60-aminocapronyl) amidinophenylalaninamiden als stark wirksame Thrombininhibitoren," *Pharmazie* 39(1984): 315-317.
Wagner et al., "Synthese von Na-(Arylsulfonyl-L-prolyl)-und Na-Benzyloxycarbonyl-L-prolyl)-D,L-4-amidinophenyl-alaninamiden als Thrombininhibitoren[1]." *Pharmazie* 41(1986): 233-235.

* cited by examiner

*Primary Examiner*—James O. Wilson
*Assistant Examiner*—Jeffrey H Murray
(74) *Attorney, Agent, or Firm*—Merchant & Gould P.C.

(57) ABSTRACT

The present invention concerns novel benzenesulphonamide compounds, defined by formula I.

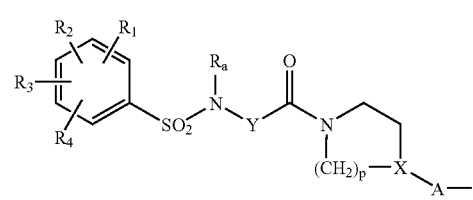

Therapeutic compositions comprising the benzenesulphonamide compounds of the invention or salts thereof and methods for producing the benzenesulphonamide compounds of the invention are also disclosed. The benzenesulphonamide compounds of the invention or salts thereof are useful for treating pain, such as hyperalgesia and major algesia.

8 Claims, No Drawings

BENZENESULPHONAMIDE DERIVATIVES, METHOD FOR PRODUCTION AND USE THEREOF FOR TREATMENT OF PAIN

The present invention concerns novel compounds of benzenesulphonamide type, their method of preparation and their use to obtain pharmaceutical compositions.

These novel compounds may be given therapeutic use, in particular to treat pain.

PRIOR ART

Compounds are already known whose structure includes a group of benzenesulphonamide type. For example, through EP 236 163 and EP 236 164, N-α-arylsulphonylaminoacyl-p-amidino-phenyl-alaninamide derivatives may be cited which are selective thrombin inhibitors and can be used as anti-thrombotics. Also, from EP 614 911, compounds are known having a fairly close structure to the preceding compounds, simultaneously containing an arylsulphamoyl group and a substituted phenylamidine group, which have the property of binding to receptors of the Y neuropeptide and can be used to treat hypertension, angina pectoris, atherosclerosis, depression, anxiety, inflammation, allergy or excess fat.

EP 558 961 also suggests the use of arylsulphonamide-type compounds of substituted amino acids for the treatment of thrombosis on account of their anticoagulant properties.

Studies on the anti-thrombotic properties of compounds containing an arylsulphonamide group in their structure and a phenylamidine group have also been published in Pharmazie 1984 vol. 39 (5) pages 315-317 and Pharmazie 1986 vol. 41 (4) p 233-235.

In the same field of pharmacological activity WO 92/16549 A1 describes derivatives of phenylalanine comprising an arylsulphonamide group, which are proteinase inhibitors, in particular thrombin inhibitors.

Also, according to WO 97/25315, compounds are known having N-(arylsulphonyl)amino-acid structure, which can be used to treat inflammatory diseases.

Among the prior art documents proposing structural elements of arylsulphonamide type, mention may be made of WO 96/40639, WO 97/24349, WO 98/03503, WO 98/24783 and WO 99/00387, pertaining to antagonist compounds of the B2 receptor of bradykinin. Antagonist compounds of the $B_1$ receptor of bradykinin, whether peptide or non-peptide, are also known through documents WO 01/05783, WO 02/099388 and WO 97/09346.

OBJECT OF THE INVENTION

The invention concerns novel compounds comprising the substituted benzenesulphonamide chain, said compounds being notably useful as active ingredients in medicinal products intended to treat pain, in particular hyperalgesia and major algesia.

DESCRIPTION

According to the present invention, as novel industrial product a compound is proposed of benzenesulphonamide type, characterized in that it is selected from the group consisting of:

a) compounds of formula:

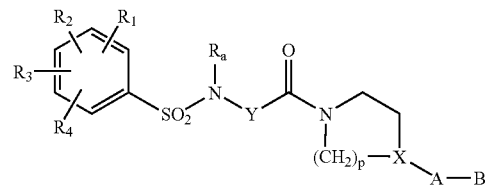

in which
$R_1$, $R_2$, $R_3$, $R_4$ each independently represent one or more atoms or groups of atoms selected from a hydrogen atom, halogens, $C_1$-$C_3$ alkyl groups, $C_1$-$C_3$ alkoxy groups, $CF_3$ or $OCF_3$ groups,
$R_a$ represents a $C_1$-$C_4$ alkyl group,
Y represents a saturated $C_2$-$C_5$ alkylene group, optionally interrupted by an oxygen atom, an unsaturated $C_2$-$C_4$ alkylene group, or a —$CH_2$—CO—NH—$CH_2$— group,
X represents CH or a nitrogen atom,
p represents 2 or 3,
A represents a single bond, a nitrogen atom optionally substituted with a methyl group, or a straight or branched $C_1$-$C_5$ alkylene group, optionally hydroxylated or of which one of the carbon atoms is oxidized into a ketone function, provided that A and X together do not represent a nitrogen atom,
B represents a nitrogen-containing heterocycle or an amine group optionally substituted with one or two $C_1$-$C_4$ alkyl groups,
b) the addition salts of the above formula I compounds with an acid.

The invention, when the formula I compounds comprise a centre of assymetry, also concerns each of the optical isomers either pure or mixed, and their respective salts or salt mixtures.

According to the invention, a method is also proposed to prepare formula I compounds and their addition salts.

The use is also put forward of a substance selected from the formula I compounds and their non-toxic addition salts for the preparation of a medicinal product which can be used in human or animal therapy intended for the prevention or treatment of pain-related pathologies, in particular hyperalgesia subsequent to an inflammatory condition, or major algesia connected with other pathological conditions such as cancer for example.

DETAILED DESCRIPTION

In formula I, by alkyl group is meant a straight, branched or cyclized hydrocarbon chain. A $C_1$-$C_3$ alkyl group is notably a methyl, ethyl, propyl, cyclopropyl or 1-methyl-ethyl group. A $C_1$-$C_4$ alkyl group, in addition to the above-cited examples, will notably comprise butyl, 1-methylpropyl and 1,1-dimethylethyl groups.

By $C_1$-$C_3$ alkoxy group is meant an OR group in which R is a $C_1$-$C_3$ alkyl group, the term alkyl having the meaning given above. Said group is for example a methoxy, ethoxy, propoxy or 1-methylethoxy group.

By saturated $C_2$-$C_5$ alkylene group is meant a —$(CH_2)_n$— group in which n is 2, 3, 4 or 5 if it is a straight group or, for example a —CH($CH_3$)—$CH_2$—$CH_2$— or —C($CH_3$)$_2$—$CH_2$— group if it is a branched group. By an alkylene group interrupted by an oxygen atom is meant for example the groups —$CH_2$—$CH_2$—O—$CH_2$—, —$CH_2$—O—$CH_2$—$CH_2$— or even —$CH_2$—$CH_2$—O—$CH_2$—$CH_2$—.

By unsaturated $C_2$-$C_4$ alkylene group, is meant a group comprising 2 to 4 carbon atoms of which 2 consecutive atoms are bound by an ethylene bond, for example the groups —$CH_2$—CH=CH—$CH_2$—, —CH=CH—$CH_2$—, —CH=C($CH_3$)—$CH_2$—, $CH_2$—CH=CH— or —CH=CH—CH($CH_3$)—.

By halogen is meant an atom of fluorine, chlorine or bromine and preferably a fluorine or chlorine atom.

By alkylamino or dialkylamino groups is meant the NH(R) or N(R)$_2$ groups in which R is a $C_1$-$C_4$ alkyl group, the term alkyl having the meaning given above.

By nitrogen-containing heterocycle is notably meant the azetidine, pyrrolidine, morpholine, piperidine, piperazine, N-($C_1$-$C_4$)alkylpiperidine, N-($C_1$-$C_4$)alkylpiperazine, quinuclidine, tropane, N-($C_1$-$C_4$)alkylhomopiperazine, aminopyridine and N-($C_1$-$C_4$)alkylimidazole rings.

By addition salts is meant the addition salts obtained by reaction of a formula I compound containing at least one basic function in its non-salified form, with a mineral or organic acid. Preferably, these are pharmaceutically acceptable addition salts.

Among the mineral acids suitable for salifying a basic compound of formula I, preference is given to hydrochloric, hydrobromic, phosphoric and sulphuric acids. Among the organic acids suitable for salifying a basic compound of formula 1, preference is given to methanesulphonic, benzenesulphonic, toluenesulphonic, maleic, fumaric, oxalic, citric, tartaric, lactic and trifluoroacetic acids.

Among the formula I compounds, preference is given to those which meet at least one of the following conditions:

$R_1$ represents hydrogen, a halogen, a $C_1$-$C_3$ alkyl group or $C_1$-$C_3$ alkoxy group;

$R_2$ represents a halogen, a $C_1$-$C_3$ alkyl group or $CF_3$ group;

$R_3$ represents hydrogen, a halogen, a $C_1$-$C_3$ alkyl group or $C_1$-$C_3$ alkoxy group;

$R_4$ represents hydrogen or a $C_1$-$C_3$ alkyl group;

$R_a$ represents a methyl group;

Y represents a saturated $C_2$-$C_5$ alkylene group, optionally interrupted by an oxygen atom;

p represents 2;

A represents a single bond or a straight or branched $C_1$-$C_5$ alklene group;

B represents an azetidinyl, pyrrolidinyl, morpholinyl, piperidinyl, piperazinyl, N-($C_1$-$C_4$)alkylpiperidinyl, N-($C_1$-$C_4$)alkylpiperazinyl, quinuclidinyl, tropanyl or N-($C_1$-$C_4$)alkylhomopiperazinyl group.

Particular preference is given to formula I compounds which meet at least one of the following conditions:

$R_1$ represents a $C_1$-$C_3$ alkoxy group;

$R_2$ and $R_3$ each represent a $C_1$-$C_3$ alkyl group, preferably a methyl group at position 2,6 on the aromatic ring;

$R_4$ represents hydrogen;

Y represents a $C_3$-$C_5$ alkylene group interrupted by an oxygen atom, preferably a —$CH_2$—$CH_2$—O—$CH_2$— group;

B represents a piperidinyl, N-($C_1$-$C_4$)alkylpiperidinyl, or N-($C_1$-$C_4$) alkylpiperazinyl group.

Preference is also given to compounds of formula Ia:

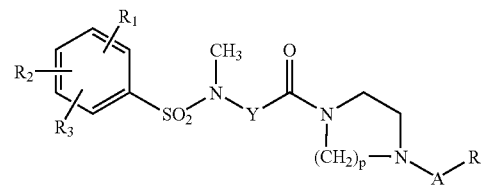

in which $R_1$ represent one atom or group of atoms selected from a hydrogen atom, halogens, $C_1$-$C_3$ alkyl groups, $C_1$-$C_3$ alkoxy groups, $CF_3$ or $OCF_3$ groups, $R_2$ represents one atom or group of atoms selected from a hydrogen atom, halogens, $C_1$-$C_3$ alkyl groups, $C_1$-$C_3$ alkoxy groups, $CF_3$ or $OCF_3$ groups, $R_3$ represents one atom or group of atoms selected from a hydrogen atom, halogens, $C_1$-$C_3$ alkyl groups, $C_1$-$C_3$ alkoxy groups, $CF_3$ or $OCF_3$ groups Y represents a saturated $C_2$-$C_5$ alkylene group, optionally interrupted by an oxygen atom, an unsaturated $C_2$-$C_4$ alkylene group or a —$CH_2$—CO—NH—$CH_2$— group, A represents a single bond or a —$(CH_2)_m$— group, R represents a saturated nitrogen-containing heterocycle, notably selected from the pyrrolidine, morpholine, piperidine, quinuclidine, tropane rings, or a tertiary amine group, notably a dialkylamino group, m and p each independently represent 2 or 3.

Preference is also given to compounds of formula Ib:

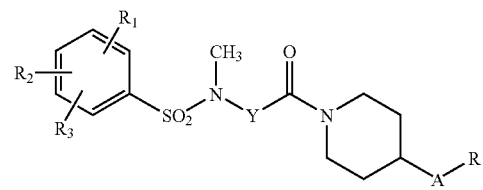

in which $R_1$, $R_2$, $R_3$ each independently represent one or more atoms or groups of atoms selected from a hydrogen atom, halogens, $C_1$-$C_3$ alkyl groups, $C_1$-$C_3$ alkoxy groups, $CF_3$ or $OCF_3$ groups, Y represents a saturated $C_2$-$C_5$ alkylene group, optionally interrupted by an oxygen atom, an unsaturated $C_2$-$C_4$ alkylene group, or a —$CH_2$—CO—NH—$CH_2$— group, A represents a single bond or a saturated $C_1$-$C_5$ alkylene group, optionally hydroxylated, R represents a saturated nitrogen-containing heterocycle notably selected from the N-methylpiperazine, N-methylpiperidine rings, or a tertiary amine group, notably a dialkylamino group.

According to the invention, a general method is put forth for preparing formula I compounds or their addition salts, comprising the steps consisting of:

a) allowing an acid of formula:

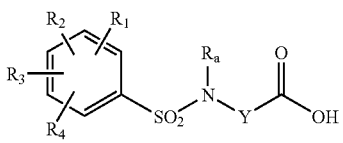

in which
R$_1$, R$_2$, R$_3$, R$_4$ each independently represent one or more atoms or groups of atoms selected from a hydrogen atom, halogens, C$_1$-C$_3$ alkyl groups, C$_1$-C$_3$ alkoxy groups, CF$_3$ or OCF$_3$ groups,
R$_a$ represents a C$_1$-C$_4$ alkyl group,
Y represents a saturated C$_2$-C$_5$ alkylene group, optionally interrupted by an oxygen atom, an unsaturated C$_2$-C$_4$ alkylene group, or a —CH$_2$—CO—NH—CH$_2$— group, to react with a nitrogen-containing heterocycle of formula:

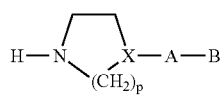

in which
X represents CH or a nitrogen atom,
p represents 2 or 3,
A represents a single bond, a nitrogen atom optionally substituted with a methyl group (if X does not also represent a nitrogen atom), or a straight or branched C$_1$-C$_5$ alkylene group, optionally hydroxylated or of which one of the carbon atoms is oxidized into a ketone function,
B represents a nitrogen-containing heterocycle or an amine group optionally substituted with one or two C$_1$-C$_4$ alkyl groups, on the understanding that if a non-substituted nitrogen atom is present, this nitrogen atom is protected by an amino-protecting group such as a Boc group (1,1-dimethylethoxycarbonyl) or Cbz group (phenylmethoxycarbonyl) for example, in a solvent such as tetrahydrofuran, dichloromethane or dimethylformamide for example, in the presence of activators such as EDCI (1-(3-dimethylaminopropyl)-3-ethylcarbodiimide), DIC (diisopropylcarbodiimide) or HOAT (1-hydroxy-7-azabenzotriazole), at a temperature generally lying between ambient temperature and the boiling point of the solvent, for approximately 2 to 15 hours, to obtain the amide of formula:

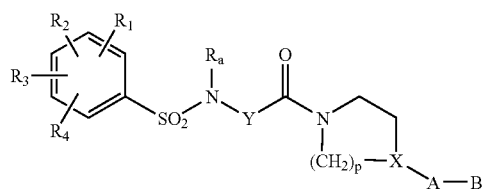

in which R$_1$, R$_2$, R$_3$, R$_4$, R$_a$, Y, p, X, A and B maintain the same meaning as in the starting products,
b) if necessary, removing the amino-protecting groups, for example through the action of trifluoroacetic acid in the presence of anisole if said amino-protecting group is a Boc group, or by catalytic hydrogenation if the protecting group is a Cbz group,
c) if necessary, obtaining an addition salt of the formula I compound with a mineral or organic acid, following usual procedures known to persons skilled in the art.

This general method for preparing an amide function starting with a carboxylic acid and an amine may be modified to use activators immobilized on an insoluble resin, for example resins having a polystyrene skeleton supporting carbodiimide functions.

As a variant of the above-described general method, the acid of formula II may be converted intermediately into an acid chloride of formula IIa,

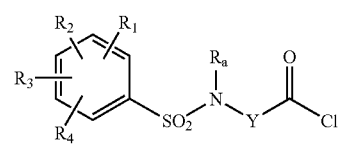

notably through the action of a chlorinating agent such as oxalyl chloride or thionyl chloride, said acid chloride then being allowed to react with the nitrogen-containing heterocycle of formula III using a conventional reaction conducted in a solvent and preferably in the presence of an aprotic organic base such as triethylamine or pyridine for example, to obtain the compound of formula I.

The acids of formula II in which Y represents a —CH$_2$—CH$_2$—O—CH$_2$— group may be prepared following a method consisting of:
a) allowing a benzenesulphonyl chloride of formula:

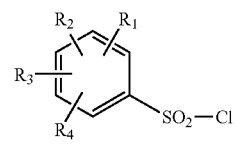

in which R$_1$, R$_2$, R$_3$ and R$_4$ each independently represent a hydrogen or halogen atom, a C$_1$-C$_3$ alkyl group, a C$_1$-C$_3$ alkoxy group, CF$_3$ or OCF$_3$ group, to react with an aminoalcohol of formula:

HN(R$_a$)—CH$_2$—CH$_2$—OH in which R$_a$ represents a C$_1$-C$_4$ alkyl group,
in a solvent such as dichloromethane for example, in the presence of an aprotic organic base such as triethylamine or pyridine for example, at a temperature lying between approximately 0 and 50° C., for approximately 1 to 3 hours, to obtain the sulphonamide of formula:

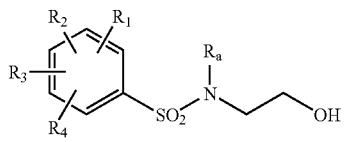

V in which $R_1$, $R_2$, $R_3$, $R_4$ and $R_a$ remain unchanged, b) allowing the compound of formula V obtained above to react with an ester of bromacetic acid, preferably the t-butyl ester, in the presence of a base such as sodium hydroxide for example and in a phase-transfer promoting medium containing quarternary ammonium salts, in a mixture of solvents such as water and toluene, at a temperature lying between approximately 0° C. and 40° C. for approximately 1 to 5 hours, to obtain the ester of formula:

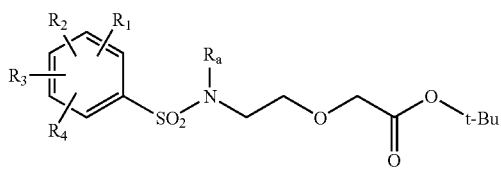

VI c) hydrolysing the ester of formula VI, for example through the action of trifluoroacetic acid, the reaction being conducted in a solvent such as dichloromethane, at a temperature lying between approximately 0° C. and 50° C. for approximately 1 to 6 hours, to obtain the acid of formula II:

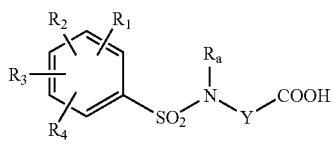

II in which $R_1$, $R_2$, $R_3$, $R_4$ and $R_a$ remain unchanged and Y represents a —$CH_2$—$CH_2$—O—$CH_2$— group.

As a variant of the general method, the formula I compounds may be obtained by successively performing the steps consisting of:

a) allowing an acid compound of formula:

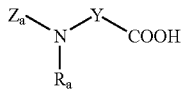

VII in which $R_a$ represents a $C_1$-$C_4$ alkyl group,
Y represents a saturated $C_2$-$C_5$ alkylene group, optionally interrupted by an oxygen atom, and $Z_a$ represents an amino-protecting group such as a benzyl group for example, to react with a nitrogen-containing heterocycle of formula:

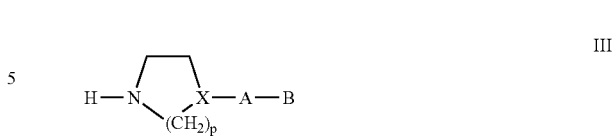

III in which
X represents CH or a nitrogen atom,
p represents 2 or 3,
A represents a single bond, a nitrogen atom optionally substituted with a methyl group (if X does not also represent a nitrogen atom), or a straight or branched $C_1$-$C_5$ alkylene group optionally hydroxylated or of which one of the carbon atoms is oxidized into a ketone function,
B represents a nitrogen-containing heterocycle or an amine group optionally substituted with one or two $C_1$-$C_4$ alkyl groups, on the understanding that, should a non-substituted nitrogen atom be present, this nitrogen atom is protected by a different amino-protecting group to the amino-protecting group used for acid compound VII, such as a Boc group (1,1-dimethylethoxycarbonyl), in a solvent such as tetrahydrofuran or dichloromethane or dimethylformamide for example, in the presence of activators such as EDCI (1-(3-dimethylaminopropyl)-3-ethylcarbodiimide), DIC (diisopropylcarbodiimide) or HOAT (1-hydroxy-7-azabenzotriazole) for example, at a temperature generally lying between ambient temperature and the boiling point of the solvent, for approximately 2 to 15 hours, to obtain the amide of formula:

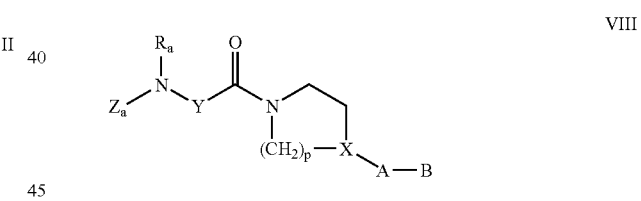

VIII in which $Z_a$, $R_a$, Y, p, X, A and B maintain the same meaning as in the starting compounds, b) removing the $Z_a$ amino-protecting group, for example by catalytic hydrogenation if $Z_a$ is a benzyl group, to obtain the secondary amine of formula:

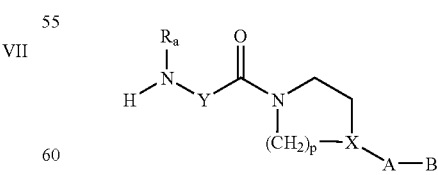

IX in which $R_a$, Y, p, X, A and B maintain the same meaning as in the preceding compound, c) allowing this secondary amine IX to react with a benzenesulphonyl chloride of formula:

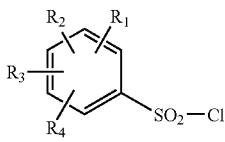

in which $R_1$, $R_2$, $R_3$ and $R_4$ each independently represent a hydrogen or halogen atom, a $C_1$-$C_3$ alkyl group or a $C_1$-$C_3$ alkoxy group, $CF_3$ or $OCF_3$ group, in a solvent such as dichloromethane for example, in the presence of an aprotic organic base such as triethylamine or pyridine for example, at a temperature lying between approximately 0 and 50° C., for approximately 1 to 3 hours, to obtain the sulphonamide of formula:

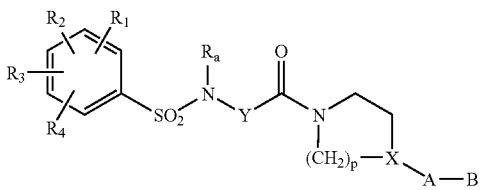

in which $R_1$, $R_2$, $R_3$, $R_4$, $R_a$, Y, p, X, A and B maintain the same meaning as in the starting compounds, d) if necessary, removing the amino-protecting groups, for example through the action of trifluoroacetic acid in the presence of anisole if said amino-protecting group is a Boc group, e) if necessary, obtaining an addition salt of the formula I compound with a mineral or organic acid.

As a variant of the above method, step a) to form the amide bond may be conducted by first forming the acid chloride of formula VII, for example through the action of oxalyl chloride or thionyl chloride in an anhydrous aprotic solvent, followed by reaction of the acid chloride obtained with the formula III amine as described above, in a solvent and for example in the presence of an aprotic base such as triethylamine.

The heterocyclic derivatives of formula III are known compounds, commercially available or described in the literature, or may be prepared using methods known to persons skilled in the art, for example through a reductive amination reaction between piperazine or homopiperazine and a ketone, for example in the presence of titanium isopropoxide then a reaction with a reducing agent such as sodium cyanoborohydride, or, if piperidine derivatives are used, through catalytic hydrogenation of pyridine-homologous compounds.

The invention will be more readily understood with the help of examples of preparation of compounds and the results of pharmacological tests demonstrating the therapeutic usefulness of these compounds. These examples are non-limiting and cannot be interpreted as limiting the scope of the invention.

Among the abbreviations used in the description, M means mole, mM means millimole ($10^{-3}$ mole). THF means tetrahydrofurane, DCM means dichloromethane, DMF means dimethylformamide, TFA means trifluoroacetic acid. For compounds having a centre of assymetry, the absence of any particular indication means that the compound is in the form of the racemic mixture. In the spectral data for nuclear magnetic resonance, chemical shifts are indicated with reference to TMS (tetramethylsilane).

PREPARATION I

N(2-hydroxyethyl)-4-methoxy-N,2,6-trimethylbenzene- sulphonamide

A solution of 1.76 g (23.4 mM) of 2-(methylamino)ethanol is prepared in 100 ml of DCM and 5.4 g (53 mM) of triethylamine are added. The mixture is cooled to 0° C. and a solution of 5 g (21.3 mM) of 2,6 dimethyl-4-methoxybenzenesulphonyl chloride in 50 ml of DCM is added progressively. The mixture is then agitated for 3 hours at ambient temperature, and then poured over 50 ml of 0.5 N hydrochloric acid. The organic phase is separated and then washed with water, dried over magnesium sulphate and concentrated under reduced pressure. 5.8 g of the compound sought after are thus obtained as a colourless oil (yield=100%).

$^1$H NMR (300 MHz, DMSO) δ: 6.80 (s, 2H); 4.70 (t, 1H); 3.80 (s, 3H); 3.48 (q, 2H); 3.09 (t, 2H); 2.69 (s, 3H); 2.54 (s, 6H).

PREPARATION II

[2-[[(4-methoxy-2,6-dimethylphenyl)sulphonyl]methylamino]-ethoxy]acetic acid, 1,1-dimethylethyl ester A solution of 4.85 g (17.7 mM) of the compound obtained according to preparation I is prepared in 100 ml of toluene and 1.62 g of tetrabutylammonium chloride are added. The mixture is cooled to 0° C. and 100 ml of 35% sodium hydroxide are then added, then, progressively, 3.95 ml (26.6 mM) of t-butyl bromacetate are added. The mixture is agitated at ambient temperature for 2 hours and the organic phase is then separated by decanting, and washed with water to neutral pH and then dried over sodium sulphate. After concentration under reduced pressure, an oil is obtained which is purified by silica gel chromatography in eluting with the aid of a cyclohexane/ethyl acetate mixture (75/25; v/v). 6.5 g of the compound sought after are thus obtained as a colourless oil (yield=94%).

$^1$H NMR (250 MHz, DMSO) δ: 6.80 (s, 2H); 3.89 (s, 2H); 3.80 (s, 3H); 3.56 (t, 2H); 3.21 (t, 2H); 2.71 (s, 3H); 2.53 (s, 3H); 1.41 (s, 9H).

PREPARATION III

[2-[[(4-methoxy-2,6-dimethylphenyl)sulphonyl]methylamino]-ethoxy]acetic acid 6.4 g (16.5 mM) of the ester obtained according to preparation II are dissolved in 80 ml of DCM, and 8 ml of trifluoroacetic acid are added. The mixture is agitated at ambient temperature for 4 hours, and then concentrated under reduced pressure. The residue from evaporation is taken up into solution in 100 ml of 1N sodium hydroxide and the solution obtained is washed twice with 30 ml of ethyl acetate, and then acidified with an N solution of hydrochloric acid and extracted with twice 80 ml of ethyl acetate. The organic phase is washed with water, dried over sodium sulphate and concentrated under pressure. The acid sought after is thus obtained as an oil which crystallises (yield=95%).

M.Pt.=82° C.

EXAMPLE 1

1-[[2-[[(4-methoxy-2,6-dimethylphenyl)sulphonyl] methylamino]-ethoxy]acetyl]-4-[2-(1-pyrrolidinyl) ethyl]piperazine, bis-trifluoroacetate 482 mg cyclohexyldiimide grafted polystyrene resin are placed in 5 ml of THF for 20 minutes and 100 mg (0.31 mM) of the acid obtained according to preparation III in solution in 2 ml of THF, 37 mg (0.20 mM) of 1-[2-(1-pyrrolidinyl)ethyl] piperazine and 2 mg of HOAT (1-hydroxy-7-azabenzotriazole), are then added. The mixture is agitated for 4 hours at ambient temperature and then filtered. The resin is rinsed with 4 ml of THF which is added to the filtrate. The filtrate is then agitated with 50 mg of Amberlite IRA 400 resin (as OH⁻), for 3 hours. After filtration, the resin is rinsed with 3 ml of THF which is added to the filtrate. This filtrate is then treated with 100 mg of isocyanate grafted polystyrene resin for 1 hour. The resin is separated off by filtration and the solution is concentrated under reduced pressure. The residue (63 mg) is purified by reverse phase chromatography on an X Terra Prep MS C18 column (eluent A: water+0.05% TFA, eluent B: acetonitrile+ 0.05% TFA, gradient: 10% B (t=0 to 2 minutes) 60% B (t=2 to 17 minutes) 100% B (t=17 minutes to 18 minutes); flow rate=25 ml/mn; UV detection from 120 to 260 nm. The purified product is taken up into 1 ml of acetonitrile and it is mixed with 6 ml of a 1% solution of trifluoroacetic acid in water. The solution obtained is then freeze-dried and 19 mg of the salt sought after are obtained as a yellow oil (yield=13%).

$^1$H NMR (300 MHz, CD$_3$CN) δ: 6.74 (s, 2H); 4.09 (s, 2H); 3.96 (s, 3H); 3.70 (m, 1H); 3.59 (t, 2H); 3.48 (t, 2H); 3.33 (m, 5H); 3.19 (t, 2H); 3.00 (m, 4H); 2.72 (s; 3H); 2.56 (s, 6H); 2.04 (m, 4H).

PREPARATION IV

[2-[[(2,4,6-trimethylphenyl)sulphonyl]methylamino] ethoxy]-acetic acid, 1,1-dimethylethyl ester In operating analogously to preparation II, starting with N-(2-hydroxyethyl)-N,2,4,6-tetramethylbenzenesulphonamide, the ester sought after is obtained as a beige oil (yield=98%).

$^1$H NMR (250 MHz, DMSO) δ: 7.06 (s, 2H); 4.01 (s, 2H); 3.58 (t, 2H); 3.25 (t, 2H); 2.72 (s, 3H); 2.51 (s, 6H); 2.27 (s, 3H); 1.43 (s, 9H).

PREPARATION V

[2-[[(2,4,6-trimethylphenyl)sulphonyl]methylamino] ethoxy]-acetic acid

In operating analogously to preparation III, starting with the compound obtained according to preparation IV, the product sought after is obtained as a beige solid (yield=83%).
M.Pt.=58° C.

PREPARATION VI

N-ethyl-N-(2-hydroxyethyl)-4-methoxy-2,6-dimethylbenzene- sulphonamide

In operating analogously to preparation I, starting with 2-(ethylamino)ethanol, the product sought after is obtained as a yellow oil (yield=99%).

$^1$H NMR (250 MHz, DMSO) δ: 6.80 (s, 2H); 4.69 (t, 1H); 3.80 (s, 3H); 3.38 (m, 2H); 3.14 (s, 2H).

PREPARATION VII

[2-[[(4-methoxy-2,6-dimethylphenyl)sulphonyl]ethylamino]-ethoxy]acetic acid, 1,1-dimethylethyl ester In operating analogously to preparation II, starting with the compound obtained according to preparation VI, the product sought after is obtained as a colourless oil (yield=79%).

$^1$H NMR (250 MHz, DMSO) δ: 6.79 (s, 2H); 3.86 (s, 2H); 3.79 (s, 3H); 3.47 (t, 2H); 3.24 (m, 4H); 2.53 (s, 6H); 1.40 (s, 9H); 1.00 (t, 3H).

PREPARATION VIII

[2-[[(4-methoxy-2,6-dimethylphenyl)sulphonyl]ethylamino]-ethoxy]acetic acid

In operating analogously to preparation III, starting with the compound obtained according to preparation VII, the product sought after is obtained as a white solid (yield=88%).

$^1$H NMR (250 MHz, DMSO) δ: 6.79 (s, 2H); 3.89 (s, 2H); 3.79 (s, 3H); 3.48 (t, 2H); 3.24 (q, 2H); 3.21 (t, 2H); 2.53 (s, 6H); 1.00 (t, 3H).

PREPARATION IX

N-(2-hydroxyethyl)-4-methoxy-2,6-dimethyl-N-(1-methylethyl)benzene-sulphonamide

In operating analogously to preparation I, starting with 2-[(1-methylethyl)amino]ethanol, the product sought after is obtained as a colourless oil (yield=58%).

$^1$H NMR (300 MHz, DMSO) δ: 6.80 (s, 2H); 4.68 (t, 1H); 3.80 (s, 3H); 3.73 (quin, 1H); 3.27 (dt, 2H); 3.20 (q, 2H); 3.12 (t, 2H); 2.53 (s, 6H); 1.06 (d, 6H); 0.99 (t, 3H).

PREPARATION X

[2-[[(4-methoxy-2,6-dimethylphenyl)sulphonyl](1-methylethyl)amino]-ethoxy]acetic acid, 1,1-dimethylethyl ester In operating analogously to preparation II, starting with the compound obtained according to preparation IX, the product sought after is obtained as a colourless oil (yield=95%).

$^1$H NMR (250 MHz, DMSO) δ: 6.80 (s, 2H); 3.86 (s, 2H); 3.80 (s, 3H); 3.74 (quin, 1H); 3.82 (m, 2H); 3.26 (m, 2H); 2.53 (s, 6H); 1.40 (s, 9H); 1.07 (d, 6H).

PREPARATION XI

[2-[[(4-methoxy-2,6-dimethylphenyl)sulphonyl](1-methylethyl)amino]-ethoxy]acetic acid In operating analogously to preparation III, starting with the compound obtained according to preparation X, the product sought after is obtained as a white solid (yield=85%).
M.Pt.=96° C.

PREPARATION XII

N-cyclopropyl-N-(2-hydroxyethyl)-4-methoxy-2,6-dimethylbenzene-sulphonamide

In operating analogously to preparation I, starting with 2-(cyclopropylamino)ethanol, the product sought after is obtained as a white solid (yield=77%)
M.Pt.=58° C. .

PREPARATION XIII

[2-[cyclopropyl[(4-methoxy-2,6-dimethylphenyl)sulphonyl]amino]ethoxy]acetic acid, 1,1-dimethylethyl ester In operating analogously to preparation II, starting with the compound obtained according to preparation XII, the product sought after is obtained as a colourless oil (yield=84%).

$^1$H NMR (300 MHz, DMSO) δ: 6.80 (s, 2H); 3.98 (s, 2H); 3.80 (s, 3H); 3.69 (t, 2H); 3.44 (t, 2H); 2.50 (s, 6H); 2.47 (m, 1H); 1.42 (s, 9H); 0.48 (m, 2H); 0.16 (m, 2H).

PREPARATION XIV

[2-[cyclopropyl[(4-methoxy-2,6-dimethylphenyl)sulphonyl]-amino]ethoxy]acetic acid In operating analogously to preparation III, starting with the compound obtained according to preparation XIII, the product sought after is obtained as a white solid (yield=85%). M.Pt.=100° C.

PREPARATION XV 2,6-dichloro-4-methoxybenzenesulphonyl chloride and 2,4-dichloro-6-methoxybenzenesulphonyl chloride A solution is prepared of 15 g (84.7 mM) of 3,5-dichloroanisole in 8 ml of thionyl chloride that is cooled to −10° C., and 6 ml (90 mM) of chlorosulphonic acid are then added dropwise. The reaction mixture is then agitated for 3 hours at ambient temperature, and then poured over a mixture of ice and ethyl acetate. The organic phase is separated, dried over magnesium sulphate and concentrated under reduced pressure. The residue from evaporation is used, without other purification, in the next step.

PREPARATION XVIa 2,6-dichloro-N-(2-hydroxyethyl)-4-methoxy-N-methyl-benzenesulphonamide

PREPARATION XVIb 2,4-dichloro-N-(2-hydroxyethyl)-6-methoxy-N-methyl-benzenesulphonamide In operating analogously to preparation I, starting with the sulphonyl chlorides obtained according to preparation XV, the products sought after are obtained as white solids, after separation of the compounds and purification by silica gel chromatography, in eluting with the aid of a toluene/isopropanol mixture (95/5; v/v).

PREPARATION XVIa (yield=13%): M.Pt.=47° C.

PREPARATION XVIb (yield=48%): M.Pt.=100° C.

PREPARATION XVII

[2-[[(2,6-dichloro-4-methoxyphenyl)sulphonyl]methylamino]-ethoxy]acetic acid, 1,1-dimethylethyl ester In operating analogously to preparation II, starting with the compound obtained according to preparation XVIa, the product sought after is obtained as a colourless oil (yield=52%).

$^1$H NMR (300 MHz, DMSO) δ: 7.24 (s, 2H); 3.94 (s, 2H); 3.87 (s, 3H); 3.60 (t, 2H); 3.39 t, 2H); 2.90 (s, 3H); 1.41 (s, 9H).

PREPARATION XVIII

[2-[[(2,6-dichloro-4-methoxyphenyl)sulphonyl]methylamino]-ethoxy]acetic acid

In operating analogously to preparation III, starting with the compound obtained according to preparation XVII, the product sought after is obtained as a white solid (yield=94%). M.Pt.=95° C.

PREPARATION XIX

[2-[[(2,4-dichloro-6-methoxyphenyl)sulphonyl]methylamino]ethoxy]acetic acid, 1,1-dimethylethyl ester In operating analogously to preparation II, starting with the compound obtained according to preparation XVIb, the product sought after is obtained as an oil which is used, without other purification, in the next step.

PREPARATION XX

[2-[[(2,4-dichloro-6-methoxyphenyl)sulphonyl]methylamino]ethoxy]acetic acid

In operating analogously to preparation III, starting with the compound obtained according to preparation XIX, the product sought after is obtained as a white solid (yield=76%). M.Pt.=74° C.

PREPARATION XXI 2,4-dichloro-N-(2-hydroxyethyl)-3,N-dimethyl-benzenesulphonamide In operating analogously to preparation I, starting with 2,4-dichloro-3-methylbenzenesulphonyl chloride, the product sought after is obtained as a colourless oil.

PREPARATION XXII

[2-[[(2,4-dichloro-3-methylphenyl)sulphonyl]methylamino]ethoxy]acetic acid, 1,1-dimethylethyl ester In operating analogously to preparation II, starting with the compound obtained according to preparation XXI, the product sought after is obtained as a colourless oil (yield=87%).

$^1$H NMR (300 MHz, DMSO) δ: 7.83 (d, 1H); 7.63 (d, 1H); 3.93 (s, 2H); 3.59 (t, 2H); 3.39 (t, 2H); 2.91 (s, 3H); 2.49 (s, 3H); 1.41 (s, 9H).

PREPARATION XXIII

[2-[[(2,4-dichloro-3-methylphenyl)sulphonyl]methylamino]ethoxy]acetic acid

In operating analogously to preparation III, starting with the compound obtained according to preparation XXII, the product sought after is obtained as a colourless oil (yield=100%).

¹H NMR (300 MHz, DMSO) δ: 12.50 (m broad, 1H); 7.84 (d, 1H); 7.63 (d, 1H); 4.02 (s, 2H); 3.61 (t, 2H); 3.40 (t, 2H); 2.91 (s, 3H); 2.51 (s, 3H).

PREPARATION XXIV

N-(2-hydroxyethyl)-N-methyl-2-(trifluoromethyl) benzenesulphonamide

In operating analogously to preparation I, starting with 2-(trifluoromethyl)benzenesulphonyl chloride, the product sought after is obtained as a yellow oil (yield=99%).

¹H NMR (250 MHz, DMSO) δ: 8.02 (m, 2H); 7.88 (m, 2H); 4.84 (t, 1H); 3.55 (q, 2H); 3.30 (t, 2H); 2.93 (s, 3H).

PREPARATION XXV

[2-[[[2-(trifluoromethyl)phenyl]sulphonyl]methylamino]-ethoxy]acetic acid, 1,1-dimethylethyl ester In operating analogously to preparation II, starting with the compound obtained according to preparation XXIV, the product sought after is obtained as a yellow oil (yield=67%).

¹H NMR (250 MHz, DMSO) δ: 8.02 (m, 2H); 7.98 (m, 2H); 3.97 (s, 2H); 3.63 (t, 2H); 3.44 (t, 2H); 2.95 (s, 3H); 1.42 (s, 9H).

PREPARATION XXVI

[2-[[[2-(trifluoromethyl)phenyl]sulphonyl]methylamino]-ethoxy]acetic acid

In operating analogously to preparation III, starting with the compound obtained according to preparation XXV, the product sought after is obtained as a colourless oil (yield=78%).

¹H NMR (250 MHz, DMSO) δ: 8.02 (m, 2H); 7.86 (m, 2H); 4.01 (s, 2H); 3.65 (t, 2H); 3.45 (t, 2H); 2.95 (s, 3H).

PREPARATION XXVII

[2-[[[4-methoxy-2-(trifluoromethyl)phenyl]sulphonyl]-methylamino]ethoxy]acetic acid A suspension is prepared of 8 g (60 mM) of 2-(2-methylaminoethoxy)acetic acid in 100 ml of chloroform and 20 ml of acetonitrile, and, at ambient temperature, 17 ml (120 mM) of triethylamine are added, then, dropwise, 7.63 ml (60 mM) of chlorotrimethylsilane. The mixture is agitated at 60° C. for 2 hours and then cooled to ambient temperature and 17 ml (120 mM) of triethylamine and then 16.48 g (60 mM) of 4-methoxy-2-(trifluoromethyl)benzenesulphonyl chloride in solution in 60 ml of chloroform, are added slowly. The reaction mixture is kept under agitation at 5° C. for 16 hours, and then concentrated under reduced pressure. The residue is taken up into 150 ml of dichloromethane and is treated with 40 ml of an N solution of hydrochloric acid. The organic phase is separated, washed with water, and then extracted with twice 120 ml of N sodium hydroxide. The basic aqueous phase is separated, washed with 100 ml of dichloromethane and then acidified with a 5N solution of hydrochloric acid. The precipitate formed is extracted with twice 80 ml of dichloromethane; the organic phase obtained is washed with water and then dried over magnesium sulphate and concentrated under reduced pressure. The residue obtained is crystallised in isopropyl ether, separated off and dried. 6.32 g of the compound sought after are thus obtained as a white solid (yield=28%).

M.Pt.=60° C.

PREPARATION XXVIII 4-(3-quinuclidinyl)piperazine-1-carboxylic acid, 1,1-dimethylethyl ester 1 g (8 mM) of quinuclidinone, 1.63 g (8.75 mM) of 1-piperazinecarboxylic acid t-butyl ester (1-Boc-piperazine) and 2.71 ml (9.1 mM) of titanium isopropoxide are mixed and this mixture is kept under agitation for 1 hour. 5 ml of ethanol and then 460 mg (7.3 mM) of sodium cyanoborohydride are then added, and this mixture is agitated for 24 hours at ambient temperature. 25 ml of water are added and agitation is carried out for 15 minutes. The precipitate formed is separated off by filtration and the filtrate is concentrated under reduced pressure. The residue is purified by NH₂ silica gel chromatography in eluting with the aid of a toluene/isopropanol mixture (95/5; v/v). 1 g of the compound sought after are thus obtained as a white solid (yield=42%).

M.Pt.=174° C.

PREPARATION XXIX (3RS)-3-(1-piperazinyl)-1-azabicyclo[2.2.2]octane or: (3(RS)-3-(1-piperazinyl)quinuclidine)

A solution is prepared of 990 mg (3.35 mM) of the compound obtained according to preparation XXVIII in 10 ml of trifluoroacetic acid and the mixture is agitated for 30 minutes at 10° C. 30 ml of toluene are then added and concentration is carried out under reduced pressure. The residue is taken up into 25 ml of methanol and the solution is agitated with 20 g of Amberlite IRA 400 resin (OH⁻) for 1 hour at ambient temperature. The resin is separated off by filtration, rinsed with 15 ml of methanol and the combined filtrates are concentrated under reduced pressure. 530 mg of the product sought after are thus obtained as a white paste (yield=80%).

¹H NMR (300 MHz, DMSO) δ: 2.79 (m, 1H); 2.67 (m, 7H); 2.50 (m, 2H); 2.22 (m, 4H); 1.91 (m, 1H); 1.85 (m, 1H); 1.58 (m, 2H); 1.32 (m, 1H); 1.22 (m, 1H).

EXAMPLE 2

N-[2-[2-[4-[(3RS)-1-azabicyclo[2.2.2]oct-3-yl-1-piperazinyl]-2-oxo-ethoxy]ethyl]-N,2,4,6-tetramethylbenzenesulphonamide, bis trifluoro-acetate 250 mg (0.32 mM) of TFP (tetrafluorophenol) grafted polystyrene resin are placed in 4 ml of DMF for 15 minutes, and 4 mg (0.03 mM) of 4-(dimethylamino)pyridine, 103 mg (0.32 mM) of acid obtained according to preparation V and 76 μl (0.48 mM) of diisopropylcarbodiimide, are then added. The mixture is kept under agitation for 18 hours, and the resin is then separated off by filtration, rinsed twice with 3 ml of DMF and allowed to react with 44 mg (0.225 mM) of the amine obtained according to preparation XXIX, in 3 ml of DMF. The mixture is agitated for 1 hour at ambient temperature and the resin is separated off by filtration and rinsed with twice 3 ml of DMF. The filtrates are combined and treated with 20 mg of Amberlite IRA 400 resin (OH—), and then with 20 mg of isocyanate grafted resin, and then concentrated under reduced pressure. The residue is purified by semi-preparative chromatography (conditions analogous to those of Example 1). 16 mg of the compound sought after are thus obtained as a white solid (yield=8%)

M.Pt.=78-80° C. .

EXAMPLE 3

N-[2-[2-[4-[(3RS)-1-azabicyclo[2.2.2]oct-3-yl]-1-piperazinyl]-2-oxo-ethoxy]ethyl]-4-methoxy-N,2,6-trimethylbenzenesulphonamide 500 mg (1.51 mM) of acid obtained according to preparation III, 319 mg (1.65 mM) of EDCI, 2.26 mg (1.65 mg) of HOAT and 233 µl of triethylamine are mixed in 10 ml of DMF and this reaction mixture is kept under agitation at ambient temperature for 30 minutes. 334 mg of the amine obtained according to preparation XXIX are then added and agitation is carried out for 20 hours at ambient temperature. The reaction mixture is poured onto iced water and extracted with DCM. The organic phase is dried over magnesium sulphate and concentrated under reduced pressure. The residue is purified by $NH_2$ grafted silica gel chromatography in eluting with a toluene/isopropanol mixture (95/5; v/v). 140 mg of the product sought after are thus obtained as a colourless oil (yield=18%).

$^1$H NMR (300 MHz, DMSO) δ: 6.80 (s, 2H); 4.05 (s, 2H); 3.80 (s, 3H); 3.53 (t, 2H); 3.41 (m, 2H); 3.31 (m, 2H); 3.22 (t, 2H); 2.85 (m, 1H); 2.70 (s, 3H); 2.57 (m, 5H); 2.53 (s, 6H); 2.27 (m, 4H); 1.90 (m, 2H); 1.60 (m, 2H); 1.35 (m, 1H); 1.20 (m, 1H).

EXAMPLE 4

N-[2-[2-[4-[(3RS)-1-azabicyclo[2.2.2]oct-3-yl]-1-piperazinyl]-2-oxo-ethoxy]ethyl]-4-methoxy-N,2,6-trimethylbenzenesulphonamide, difumarate A solution is prepared of 137 mg (0.269 mM) of the compound obtained according to Example 3 in 3 ml of methanol and 62.5 mg (0.538 mM) of fumaric acid are added. The mixture is agitated for 30 minutes and then concentrated under reduced pressure. The residue is taken up into 5 ml of water and is freeze-dried. 200 mg of the salt sought after are thus obtained as a white powder (quantitative yield).

M.Pt.=86-90° C.

EXAMPLE 5

N-[2-[2-[4-[(3S)-1-azabicyclo[2.2.2]oct-3-yl]-1-piperazinyl]-2-oxo-ethoxy]ethyl]-4-methoxy-N,2,6-trimethylbenzenesulphonamide 840 mg (2.53 mM) of acid obtained according to preparation III are mixed in 8 ml of anhydrous toluene and 0.1 ml of DMF. 0.245 ml (2.81 mM) of oxalyl chloride are added slowly. The reaction mixture is agitated for an hour at ambient temperature and is then concentrated under reduced pressure. The residue is taken up into 10 ml of toluene and is added dropwise to a solution of 0.5 g (2.56 mM) of 3(S)-(1-piperazinyl)quinuclidine and 0.39 ml (2.81 mM) of triethylamine in 10 ml of toluene. The reaction mixture is agitated for an hour at ambient temperature and 2 ml of ethanol and 10 g of silica gel for chromatography are then added. The solvents are removed under reduced pressure and the product which is adsorbed on the silica is purified by silica gel chromatography in eluting with the aid of an ethyl acetate/ethanol/aqueous ammonia mixture (6/3/1; v/v/v). The pure fractions are concentrated under reduced pressure, taken up into solution in ethyl acetate, dried over magnesium sulphate and concentrated. The product sought after is thus obtained as a colourless oil (yield=71%).

$^1$H NMR (300 MHz, DMSO) δ: 6.80 (s, 2H); 4.06 (t, 2H); 3.80 (s, 3H); 3.53 (t, 2H); 3.41 (m, 2H); 3.31 (m, 2H); 3.22 (t, 2H); 2.85 (m, 1H); 2.69 (s, 3H); 2.57 (m, 5H); 2.53 (s, 6H); 2.27 (m, 4H); 1.90 (m, 2H); 1.60 (m, 2H); 1.35 (m, 1H); 1.20 (m, 1H).

EXAMPLE 6

N-[2-[2-[4-[(3S)-1-azabicyclo[2.2.2]oct-3-yl]-1-piperazinyl]-2-oxo-ethoxy]ethyl]-4-methoxy-N,2,6-trimethylbenzenesulphonamide, fumarate 0.84 g (1.65 mM) of the compound obtained according to Example 5 are dissolved in 50 ml of methanol and 0.192 g (1.64 mM) of fumaric acid are added. The mixture is agitated until complete dissolution and is concentrated under reduced pressure. The residue is taken up into solution in 40 ml of water, the solution is filtered and freeze-dried. 1 g of the salt sought after are thus obtained as a white powder (yield=97%).

M.Pt.=86° C.

$[\alpha]^{25}_D = -6.5°$ (C=0.31; $CH_3OH$)

EXAMPLE 7

N-[2-[2-[4-[(3R)-1-azabicyclo[2.2.2]oct-3-yl]-1-piperazinyl]-2-oxo-ethoxy]ethyl]-4-methoxy-N,2,6-trimethylbenzenesulphonamide, fumarate The racemic mixture obtained according to Example 3 is separated by chromatography on chiral phase (Chiralpack AD column) in eluting with a hexane/ethanol/isopropanol/trifluoroacetic acid mixture (60/25/15/0.05). Starting with 500 mg of the racemic mixture, 260 mg of enantiomer S and 100 mg of enantiomer R are obtained. Each enantiomer is placed in solution in methanol and treated with 1 g of Amberlite IRA 400 resin ($OH^-$). The treated solution is filtered and concentrated under reduced pressure and the basic compounds obtained are salified with fumaric acid, analogously to the operation described for Example 6. 143 mg of enantiomer S and 68 mg of enantiomer R are thus obtained.

M.Pt.=84° C.

$[\alpha]^{27}_D = 7.2°$ (C=0.31; $CH_3OH$)

PREPARATION XXX 4-(8-methyl-8-azabicyclo[3.2.1]oct-3-yl)-1-piperazine-carboxylic acid, 1,1-dimethylethyl ester In operating analogously to preparation XXVIII, starting with 8-methyl-8-azabicyclo[3.2.1]octan-3-one (tropinone), the ester sought after is obtained as a white solid (yield=53%)

$^1$H NMR (300 MHz, DMSO) δ: 3.25 (m, 4H); 3.15 (m, 2H); 2.51 (m, 2H); 2.35 (m, 4H); 2.20 (s, 3H); 1.92 (m, 3H); 1.53 (m, 4H); 1.38 (s, 9H).

PREPARATION XXXI 8-methyl-3-(1-piperazinyl)-8-azabicyclo[3.2.1]octane

In operating analogously to preparation XXIX, starting with the compound obtained according to preparation XXX, the product sought after is obtained as a yellow oil (yield=99%).

$^1$H NMR (300 MHz, DMSO) δ: 3.70 (m, 2H); 3.03 (m, 4H); 2.75 (m, 1H); 2.61 (m, 4H); 2.53 (s, 3H); 2.10 (m, 2H); 1.75 (m, 6H).

PREPARATION XXXII 4-(1-azabicyclo[2.2.2]oct-3-yl)hexahydro-1H-1,4-diazepine-1-carboxylic acid, 1,1-dimethylethyl ester In operating analogously to preparation XXVIII, starting with 1-homopiperazinecarboxylic acid t-butyl ester, the product sought after is obtained as a colourless paste (yield=67%).

$^1$H NMR (300 MHz, DMSO) δ: 3.34 (m, 4H); 2.81-2.35 (m, 11H); 1.88 (m, 1H); 1.65 (m, 4H); 1.39 (s, 9H); 1.34 (m, 1H); 1.18 (m, 1H).

PREPARATION XXXIII 3-(hexahydro-1-1,4-diazepine-1-yl)-1-azabicyclo[2.2.2]octane In operating analogously to preparation XXIX, starting with the compound obtained according to preparation XXXII, the product sought after is obtained as a yellow oil (yield=98%).

$^1$H NMR (250 MHz, DMSO) δ: 3.41 (m, 1H); 3.11 (m, 8H); 2.96 (m, 1H); 2.78 (m, 4H); 2.52 (m, 1H); 2.24 (m, 1H); 1.89 (m, 4H); 1.85 (m, 1H); 1.62 (m, 1H).

In operating analogously to Example 1, starting with kown piperazine derivatives described in the literature or described above, the following Examples are prepared:

EXAMPLE 8

1-[[2-[[(4-methoxy-2,6-dimethylphenyl)sulphonyl]methylamino]-acetyl]-4-[3-(1-pyrrolidinyl)propyl]piperazine, bis-trifluoroacetate Yield=90% (colourless paste). $^1$H NMR (300 MHz, CD$_3$CN) δ: 6.74 (s, 2H); 4.12 (s, 2H); 3.81 (s, 3H); 3.78 (m, 4H); 3.62 (t, 2H); 3.34 (t, 2H); 3.27 (m, 12H); 2.73 (s, 3H); 2.57 (s, 6H); 2.22 (m, 2H); 2.03 (m, 4H).

EXAMPLE 9

1-[[2-[[(4-methoxy-2,6-dimethylphenyl)sulphonyl]methylamino]-ethoxy]-acetyl]-4-[2-(4-morpholinyl)ethyl]piperazine, bis-trifluoroacetate Yield=51% (colourless paste)

$^1$H NMR (300 MHz, CD$_3$CN) δ: 6.75 (s, 2H); 4.11 (s, 2H); 3.92 (m, 4H); 3.81 (s, 3H); 3.76 (m, 4H); 3.61 (t, 2H); 3.48 (m, 4H); 3.35 (t, 2H); 3.27 (m, 8H); 2.72 (s, 3H); 2.57 (s, 6H).

EXAMPLE 10

1-[[2-[[(4-methoxy-2,6-dimethylphenyl)sulphonyl]methylamino]ethoxy]acetyl]-4-[2-(1-piperidinyl)ethyl]piperazine, bis-trifluoroacetate Yield=92% (colourless paste)

$^1$H NMR (300 MHz, CD$_3$CN) δ: 6.74 (s, 2H); 4.10 (s, 2H); 3.81 (s, 3H); 3.81 (m, 4H); 3.61 (t, 2H); 3.40 (m, 2H); 3.34 (m, 4H); 3.24 (m, 4H); 3.09 (m, 4H); 2.74 (s, 3H); 2.57 (s, 6H); 1.90 (m, 4H); 1.64 (m, 2H).

EXAMPLE 11

1-[[2-[[(4-methoxy-2,6-dimethylphenyl)sulphonyl]methylamino]ethoxy]acetyl]-4-[3-(1-piperidinyl)propyl]piperazine, bis-trifluoroacetate Yield=85% (colourless paste).

$^1$H NMR (300 MHz, CD$_3$CN) δ: 6.74 (s, 2H); 4.10 (s, 2H); 3.96 (s, 3H); 3.80 (m, 2H); 3.60 (t, 2H); 3.50 (m, 4H); 3.30 (t, 2H); 3.15 (m, 2H); 3.10 (m, 4H); 2.80 (m, 4H); 2.75 (s; 3H); 2.55 (s, 6H); 2.20 (m, 2H); 1.93 (m, 5H); 1.37 (m, 1H).

EXAMPLE 12

1-[[2-[[(4-methoxy-2,6-dimethylphenyl)sulphonyl]methylamino]-ethoxy]-acetyl]-4-[3-(dimethylamino)propyl]piperazine, bis-trifluoroacetate Yield=74% (colourless paste)

$^1$H NMR (300 MHz, CD3CN) δ: 6.74 (s, 2H); 4.11 (s, 2H); 3.81 (s, 3H); 3.78 (m, 4H); 3.63 (t, 2H); 3.31 (t, 2H); 3.22 (m, 4H); 3.15 (m, 4H); 2.81 (s, 6H); 2.74 (s, 3H); 2.57 (s, 6H); 2.23 (m, 2H).

In operating analogously to Examples 3 and 4, starting with derivatives of piperazine or of homopiperazine described above, the following Examples are prepared:

EXAMPLE 13

4-methoxy-N,2,6-trimethyl-N-[2-[2-[4-(1-methyl-4-piperidinyl)-1-piperazinyl]-2-oxoethoxy]ethyl]benzenesulphonamide, bis trifluoroacetate Yield=74% (colourless paste)

$^1$H NMR (300 MHz, CD$_3$CN) δ: 6.74 (s, 2H); 4.11 (s, 2H); 3.81 (s, 3H); 3.80 (m, 4H); 3.77 (d, 2H); 3.64 (m, 2H); 3.55 (m, 1H); 3.34 (t, 2H); 3.26 (m, 4H); 3.01 (m, 2H); 2.79 (s, 3H); 2.74 (s, 3H); 2.57 (s, 6H); 2.29 (m, 4H).

EXAMPLE 14

4-methoxy-N,2,6-trimethyl-N-[2-[2-[4-(8-methyl-8-azabicyclo[3.2.1]-oct-3-yl)-1-piperazinyl]-2-oxoethoxy]ethyl]-benzenesulphonamide, fumarate Yield=62% (white solid)
M.Pt.=88-90° C.

EXAMPLE 15

1-(1-azabicyclo[2.2.2]oct-3-yl)hexahydro-4-[[2-[[(4-methoxy-2,6-dimethylphenyl)sulphonyl]methylamino]ethoxy]acetyl]-1H-1,4-diazepine, fumarate Yield=47% (white solid)
M.Pt.=90° C.

PREPARATION XXXIV

4-[1-(1,1-dimethylethyl)-4-piperidinyl]-1-piperazinecarboxylic acid, phenylmethyl ester In operating analogously to preparation XXVIII, starting with 1-(1,1-dimethylethyl)-4-piperidinone and the benzyl ester of 1-piperazinecarboxylic acid, the product sought after is obtained as a white solid (yield=56%).
M.Pt.=70-72° C.

PREPARATION XXXV

1-[1-(1,1-dimethylethyl)-4-piperidinyl]piperazine

A solution is prepared of 570 mg (1.59 mM) of the compound obtained according to preparation XXXIV in 20 ml of methanol and 114 mg of 10% palladium on carbon are added. The mixture is agitated under an atmosphere of hydrogen for 2 hours at ambient temperature and at atmospheric pressure. The catalyst is removed by filtration and the filtrate is concentrated under reduced pressure. The crude product is purified by silica gel chromatography in eluting with the aid of a dichloromethane/methanol/aqueous ammonia mixture (90/10/1; v/v/v). 270 mg of the compound sought after are thus obtained as a white powder (yield=75%).

M.Pt.=106° C.

PREPARATION XXXVI 4-(9-methyl-9-azabicyclo[3.3.1]non-3-yl)-1-piperazinecarboxylic acid, phenylmethyl ester In operating analogously to preparation XXVIII, starting with 9-methyl-9-azabicyclo[3.3.1]nonan-3-one and the benzyl ester of 1-piperazinecarboxylic acid, the product sought after is obtained as a pale yellow solid (yield=18%).

M.Pt.=74° C.

PREPARATION XXXVII 1-(9-methyl-9-azabicyclo[3.3.1]non-3-yl)piperazine

In operating analogously to preparation XXXV, starting with the compound obtained according to preparation XXXVI, the product sought after is obtained as a yellow oil (yield=100%).

$^1$H NMR (300 MHz, D2O) δ: 3.74 (m, 2H); 3.59 (m, 1H); 3.43 (m, 4H); 3.15 (m, 4H); 3.01 and 2.97 (2s, 3H); 2.46 (dd, 1H); 2.30 (m, 2H); 2.10 (m, 4H); 1.83 (m, 3H).

PREPARATION XXXVIII 4-(11,2,2,6,6-pentamethyl-4-piperidinyl)-1-piperazinecarboxylic acid, phenylmethyl ester In operating analogously to preparation XXVIII, starting with 1,2,2,6,6-pentamethyl-4-piperidinone and the benzyl ester of 1-piperazinecarboxylic acid, the product sought after is obtained as a colourless oil (yield=52%).

$^1$H NMR (300 MHz, DMSO) δ: 7.36 (m, 5H); 5.07 (s, 2H); 3.37 (m, 4H); 2.85 (m, 1H); 2.50 (m, 7H); 1.80 (m, 2H); 1.48 (m, 2H); 1.28 (s, 6H); 1.21 (s, 6H).

PREPARATION XXXIX 1-(1,2,2,6,6-pentamethyl-4-piperidinyl)piperazine

In operating analogously to preparation XXXV, starting with the compound obtained according to preparation XXXVIII, the product sought after is obtained as a white solid (yield=35%).

M.Pt.=65° C.

PREPARATION XL

4-[1-(1-methylethyl)-4-piperidinyl]-1-piperazinecarboxylic acid, 1,1-dimethylethyl ester In operating analogously to preparation XXVIII, starting with 1-(1-methylethyl)-4-piperidinone, the product sought after is obtained as a yellow solid (yield=31%).

M.Pt.=53° C.

PREPARATION XLI

1-[1-(1-methylethyl)-4-piperidinyl]piperazine, trihydrochloride

A solution is prepared of 247 mg (0.79 mM) of the compound obtained according to preparation XL in 1 ml of methanol, and 15 ml of a 2.3 N solution of hydrogen chloride in ethyl acetate are added. The mixture is agitated for 4 hours at ambient temperature. The reaction mixture is concentrated under reduced pressure. 239 mg of the compound sought after are thus obtained as a white powder. (yield=75%).

M.Pt.=262° C.

PREPARATION XLII 4-(1-cyclopropyl-4-piperidinyl)-1-piperazinecarboxylic acid, phenylmethyl ester In operating analogously to preparation XXXIV, starting with 1-cyclopropyl-4-piperidinone, the product sought after is obtained as a white solid (yield=67%).

M.Pt.=88° C.

PREPARATION XLIII 1-(1-cyclopropyl-4-piperidinyl)piperazine

In operating analogously to preparation XXXV, starting with the compound obtained according to preparation XLII, the product sought after is obtained as a white solid (yield=92%).

M.Pt.=58° C.

PREPARATION XLIV 4-(1-methyl-4-piperidinyl)hexahydro-1H-1,4-diazepine-1-carboxylic acid, 1,1-dimethylethyl ester In operating analogously to preparation XXXII, starting with 1-methyl-4-piperidinone, the product sought after is obtained as a yellow oil (yield=78%).

$^1$H NMR (250 MHz, CDCl3) δ: 3.43 (m, 4H); 3.10 (dm, 2H); 2.70 (m, 4H); 2.61 (m, 1H); 2.44 (s, 3H); 2.28 (m, 2H); 1.86 (m, 6H); 1.45 (s, 9H).

PREPARATION XLV 1-(1-methyl-4-piperidinyl)hexahydro-1H-1,4-diazepine, trihydrochloride In operating analogously to preparation XLI, starting with the compound obtained according to preparation XLIV, the product sought after is obtained as a beige solid (yield=99%).

M.Pt.=186° C.

PREPARATION XLVI 4-(8-cyclopropyl-8-azabicyclo[3.2.1]oct-3-yl)-1-piperazinecarboxylic acid, 1,1-dimethylethyl ester In operating analogously to preparation XXVIII, starting with 8-cyclopropyl-8-azabicyclo[3.2.1]octan-3-one, the ester sought after is obtained as a white paste (yield=45%).

$^1$H NMR (300 MHz, DMSO) δ: 3.24 (m, 6H); 2.50 (m, 5H); 2.34 (t, 4H); 1.87 (m, 3H); 1.48 (dd, 6H); 1.38 (s, 9H); 0.36 (m, 2H); 0.25 (m, 2H).

PREPARATION XLVII 8-cyclopropyl-3-(1-piperazinyl)-8-azabicyclo[3.2.1]octane

In operating analogously to preparation XXIX, starting with the compound obtained according to preparation XLVI, the product sought after is obtained as a white solid (yield=95%).

$^1$H NMR (250 MHz, CDCl3) δ: 3.37 (m, 2H); 2.94 (t, 2H); 2.58 (m, 4H); 2.51 (m, 1H); 1.96 (m, 3H); 1.74 (t, 2H); 1.54 (m, 4H); 0.43 (d, 4H).

PREPARATION XLVIII

4-[1-[(1,1-dimethylethoxy)carbonyl]-4-piperidinyl]-1-piperazinecarboxylic acid, phenylmethyl ester In operating analogously to preparation XXXIV, starting with the t-butyl ester of 4-oxo-1-piperidinecarboxylic acid, the product sought after is obtained as a yellow oil (yield=30%).

$^1$H NMR (250 MHz, DMSO) δ: 7.35 (m, 5H); 5.06 (s, 2H); 3.93 (d, 2H); 3.36 (m, 4H); 2.68 (t, 2H); 2.44 (t, 4H); 2.37 (m, 1H); 1.66 (m, 2H); 1.38 (s, 9H); 1.26 (m, 2H).

PREPARATION IL 4-(4-piperidinyl)-1-piperazinecarboxylic acid, phenylmethyl ester In operating analogously to preparation XXIX, starting with the compound obtained according to preparation XLVIII, the product sought after is obtained as a yellow oil (yield=100%).

$^1$H NMR (250 MHz, DMSO) δ: 8.91 (m broad, h); 8.63 (m broad, 1H); 7.36 (m, 5H); 5.11 (s, 2H); 3.80 (m, 2H); 3.45 (m, 4H); 3.22 (m, 5H); 2.92 (q, 2H); 2.20 (d, 2H); 1.82 (dq, 2H).

PREPARATION L 4-(1-ethyl-4-piperidinyl)-1-piperazinecarboxylic acid, phenylmethyl ester In operating analogously to preparation XXXIV, starting with acetaldehyde and the compound obtained according to preparation IL, the product sought after is obtained as a colourless oil (yield=72%).

$^1$H NMR (250 MHz, DMSO) δ: 7.34 (m, 5H); 5.07 (s, 2H); 3.90 (m, 7H); 3.02 (q, 2H); 2.84 (m, 2H); 2.45 (t, 4H); 1.91 (m, 2H); 1.63 (m, 2H); 1.19 (t, 3H).

PREPARATION LI 1-(1-ethyl-4-piperidinyl)piperazine

In operating analogously to preparation XXXV, starting with the compound obtained according to preparation L, the product sought after is obtained as a yellow oil (yield=71%).

$^1$H NMR (250 MHz, DMSO) δ: 2.90 (m, 6H); 2.52 (m, 4H); 2.30 (q, 2H); 2.17 (tt, 1H); 1.85 (dt, 2H); 1.69 (m, 2H); 1.38 (dq, 2H); 0.97 (t, 3H).

PREPARATION LII

4-[8-[(1,1-dimethylethoxy)carbonyl]-8-azabicyclo[3.2.1]oct-3-yl]-1-piperazinecarboxylic acid, phenylmethyl ester In operating analogously to preparation XXVIII, starting with the t-butyl ester of 3-oxo-8-azabicyclo[3.2.1]octane-8-carboxylic acid, the ester sought after is obtained as a white solid (yield=40%).

$^1$H NMR (250 MHz, CD$_3$CN) δ: 7.33 (m, 5H); 5.07 (s, 2H); 4.13 (m, 2H); 3.37 (t, 4H); 2.80 (hep, 1H); 2.43 (t, 4H); 1.87 (m, 2H); 1.62 (m, 6H); 1.42 (s, 9H).

PREPARATION LIII 4-(8-azabicyclo[3.2.1]oct-3-yl)-1-piperazinecarboxylic acid, phenylmethyl ester, hydrochloride In operating analogously to preparation XLI, starting with the compound obtained according to preparation LII, the product sought after is obtained as a colourless oil (yield=96%).

$^1$H NMR (250 MHz, DMSO) δ: 11.78 (m broad, 1H); 9.45 (s, 2H); 7.38 (m, 5H); 5.11 (s, 3H); 4.09 (m, 4H); 3.95 (m, 1H); 3.43 (m, 4H); 3.07 (m, 2H); 2.22 (m, 4H); 1.92 (m, 4H).

PREPARATION LIV 4-(8-ethyl-8-azabicyclo[3.2.1]oct-3-yl)-1-piperazinecarboxylic acid, phenylmethyl ester In operating analogously to preparation XXXIV, starting with acetaldehyde and the compound obtained according to preparation LIII, the product sought after is obtained as a colourless oil (yield=99%).

$^1$H NMR (250 MHz, CD3CN) δ: 7.33 (m, 5H); 5.07 (s, 2H); 3.39 (m, 6H); 2.63 (m, 1H); 2.56 (q, 2H); 2.42 (t, 4H); 1.93 (m, 2H); 1.61 (m, 6H); 1.06 (t, 3H).

PREPARATION LV 1-(8-ethyl-8-azabicyclo[3.2.1]oct-3-yl)piperazine

In operating analogously to preparation XXXV, starting with the compound obtained according to preparation LIV, the product sought after is obtained as a colourless oil (yield=78%).

$^1$H NMR (300 MHz, CDCl3) δ: 3.57 (m, 2H); 2.94 (t, 2H); 2.71 (q, 2H); 2.59 (m, 4H); 2.52 (m, 1H); 1.99 (m, 4H); 1.64 (m, 4H).

PREPARATION LVI

4-[8-(1-methylethyl)-8-azabicyclo[3.2.1]oct-3-yl]-1-piperazinecarboxylic acid, phenylmethyl ester In operating analogously to preparation XXXIV, starting with acetone and the compound obtained according to preparation LIII, the product sought after is obtained as a colourless oil (yield=77%).

$^1$H NMR (250 MHz, CDCl3) δ: 7.32 (m, 5H); 5.12 (s, 2H); 3.64 (m, 2H); 3.49 (t, 4H); 2.92 (quin, 1H); 2.59 (hep, 1H); 2.47 (m, 4H); 1.99 (m, 2H); 1.82 (dt, 2H); 1.63 (m, 2H); 1.48 (m, 2H); 1.14 (d, 6H).

PREPARATION LVII

1-[8-(1-methylethyl)-8-azabicyclo[3.2.1]oct-3-yl]piperazine

In operating analogously to preparation XXXV, starting with the compound obtained according to preparation LVI, the product sought after is obtained as a colourless oil (yield=82%).

$^1$H NMR (250 MHz, CDCl3) δ: 3.79 (m, 2H); 3.05 (quin, 1H); 2.98 (m, 4H); 2.71 (hep, 1H); 2.61 (m, 4H); 2.13 (m, 2H); 1.95 (m, 2H); 1.65 (m, 4H); 1.29 (d, 6H).

PREPARATION LVIII

Hexahydro-1-methyl-4-(1-oxo-2-propenyl)-1H-1,4-diazepine

A solution is prepared of 20 g (175 mM) of N-methylhomopiperazine in 100 ml of dichloromethane, to which is added, dropwise, at 0° C., a solution of 15.85 g (175 mM) of acryloyl chloride in 20 ml of dichloromethane. The reaction mixture is agitated for 1 hour at 0° C., and then for 2 hours at ambient temperature, and then hydrolysed with a solution of 12 g of sodium carbonate in 20 ml of water. The mixture is decanted, the organic phase is washed once with water and then dried over magnesium sulphate and concentrated under reduced pressure. 23 g of the compound sought after are thus obtained, as an orangy oil, which is used, without other purification, in the next step.

PREPARATION LIX

4-[3-(hexahydro-4-methyl-1H-1,4-diazepin-1-yl)-3-oxopropyl]-1-piperazinecarboxylic acid, phenylmethyl ester A solution is prepared of 7 g (41 mM) of the compound obtained according to preparation LVIII in 100 ml of toluene, to which 11 g (50 mM) of the benzyl ester of 1-piperazinecarboxylic acid are added. The reaction mixture is agitated for 16 hours under reflux of the solvent, and then concentrated under reduced pressure. The residue is taken up into ethyl acetate and the organic phase is washed once with water and then dried over magnesium sulphate and concentrated under reduced pressure. The crude product is purified by silica gel chromatography in eluting with the aid of a toluene/isopropanol/aqueous ammonia mixture (80/20/1; v/v/v). 4.1 g of the compound sought after are thus obtained as a yellow oil (yield=26%).

$^1$H NMR (250 MHz, DMSO) δ: 7.36 (m, 5H); 5.06 (s, 2H); 3.47 (m, 4H); 3.37 (m, 2H); 2.50 (m, 8H); 2.35 (m, 4H); 2.24 and 2.21 (2s, 3H); 1.75 (m, 2H).

PREPARATION LX

1-[3-(hexahydro-4-methyl-1H-1,4-diazepin-1-yl)-3-oxopropyl]piperazine

In operating analogously to preparation XXXV, starting with the compound obtained according to preparation LIX, the product sought after is obtained as a colourless oil (yield=65%).

$^1$H NMR (250 MHz, DMSO) δ: 3.48 (m, 4H); 2.67 (t, 4H); 2.48 (m, 8H); 2.30 (t, 4H); 2.25 and 2.22 (2s, 3H); 1.73 (m, 2H).

PREPARATION LXI

1-[3-(hexahydro-4-methyl-1H-1,4-diazepin-1-yl)propyl]piperazine

A suspension is prepared of 120 mg (3.1 mM) of lithium aluminium hydride in 3 ml of tetrahydrofuran (THF) and a solution of 800 mg (3.1 mM) of the compound obtained according to preparation LX in 10 ml of THF is added. The reaction mixture is heated under gentle reflux of the solvent for 4 hours, and then cooled to ambient temperature. 200 mg of Glauber's salt are added to the reaction mixture and then, after around 15 minutes, 50 ml of ethyl acetate are added. The suspension obtained is filtered and the filtrate is concentrated under reduced pressure. The crude product is purified by silica gel chromatography in eluting with the aid of a dichloromethane/methanol/aqueous ammonia mixture (80/20/10; v/v/v). The product sought after is thus obtained as a colourless oil (yield=34%).

$^1$H NMR (250 MHz, DMSO) δ: 2.64 (t, 4H); 2.57 (m, 4H); 2.49 (m, 4H); 2.38 (t, 2H); 2.23 (m, 6H); 2.21 (s, 3H); 1.66 (quin, 2H); 1.52 (quin, 2H).

PREPARATION LXII

4-[2-(hexahydro-4-methyl-1H-1,4-diazepin-1-yl)-2-oxoethyl]-1-piperazinecarboxylic acid, phenylmethyl ester A solution is prepared of 10 g (87.5 mM) of N-methylhomopiperazine in 200 ml of dichloromethane, to which 36.6 ml of triethylamine are added. The mixture is cooled to −78° C. and 6.97 ml of chloroacetyl chloride are added dropwise. The reaction mixture is agitated for 1.5 hours at −78° C., and a solution of 19.3 g (87.6 mM) of the benzyl ester of 1-piperazinecarboxylic acid in 10 ml of dichloromethane is then added. The mixture is then left to come back to ambient temperature, and agitation is carried out for 15 hours. The medium is then hydrolysed with a solution of sodium carbonate. The mixture is decanted, the organic phase is washed once with water and then dried over magnesium sulphate and concentrated under reduced pressure. The crude product is purified by silica gel chromatography in eluting with the aid of a dichloromethane/methanol/aqueous ammonia mixture (90/10/5; v/v/v). The product sought after is thus obtained as a yellow oil (yield=43%).

$^1$H NMR (250 MHz, DMSO) δ: 7.36 (m, 5H); 5.07 (s, 2H); 3.55 (m, 2H); 3.44 (m, 2H); 3.38 (m, 4H); 3.16 (d, 2H); 2.60 (m, 2H); 2.44 (m, 6H); 2.24 and 2.22 (2s, 3H); 1.76 (m, 2H).

PREPARATION LXIII

1-[2-(hexahydro-4-methyl-1H-1,4-diazepin-1-yl)-2-oxoethyl]piperazine

In operating analogously to preparation XXXV, starting with the compound obtained according to preparation LXII, the product sought after is obtained as a colourless oil (yield=60%).

$^1$H NMR (250 MHz, DMSO) δ: 3.56 (m, 2H); 3.44 (m, 2H); 3.10 (d, 2H); 2.74 (dd, 4H); 2.61 (m, 1H2.44 (m, 4H); 2.39 (m, 3H); 2.25 and 2.22 (2s, 3H); 1.78 (m, 2H).

PREPARATION LXIV

1-[2-(hexahydro-4-methyl-1H-1,4-diazepin-1-yl)ethyl]piperazine

In operating analogously to preparation LXI, starting with the compound obtained according to preparation LXIII, the product sought after is obtained as a yellow oil (yield=21%).

$^1$H NMR (300 MHz, DMSO) δ: 2.63 (m, 8H); 2.49 (m, 5H); 2.28 (m, 7H); 2.21 (s, 3H); 1.66 (quin, 2H).

PREPARATION LXV 1-(1-oxo-2-propenyl)azetidine

In operating analogously to preparation LVIII, starting with azetidine, the product sought after is obtained as a yellow oil which is allowed to react in the following preparation without purification.

PREPARATION LXVI

4-[3-(1-azetidinyl)-3-oxopropyl]-1-piperazinecarboxylic acid, phenylmethyl ester In operating analogously to preparation LIX, starting with the compound obtained according to preparation LXV, the product sought after is obtained as a yellow oil (yield=14%).

$^1$H NMR (250 MHz, DMSO) δ: 7.34 (m, 5H); 5.06 (s, 2H); 4.09 (t, 2H); 3.80 (t, 2H); 3.35 (m, 4H); 2.48 (t, 2H); 2.33 (t, 4H); 2.16 (m, 4H).

PREPARATION LXVII

1-[3-(1-azetidinyl)-3-oxopropyl]piperazine

In operating analogously to preparation XXXV, starting with the compound obtained according to preparation LXVI, the product sought after is obtained as a yellow solid (yield=100%).

M.Pt.=50° C.

PREPARATION LXVIII

1-[3-(1-azetidinyl)propyl]piperazine

In operating analogously to preparation LXI, starting with the compound obtained according to preparation LXVII, the product sought after is obtained as a yellow oil (yield=30%).

$^1$H NMR (300 MHz, DMSO) δ: 3.19 (m broad, 1H); 3.02 (t, 4H); 2.66 (t, 4H); 2.25 (m, 8H); 1.93 (quin, 2H); 1.36 (quin, 2H).

PREPARATION LXIX

α-[(dimethylamino)methyl]-4-piperidinemethanol 20 g (83.6 mM) of 2-[(dimethylamino)methyl]-4-pyridinemethanol dihydrochloride are dissolved in 200 ml of methanol at 50° C. 2 g of platinum oxide are then added under an atmosphere of nitrogen, and the mixture is agitated under an atmosphere of hydrogen, at 50° C., under a pressure of 300 hPa (3 bars), for 7 hours. This catalyst is then removed by filtration and the filtrate is concentrated under reduced pressure. The solid residue is taken up with 10 ml of 10N sodium hydroxide and 150 ml of chloroform. The organic phase is separated and washed with a solution of sodium chloride, dried over magnesium sulphate and concentrated under reduced pressure. The product sought after is thus obtained as an oil which crystallises (yield=87%).

M.Pt.=98° C.

PREPARATION LXX 4-(1-pyrrolidinylmethyl)piperidine

In operating analogously to preparation LXIX, starting with 4-(1-pyrrolidinylmethyl)pyridine, the product sought after is obtained as a yellow oil.

PREPARATION LXXI

4-[(4-(1-methylethyl)-1-piperazinyl]-1-piperidinecarboxylic acid, phenylmethyl ester A mixture is prepared of 827 mg (3.54 mM) of the benzyl ester of 4-oxo-1-piperidinecarboxylic acid, 500 mg (3.9 mM) of N-isopropylpiperazine and 1.2 g (4.25 mM) of titanium isopropoxide in 10 ml of methanol. 148 mg of sodium borohydride are added under agitation and at ambient temperature. The reaction mixture is kept under agitation for 16 hours, and then diluted with 20 ml of water. The suspension obtained is filtered and the precipitate is washed with 30 ml of ethyl acetate which is then used to extract the filtrate. The organic phase obtained is washed with water and then dried over magnesium sulphate and concentrated under reduced pressure. The yellow oil obtained is purified by silica gel chromatography in eluting with the aid of a dichloromethane/methanol mixture (9/1; v/v). 235 mg of the product sought after are thus obtained as a white solid (yield=19%).

M.Pt.=55° C.

PREPARATION LXXII

4-[4-(1-methylethyl)-1-piperazinyl]piperidine

In operating analogously to preparation XXXV, starting with the ester obtained following preparation LXXI, the product sought after is obtained as a white solid (yield=98%).

M.Pt.=65° C.

PREPARATION LXXIII

4-[(4-methyl-1-piperazinyl)methyl]-1-piperidinecarboxylic acid, phenylmethyl ester In operating analogously to preparation LXXI, starting with N-methylpiperazine and the benzyl ester of 4-formyl-1-piperidinecarboxylic acid, the product sought after is obtained as a colourless oil (yield=52%)

¹H NMR (250 MHz, DMSO) δ: 7.34 (m, 5H); 5.05 (s, 2H); 3.98 (m, 2H); 2.77 (m, 2H); 2.29 (m, 8H); 2.19 (s, 3H); 2.08 (d, 2H); 1.67 (m, 3H); 0.95 (m, 2H).

PREPARATION LXXIV

4-[(4-methyl-1-piperazinyl)methyl]piperidine

In operating analogously to preparation XXXV, starting with the ester obtained following preparation LXXIII, the product sought after is obtained as a colourless oil (yield=77%).

¹H NMR (250 MHz, DMSO) δ: 2.89 (m, 2H); 2.51 (m, 2H); 2.28 (m, 8H); 2.12 (s, 3H); 2.05 (d, 2H); 1.55 (m, 3H); 1.02 (m, 2H).

PREPARATION LXXV

4-[(1-azetidinyl)methyl]-1-piperidinecarboxylic acid, phenylmethyl ester

In operating analogously to preparation LXXIII, starting with azetidine, the product sought after is obtained as a colourless oil (yield=69%).

¹H NMR (300 MHz, DMSO) δ: 7.34 (m, 5H); 5.04 (s, 2H); 3.95 (m, 2H); 3.06 (t, 4H); 2.75 (m, 2H); 2.18 (d, 2H); 1.94 (quin, 2H); 1.61 (m, 2H); 1.38 (m, 1H); 0.94 (m, 2H).

PREPARATION LXXVI

4-[(1-azetidinyl)methyl]piperidine

In operating analogously to preparation XXXV, starting with the ester obtained following preparation LXXV, the product sought after is obtained as a colourless oil (yield=93%).

¹H NMR (250 MHz, DMSO) δ: 3.06 (t, 4H); 2.92 (m, 2H); 2.50 (m, 2H); 2.15 (d, 2H); 1.91 (quin, 2H); 1.59 (m, 2H); 1.30 (m, 1H); 1.00 (m, 2H).

PREPARATION LXXVII

4-[(dimethylamino)methyl]-1-piperidinecarboxylic acid, phenylmethyl ester

In operating analogously to preparation LXXIII, starting with dimethylamine, the product sought after is obtained as a colourless oil (yield=78%).

¹H NMR (300 MHz, DMSO) δ: 7.35 (m, 5H); 5.05 (s, 2H); 3.97 (m, 2H); 2.79 (m, 2H); 2.09 (s, 6H); 2.02 (d, 2H); 1.68 (d, 2H); 1.61 (m, 1H); 0.96 (m, 2H).

PREPARATION LXXVIII

4-[(dimethylamino)methyl]piperidine

In operating analogously to preparation XXXV, starting with the ester obtained following preparation LXXVII, the product sought after is obtained as a colourless oil (yield=90%).

¹H NMR (300 MHz, DMSO) δ: 2.91 (m, 2H); 2.43 (m, 2H); 2.08 (s, 6H); 2.01 (d, 2H); 1.59 (m, 2H); 1.49 (m, 1H); 0.96 (dq, 2H).

PREPARATION LXXIX

4-[(4-ethyl-1-piperazinyl)methyl]-1-piperidinecarboxylic acid, 1,1-dimethylethyl ester In operating analogously to preparation LXXIII, starting with N-ethylpiperazine and the t-butyl ester of 4-formyl-1-piperidinecarboxylic acid, the product sought after is obtained as a colourless oil (yield=78%).

¹H NMR (300 MHz, DMSO) δ: 3.90 (m, 2H); 2.67 (m, 2H); 2.29 (m, 10H); 2.09 (d, 2H); 1.63 (m, 3H); 1.38 (s, 9H); 0.96 (t, 3H); 0.85 (m, 2H).

PREPARATION LXXX

4-[(4-ethyl-1-piperazinyl)methyl]piperidine

In operating analogously to preparation XXIX, starting with the ester obtained following preparation LXXIX, the product sought after is obtained as a colourless oil (yield=76%).

¹H NMR (250 MHz, DMSO) δ: 2.95 (m, 2H); 2.51 (m, 2H); 2.42 (m, 10H); 2.05 (d, 2H); 1.54 (m, 3H); 1.03 (m, 2H); 0.99 (t, 3H).

PREPARATION LXXXI

4-[(hexahydro-4-methyl-1H-1,4-diazepin-1-yl)methyl]-1-piperidine-carboxylic acid, 1,1-dimethylethyl ester In operating analogously to preparation LXXIX, starting with N-methyl-homopiperazine, the product sought after is obtained as a colourless oil (yield=83%).

¹H NMR (300 MHz, DMSO) δ: no ¹H NMR

PREPARATION LXXXII

4-[(hexahydro-4-methyl-1H-1,4-diazepin-1-yl)methyl]piperidine

In operating analogously to preparation XXIX, starting with the ester obtained following preparation LXXXI, the product sought after is obtained as a colourless oil (yield=23%).

¹H NMR (250 MHz, DMSO) δ: 3.03 (m, 2H); 2.57 (m, 5H); 2.50 (m, 5H); 2.25 (s, 2H); 2.22 (s, 3H); 1.68 (m, 4H); 1.63 (m, 1H); 1.08 (m, 2H).

PREPARATION LXXXIII 4-(hexahydro-4-methyl-1H-1,4-diazepin-1-yl)-1-piperidinecarboxylic acid, 1,1-dimethylethyl ester In operating analogously to preparation LXXI, starting with N-methyl-homopiperazine and the t-butyl ester of 4-oxo-1-piperidinecarboxylic acid, the product sought after is obtained as a yellow oil (yield=36%).

¹H NMR (250 MHz, CDCl3) δ: 4.15 (m, 2H); 2.82 (m, 4H); 2.70 (m, 7H); 2.42 (s, 3H); 1.87 (m, 2H); 1.98 (m, 2H); 1.45 (s, 9H); 1.40 (m, 2H).

PREPARATION LXXXIV 4-(hexahydro-4-methyl-1H-1,4-diazepin-1-yl)piperidine, trihydrochloride 409 mg (1.37 mM) of the compound obtained according to preparation LXXXIII are dissolved in 1 ml of methanol and 27 ml of a 2.3 N solution of hydrogen chloride in ethyl acetate are added. The mixture is agitated at ambient temperature for 12 hours and then concentrated under reduced pressure. The product sought after is thus obtained as a beige foam (yield=99%).
$^1$H NMR (250 MHz, DMSO) δ: 3.88 (m, 4H); 3.62 (m, 1H); 3.43 (m, 6H); 2.94 (m, 2H); 2.82 (s, 3H); 2.31 (m, 4H); 2.10 (m, 2H).

PREPARATION LXXXV 4-(4-cyclopropyl-1-piperazinyl)-1-piperidinecarboxylic acid, phenylmethyl ester In operating analogously to preparation LXXI, starting with N-cyclopropylpiperazine, the product sought after is obtained as a white solid (yield=62%).
M.Pt.=64° C.

PREPARATION LXXXVI 4-(4-cyclopropyl-1-piperazinyl)piperidine

In operating analogously to preparation LXXII, starting with the ester obtained following preparation LXXXV, the product sought after is obtained as a white solid (yield=90%).
M.Pt.=107° C.

PREPARATION LXXXVII

4-[4-(1,1-dimethylethyl)-1-piperazinyl]-1-piperidinecarboxylic acid, phenylmethyl ester In operating analogously to preparation LXXI, starting with N-t-butylpiperazine, the product sought after is obtained as a white solid (yield=50%).
M.Pt.=84° C.

PREPARATION LXXXVIII

4-[4-(1,1-dimethylethyl)-1-piperazinyl]piperidine

In operating analogously to preparation LXXII, starting with the ester obtained following preparation LXXXVII, the product sought after is obtained as a white solid (yield=75%).
M.Pt.=82° C.

PREPARATION LXXXIX 4-(4-piperidinyl)-1-piperidinecarboxylic acid, 1,1-dimethylethyl ester A solution is prepared of 41 g (0.17 M) of 4,4'-bipiperidine dihydrochloride in 250 ml of ethanol and 250 ml of 2N sodium hydroxide. A solution of 18.5 g (0.085 M) of t-butyl dicarbonate in 100 ml of ethanol are added slowly, at 0° C. The reaction mixture is agitated for 1 hour at 10° C. and the ethanol is then removed by an evaporator, under reduced pressure. The residual aqueous phase is saturated with sodium chloride and extracted with ethyl acetate. The organic phase obtained is dried over magnesium sulphate and concentrated under reduced pressure. The crude product is purified by silica gel chromatography in eluting with the aid of a dichloromehane/methanol/aqueous ammonia mixture (8/2/0.4; v/v/v). 16.5 g of the compound sought after are thus obtained as a white solid (yield=72%).
M.Pt.=70-71° C.

PREPARATION XC 4-(1-ethyl-4-piperidinyl)-1-piperidinecarboxylic acid, 1,1-dimethylethyl ester In operating analogously to preparation LXXI, starting with the ester obtained following preparation LXXXIX and acetaldehyde, the product sought after is obtained as a white solid (yield=87%).
M.Pt.=68-70° C.

PREPARATION XCI 4-(1-ethyl-4-piperidinyl)piperidine, dihydrochloride

In operating analogously to preparation LXXXIV, starting with the ester obtained following preparation XC, the product sought after is obtained as a white solid (yield=100%).
M.Pt.=280° C.

PREPARATION XCII

4-[1-(1-methylethyl)-4-piperidinyl]-1-piperidinecarboxylic acid, 1,1-dimethylethyl ester In operating analogously to preparation XC, starting with the ester obtained following preparation LXXXIX and acetone, the product sought after is obtained as a colourless oil (yield=69%).
$^1$H NMR (250 MHz, CDCl3) δ: 4.10 (m, 2H); 3.52 (m, 1H); 3.47 (m, 2H); 2.55 (m, 4H); 1.88 (m, 4H); 1.85 (m, 4H); 1.45 (s, 9H); 1.30 (d, 6H); 1.12 (m, 2H).

PREPARATION XCIII

4-[1-(1-methylethyl)-4-piperidinyl]piperidine, dihydrochloride

In operating analogously to preparation LXXXIV, starting with the ester obtained following preparation XCII, the product sought after is obtained as a white solid (yield=89%).
M.Pt.=250° C.

PREPARATION XCIV 4-(1-cyclopropyl-4-piperidinyl)-1-piperidinecarboxylic acid, 1,1-dimethylethyl ester 150 mg (0.56 mM) of the compound obtained according to preparation LXXXIX are dissolved in 5 ml of methanol and 320 µl of acetic acid and 200 mg of 3 Å molecular sieves, and then 562 µl (2.79 mM) of 1-ethoxy-1-(trimethylsilyloxy)cyclopropane and 141 mg (2.23 mM) of sodium borohydride, are added. The reaction mixture is heated under gentle reflux for 20 hours, and then cooled and filtered. The filtrate is concentrated under reduced pressure and the residue from evaporation is taken up into 20 ml of ethyl acetate. This organic phase is washed with a 2N solution of sodium hydroxide, and then with a saturated solution of sodium chloride, dried over magnesium sulphate and concentrated under reduced pressure. The crude product is purified by silica gel chromatography in eluting with the aid of a dichloromehane/methanol mixture (95/5; v/v). 110 mg of the compound sought after are thus obtained as a white powder (yield=64%).

$^1$H NMR (250 MHz, CDCl3) δ: 4.10 (m, 2H); 3.05 (m, 4H); 2.65 (t, 2H); 2.09 (t, 2H); 1.67 (m, 4H); 1.55 (m, 1H); 1.45 (s, 9H); 1.22 (m, 6H); 0.47 (m, 4H).

PREPARATION XCV

4-(1-cyclopropyl-4-piperidinyl)piperidine, dihydrochloride

In operating analogously to preparation LXXXIV, starting with the ester obtained following preparation XCIV, the product sought after is obtained as a white paste (yield=99%).

$^1$H NMR (250 MHz, DMSO) δ: 10.50 (m broad, 1H); 8.80 (m broad, 2H); 3.45 (m, 2H); 3.16 (m, 2H); 2.81 (m, 2H); 2.73 (m, 3H); 1.90 (m, 4H); 1.60 (m, 2H); 1.35 (m, 4H); 1.10 (m, 2H); 0.78 (m, 2H).

PREPARATION XCVI

4-[2-(4-piperidinyl)ethyl]-1-piperidinecarboxylic acid, 1,1-dimethylethyl ester In operating analogously to preparation LXXXIX, starting with 4,4'-ethylenedipiperidine hydrochloride, the product sought after is obtained as a white solid (yield=39%).
M.Pt.=92–94° C.

PREPARATION XCVII

4-[2-(1-methyl-4-piperidinyl)ethyl]piperidine

A solution is prepared of 307 mg (1.04 mM) of the ester obtained following preparation XCVI in 20 ml of anhydrous tetrahydrofuran (THF) and 157 mg (4.14 mM) of lithium aluminium hydride are added portionwise. The reaction mixture is agitated for 10 hours at 70° C. and then cooled and diluted with 30 ml of THF. 200 mg of Glauber's salt are added and the mixture is left under agitation at ambient temperature overnight, and then filtered. The filtrate is concentrated under reduced pressure to give 235 mg of the product sought after as a white paste (yield=99%).

$^1$H NMR (300 MHz, DMSO) δ: 3.16 (s, 2H); 2.80 (m, 2H); 2.70 (m, 2H); 2.38 (t, 2H); 2.10 (s, 3H); 1.76 (m, 2H); 1.58 (m, 3H); 1.42 (m, 1H); 1.11 (m, 8H); 0.94 (m, 2H).

PREPARATION XCVIII

4-[2-(4-methyl-1-piperazinyl)ethyl]pyridine

In a tube, 2 ml (19 mM) of 4-vinylpyridine, 3.16 ml (28.5 mM) of N-methylpiperazine, and 200 μl of acetic acid are mixed in 12 ml of ethanol. The tube is closed and heated for 10 minutes at 160° C. in a microwave oven. After cooling, 20 ml of 0.5N sodium hydroxide are added slowly and the mixture is extracted with dichloromethane. The separated organic phase is dried over magnesium sulphate and concentrated under reduced pressure. The product sought after is thus obtained as a yellow oil (yield=86%).

$^1$H NMR (250 MHz, DMSO) δ: 8.43 (dd, 2H); 7.25 (dd, 2H); 2.73 (t, 2H); 2.52 (m, 2H); 2.48 (m, 4H); 2.30 (m, 4H); 2.13 (s, 3H).

In operating analogously to preparation XCVIII, the following pyridine derivatives are obtained:

PREPARATION IC

4-[2-(1-piperidinyl)ethyl]pyridine yellow oil (yield=52%)
$^1$H NMR (250 MHz, DMSO) δ: 8.43 (dd, 2H); 7.24 (dd, 2H); 2.73 (t, 2H); 2.49 (m, 2H); 2.37 (t, 2H); 1.43 (m, 6H).

PREPARATION C

4-[2-[(methyl)(1-methylethyl)amino]ethyl]pyridine yellow oil (yield=10%).
$^1$H NMR (250 MHz, DMSO) δ: 8.49 (d, 2H); 7.16 (d, 2H); 2.76 (hep, 1H); 2.65 (t, 2H); 2.56 (d, 2H); 2.15 (s, 3H); 0.90 (d, 6H).

PREPARATION CI

4-[2-(4-morpholinyl)ethyl]pyridine yellow oil (yield=72%).
$^1$H NMR (250 MHz, DMSO) δ: 8.44 (dd, 2H); 7.26 (dd, 2H); 3.05 (dd, 4H); 2.75 (t, 2H); 2.53 (m, 2H); 2.41 (dd, 2H).

PREPARATION CII

4-[2-(1-azetidinyl)ethyl]pyridine yellow oil (yield=62%).
$^1$H NMR (300 MHz, DMSO) δ: 8.43 (d, 2H); 7.22 (d, 2H); 3.07 (t, 4H); 2.53 (m, 4H); 1.91 (quin, 2H).

PREPARATION CIII

(Methyl)[2-(4-pyridinyl)ethyl]carbamic acid, 1,1-dimethylethyl ester yellow oil (yield=83%).
$^1$H NMR (300 MHz, DMSO) δ: 8.45 (d, 2H); 7.21 (d, 2H); 3.42 (t, 2H); 2.76 (t, 2H); 2.75 (s, 3H); 1.23 (s, 9H).

PREPARATION CIV

4-[2-[(methyl)(ethyl)amino]ethyl]pyridine colourless oil (yield=51%).
$^1$H NMR (300 MHz, DMSO) δ: 8.50 (d, 2H); 7.25 (d, 2H); 2.73 (t, 2H); 2.55 (t, 2H); 2.43 (q, 2H); 2.23 (s, 3H); 0.90 (t; 3H).

PREPARATION CV

4-[2-(diethylamino)ethyl]pyridine yellow oil (yield=30%).
$^1$H NMR (250 MHz, DMSO) δ: 8.43 (dd, 2H); 7.24 (dd, 2H); 2.65 (m, 4H); 2.40 (q, 4H); 0.93 (t, 6H).

PREPARATION CVI

4-[2-(hexahydro-4-methyl-1H-1,4-diazepin-1-yl)ethyl]pyridine yellow oil (yield=52%)
$^1$H NMR (250 MHz, DMSO) δ: 8.43 (d, 2H); 7.25 (d, 2H); 2.71 (m, 8H); 2.50 (m, 4H); 2.22 (s, 3H); 1.68 (m, 2H).

PREPARATION CVII

4-[2-(4-methyl-1-piperazinyl)ethyl]piperidine

In operating analogously to preparation LXIX, starting with the compound obtained according to preparation XCVIII, the product sought after is obtained as a yellow solid (yield=80%).
M.Pt.=111-112° C.

PREPARATION CVIII

4-[2-(dimethylamino)ethyl]piperidine

In operating analogously to preparation CVII, starting with 4-[2-(dimethylamino)ethyl]pyridine, the product sought after is obtained as a colourless oil (yield=96%).
$^1$H NMR (300 MHz, DMSO) δ: 2.86 (2H); 2.39 (dt, 2H); 2.18 (dd, 2H); 2.08 (s, 6H); 1.54 (dm, 2H); 1.27 (m, 3H); 0.96 (m, 2H).

PREPARATION CIX

4-[2-(1-pyrrolidinyl)ethyl]piperidine

In operating analogously to preparation CVII, starting with 4-[2-(1-pyrrolidinyl)ethyl]pyridine, the product sought after is obtained as a colourless oil (yield=88%).
$^1$H NMR (300 MHz, DMSO) δ: 2.86 (dm, 2H); 2.38 (m, 8H); 1.64 (m, 4H); 1.54 (dm, 2H); 1.32 (m, 3H); 0.96 (dq, 2H).

In operating analogously to preparation CVII, starting with the compounds obtained according to preparations IC to CVI, the following piperidine derivatives are obtained

PREPARATION CX

4-[2-(1-piperidinyl)ethyl]piperidine yellow oil (yield=92%). $^1$H NMR (300 MHz, DMSO) δ: 3.10 (dm, 2H); 2.67 (dt, 2H); 2.27 (m, 6H); 1.70 (m, 2H); 1.47 (m, 5H); 1.35 (m, 4H); 1.23 (m, 2H).

PREPARATION CXI

4-[2-[(methyl)(1-methylethyl)amino]ethyl]piperidine yellow oil (yield=96%).
$^1$H NMR (250 MHz, DMSO) δ: 3.10 (d, 2H); 2.77 (m, 1H); 2.60 (m, 2H); 2.35 (t, 2H); 2.10 (s, 3H); 1.72 (m, 2H); 1.34 (m, 1H); 1.29 (t, 2H); 1.23 (m, 2H); 0.91 (d, 6H).

PREPARATION CXII

4-[2-(4-morpholinyl)ethyl]piperidine colourless oil (yield=98%).
$^1$H NMR (300 MHz, DMSO) δ: 3.54 (t, 4H); 2.86 (dt, 2H); 2.39 (dt, 2H); 2.28 (m, 4H); 2.25 (t, 2H); 1.54 (dm, 2H); 1.31 (m, 3H); 0.97 (m, 2H).

PREPARATION CXIII

4-[2-(1-azetidinyl)ethyl]piperidine colourless oil (yield=74%).
$^1$H NMR (250 MHz, DMSO) δ: 3.16 (t, 4H); 3.12 (m, 2H); 2.65 (m, 2H); 2.35 (t, 2H); 1.94 (quin, 2H); 1.85 (m, 2H); 1.35 (m, 1H); 1.23 (t, 2H); 1.15 (m, 2H).

PREPARATION CXIV (Methyl)[2-(4-piperidinyl)ethyl]carbamic acid, 1,1-dimethylethyl ester colourless oil (yield=64%).
$^1$H NMR (300 MHz, DMSO) δ: 3.16 (t, 2H); 2.89 (dm, 2H); 2.73 (s, 3H); 2.40 (t, 2H); 1.38 (s, 9H); 1.35 (m, 2H); 0.96 (m, 2H).

PREPARATION CXV

4-[2-[(methyl)(ethyl)amino]ethyl]piperidine colourless oil (yield=98%).
$^1$H NMR (300 MHz, DMSO) δ: 3.13 (m, 2H); 2.68 (m, 2H); 2.32 (m, 4H); 2.11 (s, 3H); 1.85 (m, 2H); 1.51 (m, 1H); 1.34 (t, 2H); 1.24 (m, 2H); 0.96 (t, 3H).

PREPARATION CXVI

4-[2-(diethylamino)ethyl]piperidine yellow oil (yield=87%).
$^1$H NMR (250 MHz, DMSO) δ: 2.87 (dm, 2H); 2.40 (m, 8H); 1.54 (dm, 2H); 1.26 (m, 3H); 0.98 (m, 2H); 0.91 (t, 6H).

PREPARATION CXVII

4-[2-(hexahydro-4-methyl-1H-1,4-diazepin-1-yl)ethyl]-piperidine yellow oil (yield=79%).
$^1$H NMR (300 MHz, DMSO) δ: 2.89 (d, 2H); 3.05 (m, 2H); 2.58 (m, 4H); 2.49 (m, 4H); 2.46 (m, 4H); 2.21 (s, 3H); 1.66 (m, 2H); 1.64 (m, 2H); 1.28 (m, 3H); 0.99 (m, 2H).

PREPARATION CXVIII 4-(2-hydroxy-1,1-dimethylethyl)-1-piperidinecarboxylic acid, 1,1-dimethylethyl ester In operating analogously to preparation LXXXIX, starting with β,β-dimethyl-4-piperidineethanol, the product sought after is obtained as a colourless oil (yield=96%).
$^1$H NMR (300 MHz, DMSO) δ: 4.41 (t, 1H); 3.98 (d, 2H); 3.13 (d, 2H); 2.51 (m, 2H); 1.50 (d, 2H); 1.38 (s, 9H); 1.33 (m, 1H); 1.04 (m, 2H); 0.93 (s, 6H.

PREPARATION CXIX 4-(1,1-dimethyl-2-oxoethyl)-1-piperidinecarboxylic acid, 1,1-dimethylethyl ester A solution is prepared of 68 µl (0.77 mM) of oxalyl chloride in 6 ml of anhydrous dichloromethane. 82.5 µl of dimethylsulphoxide are added at −70° C., and then, after 15 min, 100 mg (0.39 mM) of the alcohol obtained according to preparation CXVIII in solution in 4 ml of dichloromethane are added. Then, after 5 min, 270 µl of triethylamine are added. The mixture is agitated 5 minutes at −70° C., and then left to come back to ambient temperature. After addition of 25 ml of ethyl acetate, this organic phase is washed with a 10% sodium bicarbonate solution, dried over magnesium sulphate and concentrated under reduced pressure. The crude product is purified by silica gel chromatography in eluting with the aid of a dichloromethane/ethyl acetate mixture (85/15; v/v). 80 mg of the compound sought after are thus obtained as a colourless oil (yield=80%).

$^1$H NMR (250 MHz, DMSO) δ: 9.44 (s, 1H); 3.96 (d, 2H); 2.59 (m, 2H); 1.69 (m, 1H); 1.50 (m, 2H); 1.38 (s, 9H); 1.07 (m, 2H); 0.93 (s, 6H).

PREPARATION CXX

4-[2-(1-azetidinyl)-1,1-dimethylethyl]-1-piperidinecarboxylic acid, 1,1-dimethylethyl ester In operating analogously to preparation LXXI, starting with the compound obtained according to preparation CXIX and azetidine, the product sought after is obtained as a colourless oil (yield=65%).

$^1$H NMR (300 MHz, DMSO) δ: 3.96 (d, 2H); 3.13 (t, 4H); 2.51 (m, 2H); 2.16 (s, 2H); 1.92 (quin, 2H); 1.55 (d, 2H); 1.39 (s, 9H); 1.35 (m, 1H); 1.05 (m, 2H); 0.70 (s, 6H).

PREPARATION CXXI

4-[2-(1-azetidinyl)-1,1-dimethylethyl]piperidine, bis(trifluoroacetate)

520 mg (1.75 mM) of the compound obtained according to preparation CXX are mixed with 3 ml of trifluoroacetic acid and 380 µl of anisole in 3 ml of dichloromethane. The mixture is agitated overnight at ambient temperature and then concentrated under reduced pressure. The residue is taken up into 20 ml of toluene and again concentrated under reduced pressure. The crude product is triturated in 4 ml of ethyl ether to give a solid which is separated off by filtration and dried. 683 mg of the compound sought after are thus obtained (yield=92%).

M.Pt.=138-140° C.

PREPARATION CXXXII

4-[2-(4-morpholinyl)-1,1-dimethylethyl]-1-piperidinecarboxylic acid, 1,1-dimethylethyl ester In operating analogously to preparation CXX, starting with morpholine, the product sought after is obtained as a colourless oil (yield=12%).

$^1$H NMR (300 MHz, DMSO) δ: 3.97 (d, 2H); 3.53 (t, 4H); 2.57 (m, 2H); 2.41 (t, 4H); 2.10 (s, 2H); 1.60 (d, 2H); 1.38 (s, 9H); 1.29 (m, 1H); 1.05 (m, 2H); 0.77 (s, 6H).

PREPARATION CXXIII

4-[2-(4-morpholinyl)-1,1-dimethylethyl]piperidine, bis(trifluoroacetate)

In operating analogously to preparation CXXI, starting with the compound obtained according to preparation CXXII, the product sought after is obtained as a pale yellow solid (yield=69%).

M.Pt.=158-160° C.

PREPARATION CXXIV

4-[2-(1-piperidinyl)-1,1-dimethylethyl]pyridine

A suspension of 70 g (0.58 M) of 4-isopropylpyridine, 250 g (2 M) of piperidine hydrochloride and 85 g of paraformaldehyde in 600 ml of 95% ethanol is held under reflux for 48 hours. The reaction mixture is then concentrated under reduced pressure and the residue is taken up with 650 ml of 3N sodium hydroxide and extracted with thrice 250 ml of ethyl acetate. The combined organic phases are washed with a solution of sodium chloride, dried and concentrated under reduced pressure. The crude product is distilled under a vacuum of 1 mm Hg and the fraction collected between 80 and 125° C. is purified by silica gel chromatography in eluting with the aid of a toluene/isopropanol mixture (9/1; v/v). 21.4 g of the compound sought after are thus obtained as a clear yellow oil (yield=17%).

$^1$H NMR (300 MHz, CDCl3) δ: 8.49 (d, 2H); 7.32 (d, 2H); 2.53 (s, 2H); 2.20 (t, 4H); 1.39 (m, 4H); 1.36 (m, 2H); 1.29 (s, 6H),

PREPARATION CXXV

4-[2-(1-piperidinyl)-1,1-dimethylethyl]piperidine

In operating analogously to preparation CVII, starting with the compound obtained according to preparation CXXIV, the product sought after is obtained as a yellow oil (yield=33%).

$^1$H NMR (300 MHz, DMSO) δ: 2.94 (dm, 2H); 2.37 (m, 6H); 2.03 (s, 2H); 1.45 (m, 6H); 1.32 (m, 2H); 1.18 (m, 1H); 1.05 (m, 2H); 0.74 (s, 6H).

In operating analogously to the preparations CXXIV and CXXV, the two following compounds are obtained:

PREPARATION CXXVI

4-[2-(1-pyrrolidinyl)-11,1-dimethylethyl]piperidine yellow oil (yield=72%).

$^1$H NMR (250 MHz, DMSO) δ: 2.97 (d, 2H); 2.55 (m, 4H); 2.48 (m, 2H); 2.26 (s, 2H); 1.66 (m, 4H); 1.62 (d, 2H); 1.29 (m, 1H); 1.03 (m, 2H); 0.77 (s, 6H).

PREPARATION CXXVII

4-[2-(diethylamino)-1,1-dimethylethyl]piperidine colourless oil (yield=79%).

$^1$H NMR (300 MHz, DMSO) δ: no $^1$H NMR

PREPARATION CXXVIII

N,1-dimethyl-N-[1-(phenylmethyl)-4-piperidinyl]-4-piperidinamine

In operating analogously to preparation LXXI, starting with N-methyl-4-piperidinone and 1-benzyl-4-(methylamino)piperidine, the product sought after is obtained as a yellow oil (yield=66%).

$^1$H NMR (300 MHz, DMSO) δ: 7.28 (m, 5H); 3.41 (s, 2H); 2.76 (m, 4H); 2.40 (m, 2H); 2.12 (s, 3H); 2.10 (s, 3H); 1.90 (dt, 2H); 1.81 (dt, 2H); 1.57 (dm, 4H); 1.44 (m, 4H).

PREPARATION CXXIX

N,1-dimethyl-N-(4-piperidinyl)-4-piperidinamine

A solution is prepared of 980 mg (3.25 mM) of the compound obtained according to preparation CXXVIII in 60 ml of methanol and 150 mg of 10% palladium on carbon are added. The mixture is agitated under an atmosphere of hydrogen, under a pressure of 50 PSI (3.5 bars or 3450 hPa), at ambient temperature for 10 hours. The catalyst is removed by filtration and the filtrate is concentrated under reduced pressure. The crude product obtained is purified by silica gel chromatography in eluting with the aid of a dichloromethane/methanol/aqueous ammonia mixture (97/3/0.3; v/v/v). The product sought after is obtained as a yellow oil (yield=29%).

$^1$H NMR (250 MHz, DMSO) δ: 2.94 (d, 2H); 2.76 (d, 2H); 2.43 (m, 4H); 2.12 (s, 3H); 2.10 (s, 3H); 1.81 (m, 2H); 1.76 (m, 4H); 1.45 (m, 2H); 1.30 (m, 2H).

PREPARATION CXXX

4-[2-oxo-2-(4-methyl-1-piperazinyl)ethyl]pyridine

A solution is prepared of 3 g (17.3 mM) of (4-pyridinyl) acetic acid in 50 ml of tetrahydrofuran (THF) and, at ambient temperature, a solution of 3.4 g (20.7 mM) of carbonyldiimidazole in solution in 50 ml of THF, is added dropwise. The reaction mixture is agitated for 8 hours, and a solution of 1.73 g (17.3 mM) of N-methylpiperazine in 20 ml of THF is then added. The reaction mixture is heated under reflux of the solvent for 2 hours, and then concentrated under reduced pressure. The residue from evaporation is taken up with 80 ml of 3N sodium hydroxide and extracted with ethyl acetate. The organic phase is dried over magnesium sulphate and concentrated under reduced pressure. The crude product is purified by silica gel chromatography in eluting with the aid of a dichloromethane/methanol mixture (99/1; v/v). The product sought after is obtained as a colourless oil (yield=28%).

$^1$H NMR (250 MHz, DMSO) δ: 8.47 (dd, 2H); 7.23 (dd, 2H); 3.75 (s, 2H); 3.46 (t, 2H); 2.23 (t, 4H); 2.15 (3H),

PREPARATION CXXXI

4-[2-oxo-2-(4-methyl-1-piperazinyl)ethyl]piperidine

In operating analogously to preparation CVII, starting with the compound obtained according to preparation CXXX, the product sought after is obtained as a colourless oil (yield=59%).

$^1$H NMR (250 MHz, DMSO) δ: 3.42 (t, 4H); 3.28 (m, 2H); 2.87 (dt, 2H); 2.41 (dt, 2H); 2.24 (m, 6H); 2.16 (s, 3H); 1.71 (m, 1H); 1.54 (dm, 2H); 1.06 (dq, 2H).

In operating analogously to Examples 3 and 4, starting with the acids and amines obtained above (or from amines known from the literature), the following compounds according to the invention are obtained:

EXAMPLE 16

N-[2-[2-[4-[3-(1-azetidinyl)propyl]-1-piperazinyl]-2-oxo-ethoxy]ethyl]-4-methoxy-N,2,6-trimethylbenzenesulphonamide, difumarate Beige solid (yield=34%).
M.Pt.=82° C.

EXAMPLE 17

N-[2-[2-[4-(1-methyl-3-piperidinyl)-1-piperazinyl]-2-oxo-ethoxy]ethyl]-4-methoxy-N,2,6-trimethylbenzenesulphonamide, difumarate White solid (yield=36%).
M.Pt.=60-65° C.

EXAMPLE 18

N-[2-[2-[4-(1-methyl-4-piperidinyl)-1-piperazinyl]-2-oxo-ethoxy]ethyl]-4-methoxy-N-cyclopropyl-2,6-dimethylbenzenesulphonamide, difumarate White solid (yield=51%).
M.Pt.=185° C.

EXAMPLE 19

N-[2-[2-[4-[2-(1-pyrrolidinyl)ethyl]-1-piperazinyl]-2-oxo-ethoxy]ethyl]-4-methoxy-N-cyclopropyl-2,6-dimethylbenzenesulphonamide, difumarate White solid (yield=42%).
M.Pt.=141° C.

EXAMPLE 20

N-[2-[2-[4-[(1-methyl-2-imidazolyl)methyl]-1-piperazinyl]-2-oxo-ethoxy]ethyl]-4-methoxy-N,2,6-trimethylbenzenesulphonamide, difumarate White solid (yield=45%).
M.Pt.=60-65° C.

EXAMPLE 21

N-[2-[2-[4-(1-methyl-4-piperidinyl)-1-piperazinyl]-2-oxo-ethoxy]ethyl]-4-methoxy-N-ethyl-2,6-dimethylbenzenesulphonamide, difumarate White solid (yield=48%).
M.Pt.=206° C.

EXAMPLE 22

N-[2-[2-[4-[3-(dimethylamino)propyl]-1-piperazinyl]-2-oxo-ethoxy]ethyl]-4-methoxy-N-ethyl-2,6-dimethylbenzenesulphonamide, difumarate White solid (yield=26%)
M.Pt.=60° C. .

EXAMPLE 23

N-[2-[2-[4-(9-methyl-9-azabicyclo[3.3.1]non-3-yl)-1-piperazinyl]-2-oxo-ethoxy]ethyl]-4-methoxy-N,2,6-trimethylbenzenesulphonamide, fumarate White solid (yield=73%).
M.Pt.=96° C.

EXAMPLE 24

N-[2-[2-[4-[3-(1-pyrrolidinyl)propyl]-piperazinyl]-2-oxo-ethoxy]ethyl]-4-methoxy-N-ethyl-2,6-dimethyl-benzenesulphonamide, difumarate White solid (yield=63%).
M.Pt.=65° C.

EXAMPLE 25

N-[2-[2-[4-[3-(1-pyrrolidinyl)propyl]-1-piperazinyl]-2-oxo-ethoxy]ethyl]-4-methoxy-N-cyclopropyl-2,6-dimethylbenzenesulphonamide, difumarate Ecru solid (yield=61%).
M.Pt.=55° C.

EXAMPLE 26

N-[2-[2-[4-(8-cyclopropyl-8-azabicyclo[3.2.1]oct-3-yl)-1-piperazinyl]-2-oxo-ethoxy]ethyl]-4-methoxy-N,2,6-trimethylbenzenesulphonamide, fumarate White solid (yield=81%).
M.Pt.=75° C.

EXAMPLE 27

N-[2-[2-[4-(8-methyl-8-azabicyclo[3.2.1]oct-3-yl)-1-piperazinyl]-2-oxo-ethoxy]ethyl]-4-methoxy-N-ethyl-2,6-dimethylbenzenesulphonamide, difumarate White solid (yield=64%).
M.Pt.=185° C.

EXAMPLE 28

N-[2-[2-[4-(8-methyl-8-azabicyclo[3.2.1]oct-3-yl)-1-piperazinyl]-2-oxo-ethoxy]ethyl]-4-methoxy-N-cyclopropyl-2,6-dimethylbenzenesulphonamide, difumarate White solid (yield=51%).
M.Pt.=160° C.

EXAMPLE 29

N-[2-[2-[4-(1-cyclopropyl-4-piperidinyl)-1-piperazinyl]-2-oxo-ethoxy]ethyl]-4-methoxy-N,2,6-trimethylbenzenesulphonamide, difumarate White solid (yield=60%).
M.Pt.=112-114° C.

EXAMPLE 30

N-[2-[2-[4-(8-methyl-8-azabicyclo[3.2.1]oct-3-yl)-1-piperazinyl]-2-oxo-ethoxy]ethyl]-4-methoxy-N-(1-methylethyl)-2,6-dimethylbenzenesulphonamide, difumarate White solid (yield=60%).
M.Pt.=168° C.

EXAMPLE 31

N-[2-[2-[4-(1-ethyl-4-piperidinyl)-1-piperazinyl]-2-oxo-ethoxy]ethyl]-4-methoxy-N,2,6-trimethylbenzenesulphonamide, fumarate Beige solid (yield=48%).
$^1$H NMR (250 MHz, DMSO) δ: 6.80 (s, 2H); 6.53 (s, 2H); 4.05 (s, 2H); 3.80 (s, 3H); 3.53 (t, 2H); 3.39 (m, 2H); 3.29 (m, 2H); 3.22 (t, 2H); 3.12 (m, 2H); 2.70 (s, 3H); 2.62 (q, 2H); 2.53 (s, 6H); 2.48 (m, 4H); 2.29 (m, 3H); 1.77 (m, 2H); 1.52 (m, 2H); 1.07 (t, 2H).

EXAMPLE 32

N-[2-[2-[4-[1-(1,1-dimethylethyl)-4-piperidinyl]-1-piperazinyl]-2-oxo-ethoxy]ethyl]-4-methoxy-N,2,6-trimethylbenzenesulphonamide, difumarate White solid (yield=41%).
M.Pt.=230° C.

EXAMPLE 33

N-[2-[2-[4-[(1-methyl-4-piperidinyl)methyl]-1-piperazinyl]-2-oxo-ethoxy]ethyl]-4-methoxy-N,2,6-trimethylbenzenesulphonamide, fumarate Yellow solid (yield=62%).
M.Pt.=50° C.

EXAMPLE 34

N-[2-[2-[4-[3-(dimethylamino)propyl]-1-piperazinyl]-2-oxo-ethoxy]ethyl]-2,6-dichloro-4-methoxy-N-methyl-benzenesulphonamide, difumarate White solid (yield=78%).
M.Pt.=60° C.

EXAMPLE 35

N-[2-[2-[4-(1-methyl-4-piperidinyl)-1-piperazinyl]-2-oxo-ethoxy]ethyl]-2,6-dichloro-4-methoxy-N-methyl-benzenesulphonamide, difumarate White solid (yield=69%).
M.Pt.=125° C.

EXAMPLE 36

N-[2-[2-[4-[2-(1-methyl-4-piperidinyl)ethyl]-1-piperazinyl]-2-oxo-ethoxy]ethyl]-4-methoxy-N,2,6-trimethylbenzenesulphonamide, difumarate Ecru solid (yield=62%).
M.Pt.=90° C.

EXAMPLE 37

N-[2-[2-[4-(1-methyl-4-piperidinyl)hexahydro-1H-1,4-diazepin-1-yl]-2-oxo-ethoxy]ethyl]-4-methoxy-N,2,6-trimethylbenzenesulphonamide, fumarate White solid (yield=56%).
M.Pt.=53° C.

EXAMPLE 38

N-[2-[2-[4-(1-methyl-4-piperidinyl)-1-piperazinyl]-2-oxo-ethoxy]ethyl]-4-methoxy-N-(1-methylethyl)-2,6-dimethylbenzenesulphonamide, difumarate White solid (yield=41%).
M.Pt.=170° C.

EXAMPLE 39

N-[2-[2-[4-[1-(1-methylethyl)-4-piperidinyl]-1-piperazinyl]-2-oxo-ethoxy]ethyl]-4-methoxy-N,2,6-trimethylbenzenesulphonamide, fumarate White solid (yield=81%).
M.Pt.=130° C.

EXAMPLE 40

N-[2-[2-[4-[3-(1-piperidinyl)propyl]-1-piperazinyl]-2-oxo-ethoxy]ethyl]-4-methoxy-N-ethyl-2,6-dimethylbenzenesulphonamide, difumarate Ecru solid (yield=60%).
M.Pt.=65° C.

EXAMPLE 41

N-[2-[2-[4-(1-methyl-4-piperidinyl)-1-piperazinyl]-2-oxo-ethoxy]ethyl]-2,4-dichloro-6-methoxy-N-methyl-benzenesulphonamide, difumarate White solid (yield=46%).
M.Pt.=202° C.

EXAMPLE 42

N-[2-[2-[4-(1-ethyl-4-piperidinyl)-1-piperazinyl]-2-oxo-ethoxy]ethyl]-2,6-dichloro-4-methoxy-N-methyl-benzenesulphonamide, fumarate White solid (yield=68%).
M.Pt.=96-98° C.

EXAMPLE 43

N-[2-[2-[4-((3S)-1-azabicyclo[2.2.2]oct-3-yl)-1-piperazinyl]-2-oxo-ethoxy]ethyl]-4-methoxy-N-methyl-2,6-dichlorobenzenesulphonamide, fumarate White solid (yield=36%).
M.Pt.=75-79° C.

In operating analogously to Example 2, starting with the acids and amines obtained above (or from amines known from the literature), and by using the acid which is adapted for the salification of the purified basic compound, the following compounds according to the invention are obtained:

EXAMPLE 44

N-[2-[2-[4-(1,1,2,2,6,6-pentamethyl-4-piperidinyl)-1-piperazinyl]-2-oxo-ethoxy]ethyl]-4-methoxy-N,2,6-trimethylbenzenesulphonamide, bis(trifluoroacetate)

Colourless oil (yield=37%).
$^1$H NMR (300 MHz, CD3CN) δ: 8.70 (m broad, 1H); 6.75 (s, 2H); 4.10 (s, 2H); 3.80 (s, 3H); 3.76 (m, 4H); 3.70 (t, 1H); 3.61 (t, 2H); 3.28 (m, 4H); 2.27 (s, 6H); 2.57 (s, 6H); 2.28 (dm, 4H); 1.47 (s, 6H); 1.38 (s, 6H).

EXAMPLE 45

N-[2-[2-[4-[3-(4-methyl-1-piperazinyl)propyl]-1-piperazinyl]-2-oxo-ethoxy]ethyl]-4-methoxy-N,2,6-trimethylbenzenesulphonamide, difumarate White solid (yield=30%).
M.Pt.=204° C.

EXAMPLE 46

N-[2-[2-[4-(8-ethyl-8-azabicyclo[3.2.1]oct-3-yl)-1-piperazinyl]-2-oxo-ethoxy]ethyl]-4-methoxy-N,2,6-trimethylbenzenesulphonamide, difumarate White solid (yield=27%).
M.Pt.=132° C.

EXAMPLE 47

N-[2-[2-[4-[3-(4-methyl-hexahydro-1H-1,4-diazepin-1-yl)propyl]-1-piperazinyl]-2-oxo-ethoxy]ethyl]-4-methoxy-N,2,6-trimethylbenzenesulphonamide, difumarate White solid (yield=45%).
M.Pt.=169° C.

EXAMPLE 48

N-[2-[2-[4-[8-(1-methylethyl)-8-azabicyclo[3.2.1]oct-3-yl]-1-piperazinyl]-2-oxo-ethoxy]ethyl]-4-methoxy-N,2,6-trimethylbenzenesulphonamide, difumarate White solid (yield=35%).
M.Pt.=132° C.

EXAMPLE 49

N-[2-[2-[4-[3-(4-methyl-hexahydro-1H-1,4-diazepin-1-yl)-3-oxo-propyl]-1-piperazinyl]-2-oxo-ethoxy]ethyl]-N,2,6-trimethylbenzenesulphonamide, bis(trifluoroacetate)

Colourless oil (yield=35%).
$^1$H NMR (300 MHz, CD3CN) δ: 6.76 (s, 2H); 4.15 (s, 2H); 3.84 (s, 3H); 3.82 (m, 6H); 3.65 (t, 2H); 3.62 (m, 2H); 3.44 (t, 2H); 3.36 (m, 10H); 2.90 (t, 2H); 2.87 (s, 3H); 2.77 (s, 3H); 2.61 (s, 6H); 2.18 (m, 2H).

EXAMPLE 50

N-[2-[2-[4-[2-(4-methyl-hexahydro-1H-1,4-diazepin-1-yl)ethyl]-1-piperazinyl]-2-oxo-ethoxy]ethyl]-4-methoxy-N,2,6-trimethylbenzenesulphonamide, trifumarate White solid (yield=8%).
M.Pt.=176° C.
In operating analogously to Examples 5 and 4, starting with the acids obtained above, the two following compounds according to the invention are obtained:

EXAMPIE 51

N-[2-[2-[4-((3S)-1-azabicyclo[2.2.2]oct-3-yl)-1-piperazinyl]-2-oxo-ethoxy]ethyl]-4-methoxy-N-cyclopropyl-2,6-dimethylbenzenesulphonamide, difumarate White solid (yield=37%).
M.Pt.=72° C.
$[\alpha_D^{25}]$=−11.4° (c=0.5; $CH_3OH$)

EXAMPLE 52

N-[2-[2-[4-((3S)-1-azabicyclo[2.2.2]oct-3-yl)-1-piperazinyl]-2-oxo-ethoxy]ethyl]-4-methoxy-N-ethyl-2,6-dimethylbenzenesulphonamide, difumarate White solid (yield=32%).
M.Pt.=70° C.
$[\alpha_D^{25}]$=−11° (c=0.5; $CH_3OH$)
In operating analogously to Example 1, starting with the acid obtained according to preparation III and 1-[2-(diethylamino)ethyl]piperazine, the following compound according to the invention is obtained:

EXAMPLE 53

N-[2-[2-[4-[2-(diethylamino)ethyl]-1-piperazinyl]-2-oxo-ethoxy]ethyl]-4-methoxy-N,2,6-trimethylbenzenesulphonamide, fumarate White pasty solid (yield=77%).
$^1$H NMR (300 MHz, CD3CN) δ: 6.74 (s, 2H); 6.60 (s, 2H); 4.02 (s, 2H); 3.80 (s, 3H); 3.54 (t, 2H); 3.46 (m, 2H); 3.32 (m, 2H); 3.26 (t, 2H); 2.96 (m, 6H); 2.74 (s, 3H); 2.62 (t, 2H); 2.57 (s, 6H); 2.41 (m, 4H); 1.16 (t, 6H).

PREPARATION CXXXII

[2-[methyl(phenylmethyl)amino]ethoxy]acetic acid, 1,1-dimethylethyl ester

In operating analogously to preparation II, starting with 2-[methyl(phenylmethyl)amino]ethanol, the product sought after is obtained as a colourless oil (yield=35%).
$^1$H NMR (250 MHz, DMSO) δ: 7.26 (m, 5H); 3.96 (s, 2H); 3.57 (t, 2H); 3.49 (s, 2H); 2.49 (m, 2H); 2.14 (s, 3H); 1.40 (s, 9H).

PREPARATION CXXXIII

[2-[methyl(phenylmethyl)amino]ethoxy]acetic acid, lithium salt

A solution of 1 g (3.58 mM) of the compound obtained according to preparation CXXXII in 10 ml of tetrahydrofuran is heated under the reflux of the solvent in the presence of 165 mg of lithia and 3 ml of water, for 8 hours. The reaction mixture is then concentrated under reduced pressure to give the product sought after as a colourless foam (yield=99%).
$^1$H NMR (250 MHz, DMSO) δ: 7.26 (m, 5H); 3.59 (s, 2H); 3.53 (t, 2H); 3.48 (s, 2H); 2.50 (t, 2H); 2.12 (s, 3H).

PREPARATION CXXXIV

N-methyl-N-[2-[2-[4-(1-methyl-4-piperidinyl)-1-piperazinyl]-2-oxoethoxy]ethyl]-benzenemethanamine In operating analogously to Example 5, starting with the salt obtained according to preparation CXXXIII and 1-(1-methyl-4-piperidinyl)piperazine, the product sought after is obtained as a yellow oil (yield=24%).
$^1$H NMR (250 MHz, DMSO) δ: 7.26 (m, 5H); 4.09 (s, 2H); 3.54 (t, 2H); 3.49 (s, 2H); 3.37 (m, 4H); 2.78 (m, 2H); 2.53 (t, 2H); 2.43 (m, 4H); 2.41 (s, 3H); 2.11 (s, 3H); 2.07 (m, 1H); 1.80 (dt, 2H); 1.65 (dm, 2H); 1.39 (dq, 2H).

PREPARATION CXXXV

N-methyl-2-[2-[4-(1-methyl-4-piperidinyl)-1-piperazinyl]-2-oxoethoxy]ethanamine

In operating analogously to preparation XXXV, starting with the compound obtained according to preparation CXXXIV, the product sought after is obtained as a yellow oil (yield=80%).
$^1$H NMR (300 MHz, DMSO) δ: 4.16 (s, 2H); 3.55 (t, 2H); 3.49 (m, 1H); 3.39 (m, 2H); 3.33 (m, 2H); 2.77 (t, 4H); 2.43 (m, 2H); 2.38 (s, 3H); 2.16 (m, 2H); 2.12 (s, 3H); 1.82 (dt, 2H); 1.67 (dm, 2H); 1.38 (dq, 2H).

PREPARATION CXXXVI 2,6-dichloro-4-fluorobenzenesulphonyl chloride

A solution of 4.75 g (25 mM) of 2,6-dichloro-4-fluoroaniline in 50 ml of dichloromethane are added, at −15° C., to 4.75 ml of boron trifluoride etherate. 5 ml of tetrahydrofuran are added to dissolve the precipitate formed, then, slowly, 3.6 ml of t-butyl nitrite in solution in 25 ml of dichloromethane are added. The reaction mixture is agitated 10 minutes at −15° C. and then 20 minutes at +5° C. 200 ml of pentane are added, and agitation is maintained at 0° C. for 30 min and the precipitate is filtered off. After drying, 7.2 g of the diazonium salt are obtained. This salt is dissolved in 30 ml of acetonitrile and is added, at 10° C., to a mixture of a solution of sulphur dioxide in 90 ml of acetic acid to which 1.4 g of anhydrous copper (II) chloride and 23 ml of concentrated hydrochloric acid have been added. The reaction mixture is agitated 30 min at ambient temperature and then concentrated under reduced pressure. The residue from evaporation is taken up into 60 ml of dichloromethane and the insoluble salts are removed by filtration. The filtrate is concentrated under reduced pressure to give 4.71 g of the product sought after as orange crystals (yield=71%).
M.Pt.=57° C.

EXAMPLE 54

N-[2-[2-[4-(1-methyl-4-piperidinyl)-1-piperazinyl]-2-oxo-ethoxy]ethyl]-2,6-dichloro-4-fluoro-N-methyl-benzenesulphonamide In operating analogously to preparation I, starting with the compounds obtained according to preparations CXXXV and CXXXXVI, the product sought after is obtained as a pale yellow oil (yield=73%).

$^1$H NMR (250 MHz, DMSO) δ: 7.73 (d, 2H); 4.08 (s, 2H); 3.58 (t, 2H); 3.45 (t, 2H); 3.40 (m, 2H); 3.30 (m, 2H); 2.93 (s, 3H); 2.78 (m, 2H); 2.41 (m, 4H); 2.13 (m, 1H); 2.11 (s, 3H); 1.81 (t, 2H); 1.75 (m, 2H); 1.40 (m, 2H).

EXAMPLE 55

N-[2-[2-[4-(1-methyl-4-piperidinyl)-1-piperazinyl]-2-oxo-ethoxy]ethyl]-2,6-dichloro-4-fluoro-N-methyl-benzenesulphonamide, difumarate In operating analogously to Example 4, starting with the compound obtained according to Example 54, the product sought after is obtained as a white solid (yield=76%).

M.Pt.=152-155° C.

In operating analogously to Examples 54 and 55, starting with benzenesulphonyl chlorides having various substituents, the following compounds according to the invention are obtained:

EXAMPLE 56

N-[2-[2-[4-(1-methyl-4-piperidinyl)-1-piperazinyl]-2-oxo-ethoxy]ethyl]-4-bromo-2,6-dichloro-N-methyl-benzenesulphonamide Colourless oil (yield=37%).

$^1$H NMR (300 MHz, DMSO) δ: 7.97 (s, 2H); 4.07 (s, 2H); 3.58 (t, 2H); 3.45 (t, 2H); 3.43 (m, 2H); 2.99 (s, 3H); 2.74 (m, 2H); 2.42 (m, 4H); 2.14 (m, 1H); 2.13 (s, 3H); 1.81 (t, 2H); 1.76 (m, 2H); 1.44 (m, 2H).

EXAMPLE 57

N-[2-[2-[4-(1-methyl-4-piperidinyl)-1-piperazinyl]-2-oxo-ethoxy]ethyl]-4-bromo-2,6-dichloro-N-methyl-benzenesulphonamide, difumarate White solid (yield=87%).
M.Pt.=194° C.

EXAMPLE 58

N-[2-[2-[4-(1-methyl-4-piperidinyl)-1-piperazinyl]-2-oxo-ethoxy]ethyl]-2,4,6-trichloro-N-methyl-benzenesulphonamide Colourless oil (yield=64%).

$^1$H NMR (300 MHz, DMSO) δ: 7.88 (s, 2H); 4.08 (s, 2H); 3.58 (t, 2H); 3.44 (t, 2H); 3.38 (m, 4H); 2.94 (s, 3H); 2.78 (m, 2H); 2.42 (m, 4H); 2.17 (m, 1H); 2.11 (s, 3H); 1.81 (t, 2H); 1.76 (m, 2H); 1.44 (m, 2H).

EXAMPLE 59

N-[2-[2-[4-(1-methyl-4-piperidinyl)-1-piperazinyl]-2-oxo-ethoxy]ethyl]-2,4,6-trichloro-N-methyl-benzenesulphonamide, difumarate White solid (yield=82%).
M.Pt.=194° C.

EXAMPLE 60

N-[2-[2-[4-(1-methyl-4-piperidinyl)-1-piperazinyl]-2-oxo-ethoxy]ethyl]-2,4-dichloro-6-methyl-N-methyl-benzenesulphonamide Colourless oil (yield=61%).

$^1$H NMR (300 MHz, DMSO) δ: 7.70 (d, 1H); 7.56 (d, 1H); 4.07 (s, 2H); 3.57 (t, 2H); 3.37 (m, 2H); 3.30 (s, 4H); 2.85 (s, 3H); 2.74 (m, 2H); 2.62 (s, 3H); 2.42 (m, 4H); 2.13 (m, 1H); 2.11 (s, 3H); 1.81 (t, 2H); 1.77 (m, 2H); 1.43 (m, 2H).

EXAMPLE 61

N-[2-[2-[4-(1-methyl-4-piperidinyl)-1-piperazinyl]-2-oxo-ethoxy]ethyl]-2,4-dichloro-6-methyl-N-methyl-benzenesulphonamide, difumarate White solid (yield=87%).
M.Pt.=190° C.

EXAMPLE 62

N-[2-[2-[4-(1-methyl-4-piperidinyl)-1-piperazinyl]-2-oxo-ethoxy]ethyl]-4-methoxy-2,3,6-trimethyl-N-methyl-benzenesulphonamide Colourless oil (yield=34%).

$^1$H NMR (250 MHz, DMSO) δ: 6.83 (s, 1H); 4.03 (s, 2H); 3.84 (s, 3H); 3.52 (t, 2H); 3.35 (m, 2H); 3.35 (m, 2H); 3.18 (t, 2H); 2.73 (m, 2H); 2.69 (s, 3H); 2.57 (s, 3H); 2.42 (s, 3H); 2.41 (t, 4H); 2.12 (s, 3H); 2.10 (m, 1H); 2.08 (s, 3H); 1.81 (m, 2H); 1.66 (m, 2H); 1.38 (m, 2H).

EXAMPLE 63

4-methoxy-N,2,3,6-tetramethyl-N-[2-[2-[4-(1-methyl-4-piperidinyl)-1-piperazinyl]-2-oxo-ethoxy]ethyl]benzenesulphonamide, difumarate White solid (yield=71%).
M.Pt.=180° C.

PREPARATION CXXXVII

4-[[2-[[(4-methoxy-2,6-dimethylphenyl)sulphonyl]methylamino]ethoxy]acetyl]-1-piperazinecarboxylic acid, 1,1-dimethylethyl ester In operating analogously to Example 5, starting with N-Boc-piperazine, the product sought after is obtained which is used in the next step without particular purification.

PREPARATION CXXXVIII 4-methoxy-N,2,6-trimethyl-N-[2-[2-oxo-2-(1-piperazinyl)ethoxy]ethyl]benzenesulphonamide In operating analogously to preparation XXIX, starting with the compound obtained following preparation CXXXVII, the product sought after is obtained as a yellow oil (yield=98%).

$^1$H NMR (250 MHz, DMSO) δ: 6.80 (s, 2H); 4.04 (s, 2H); 3.80 (s, 3H); 3.53 (t, 2H); 3.30 (m, 4H); 3.23 (t, 4H); 2.70 (s, 3H); 2.60 (t, 4H); 2.53 (s, 6H).

PREPARATION CXXXIX 4-(3-oxopropyl)-1-piperidinecarboxylic acid, phenylmethyl ester 0.81 ml of dimethylsulphoxide in solution in 10 ml of dichloromethane (DCM) is cooled to −50° C. and 0.42 ml (4.8 mM) of oxalyl chloride in solution in 1.5 ml of DCM are added. The mixture is agitated for 10 minutes at −60° C. are then, at this temperature, 1.21 g (4.4 mM) of the benzyl ester of 4-(3-hydroxypropyl)piperidinecarboxylic acid in solution in 6 ml of DCM are added dropwise. The reaction mixture is agitated for 30 minutes at −50° C. and 3 ml of triethylamine are then added dropwise and the temperature is allowed to rise up to ambient temperature in 2 hours. The mixture is hydrolysed on 25 ml of N hydrochloric acid and extracted with DCM. The organic phase is washed with water, dried over magnesium sulphate and concentrated under reduced pressure. The crude product is purified by silica gel chromatography in eluting with the aid of a cyclohexane/ethyl acetate mixture (75/25; v/v). The product sought after is thus obtained as a yellow oil (yield=83%).

$^1$H NMR (300 MHz, DMSO) δ: 9.66 (s, 1H); 7.35 (m, 5H); 5.05 (s, 2H); 3.98 (m, 2H); 2.75 (m, 2H); 2.44 (m, 2H); 1.64 (q, 2H); 1.63 (m, 2H); 1.37 (m, 1H); 1.02 (m, 2H).

PREPARATION CXL

4-[3-[4-[[2-[[(4-methoxy-2,6-dimethylphenyl)sulphonyl]methyl amino]ethoxy]acetyl]-1-piperazinyl] propyl]-1-piperidinecarboxylic acid, phenylmethyl ester In operating analogously to preparation XXVIII, starting with the compounds obtained following preparations CXXXVIII and CXXXIX, the product sought after is obtained as a colourless oil (yield=51%).

$^1$H NMR (300 MHz, DMSO) δ: 7.40 (m, 5H); 6.81 (s, 2H); 5.05 (s, 2H); 4.33 (s, 2H); 3.96 (m, 2H); 3.79 (s, 3H); 3.55 (t, 2H); 3.37 (m, 2H); 3.30 (m, 2H); 3.19 (t, 2H); 2.71 (m, 2H); 2.69 (s, 3H); 2.52 (s, 6H); 2.25 (m, 6H); 1.65 (m, 2H); 1.42 (m, 3H); 1.20 (m, 2H); 1.00 (m, 2H).

EXAMPLE 64

4-methoxy-N,2,6-trimethyl-N-[2-[2-oxo-2-[4-[3-(4-piperidinyl)propyl]-1-piperazinyl]ethoxy]ethyl]benzenesulphonamide In operating analogously to preparation XXXV, starting with the compound obtained following preparation CXL, the product sought after is obtained as a colourless oil (yield=62%).

$^1$H NMR (250 MHz, DMSO) δ: 6.80 (s, 2H); 4.05 (s, 2H); 3.80 (s, 3H); 3.53 (t, 2H); 3.30 (m, 4H); 3.19 (t, 2H); 2.88 (m, 2H); 2.69 (s, 3H); 2.50 (s, 6H); 2.44 (m, 2H); 2.27 (m, 6H); 1.57 (m, 2H); 1.41 (m, 3H); 1.17 (m, 2H); 0.97 (m, 2H).

EXAMPLE 65

4-methoxy-N,2,6-trimethyl-N-[2-[2-oxo-2-[4-[3-(1-methyl-4-piperidinyl)propyl]-1-piperazinyl]ethoxy] ethyl]benzenesulphonamide In operating analogously to preparation XXVIII, starting with the compound obtained following Example 64, the product sought after is obtained as a colourless oil (yield=90%).

$^1$H NMR (250 MHz, DMSO) δ: 6.80 (s, 2H); 4.05 (s, 2H); 3.80 (s, 3H); 3.53 (t, 2H); 3.38 (m, 2H); 3.24 (t, 2H); 3.18 (m, 2H); 2.72 (m, 2H); 2.69 (s, 3H); 2.50 (s, 6H); 2.28 (m, 6H); 2.11 (s, 2H); 1.78 (m, 2H); 1.60 (m, 2H); 1.45 (m, 2H); 1.15 (m, 5H).

EXAMPLE 66

4-methoxy-N,2,6-trimethyl-N-[2-[2-oxo-2-[4-[3-(1-methyl-4-piperidinyl)propyl]-1-piperazinyl]ethoxy] ethyl]benzenesulphonamide, difumarate In operating analogously to Example 4, starting with the compound obtained following Example 65, the product sought after is obtained as a white solid (yield=98%).

M.Pt.=50° C.

PREPARATION CXLI

4-[4-(phenylmethyl)-1-piperazinyl]-1-piperidinecarboxylic acid, 1,1-dimethylethyl ester In operating analogously to preparation XXVIII, starting with N-benzylpiperazine and N-Boc-4-piperidinone, the product sought after is obtained as a colourless oil (yield=60%).

$^1$H NMR (300 MHz, CDCl3) δ: 7.27 (m, 5H); 4.15 (m, 2H); 3.52 (s, 2H); 2.61 (m, 11H); 1.81 (m, 2H); 1.44 (s, 9H); 1.41 (m, 2H).

PREPARATION CXLII 4-(1-piperazinyl)-1-piperidinecarboxylic acid, 1,1-dimethylethyl ester A solution is prepared of 15.5 g (43.1 mM) of the compound obtained according to preparation CXLI in 46 ml of ethanol and 3.1 g of palladium hydroxide are added, and then, after rendering the reactor inert, 17.7 g (215 mM) of cyclohexene are added. The reaction mixture is agitated at 50° C. for 6 hours and then cooled and filtered. The filtrate is concentrated under reduced pressure and 10.02 g of the product sought after are obtained as a colourless oil (yield=86%).

$^1$H NMR (300 MHz, CDCL3) δ: 4.12 (m, 2H); 2.92 (m, 4H); 2.69 (m, 2H); 2.55 (t, 4H); 2.36 (m, 1H); 1.79 (m, 2H); 1.45 (s, 9H); 1.38 (m, 2H).

PREPARATION CXLIII

4-[4-[[2-[[(4-methoxy-2,6-dimethylphenyl)sulpho-nyl]-methylaminoethoxy]acetyl]-1-piperazinyl]-1-piperidinecarboxylic acid, 1,1-dimethylethyl ester In operating analogously to Example 3, starting with the compounds obtained following preparations III and CXLII, the product sought after is obtained as a colourless oil (yield=32%).

$^1$H NMR (300 MHz, CD3CN) δ: 6.74 (s, 2H); 4.07 (m, 2H); 4.00 (s, 2H); 3.80 (s, 3H); 3.54 (t, 2H); 3.43 (m, 2H); 3.26 (m, 4H); 2.74 (s, 3H); 2.69 (m, 2H); 2.57 (s, 6H); 2.44 (m, 4H); 2.34 (m, 1H); 1.71 (m, 2H); 1.41 (s, 9H); 1.29 (m, 2H).

EXAMPLE 67

4-methoxy-N,2,6-trimethyl-N-[2-[2-oxo-2-[4-(4-piperidinyl)-1-piperazinyl]ethoxy]ethyl]benzene-sulphonamide, bis(trifluoroacetate)

A mixture is prepared of 140 mg (0.24 mM) of the compound obtained according to preparation CXLIII in 1 ml of dichloromethane and 0.7 ml of trifluoroacetic acid. The reaction mixture is agitated at ambient temperature for 2 hours and then concentrated under reduced pressure. The residue from evaporation is taken up into 3 ml of water and is freeze-dried. 160 mg of the product sought after are thus obtained as a white solid (yield=95%).

M.Pt.=62° C.

PREPARATION CXLIV 4-(6-nitro-3-pyridinyl)-1-piperazinecarboxylic acid, 1,1-dimethylethyl ester A solution is prepared of 1 g (4.9 mM) of 2-nitro-5-bromopyridine and 917 mg (4.9 mM) of N-Boc-piperazine in 10 ml of dimethylformamide and 1.02 g (7.4 mM) of potassium carbonate are added. The reaction mixture is agitated at 120° C. for 36 hours and then cooled. 50 ml of water are then added and extraction is carried out with ethyl acetate. The organic phase obtained is washed with water, dried and concentrated under reduced pressure. The crude product is purified by silica gel chromatography in eluting with the aid of a toluene/isopropanol mixture (98/2; v/v). The product sought after is thus obtained as a yellow solid (yield=33%).

$^1$H NMR (250 MHz, DMSO) δ: 8.24 (d, 1H); 8.17 (d, 1H); 7.46 (dd, 1H); 3.50 (m, 8H); 1.42 (s, 9H).

PREPARATION CXLV 1-(6-nitro-3-pyridinyl)piperazine, bis(trifluoroacetate)

In operating analogously to Example 67, starting with the compound obtained following preparation CXLIV, the product sought after is obtained as a yellow solid (yield=97%).

M.Pt.=188-190° C.

PREPARATION CXLVI 4-methoxy-N,2,6-trimethyl-N-[2-[2-oxo-2-[4-(6-nitro-3-pyridinyl)-1-piperazinyl]ethoxy]ethyl]benzene-nesulphonamide In operating analogously to Example 3, starting with the compounds obtained following preparations III and CXLV, the product sought after is obtained as a yellow solid (yield=82%).

M.Pt.=118-120° C.

EXAMPLE 68

4-methoxy-N,2,6-trimethyl-N-[2-[2-oxo-2-[4-(6-amino-3-pyridinyl)-1-piperazinyl]ethoxy]ethyl]ben-zenesulphonamide A suspension is prepared of 580 mg (1.11 mM) of the compound obtained following preparation CXLVI in 20 ml of methanol and 58 mg of 10% palladium on carbon are added. The reaction mixture is agitated at ambient temperature for 6 hours under an atmosphere of hydrogen at atmospheric pressure and is then filtered and concentrated under reduced pressure. The crude product is purified by silica gel chromatography in eluting with the aid of a dichloromethane/methanol mixture (97/3; v/v). The product sought after is thus obtained as a yellow pasty solid (yield=81%).

$^1$H NMR (300 MHz, DMSO) δ: 7.61 (d, 1H); 7.17 (dd, 1H); 6.80 (s, 2H); 6.40 (dd, 1H); 5.43 (s, 2H); 4.11 (s, 2H); 3.79 (s, 3H); 3.55 (m, 4H); 3.44 (m, 2H); 3.24 (t, 2H); 2.87 (m, 4H); 2.70 (s, 3H); 2.53 (s, 6H).

EXAMPLE 69

4-methoxy-N,2,6-trimethyl-N-[2-[2-oxo-2-[4-(6-amino-3-pyridinyl)-1-piperazinyl]ethoxy]ethyl]ben-zenesulphonamide, fumarate In operating analogously to Example 4, starting with the compound obtained following Example 68, the product sought after is obtained as a beige solid (yield=97%).

M.Pt.=194-196° C.

EXAMPLE 70

N-[2-[2-[4-[2-(dimethylamino)-1,1-dimethylethyl]-1-piperidinyl]-2-oxoethoxy]ethyl]-4-methoxy-N,2,6-trimethylbenzenesulphonamide, trifluoroacetate 460 mg of polystyrene resin grafted with a cyclohexylcar-bodiimide function are placed in 5 ml of DCM for 20 min. The solvent is removed by filtration, and 100 mg (0.31 mM) of [2-[[(4-methoxy-2,6-dimethylphenyl)sulphonyl]methy-lamino]-ethoxy]acetic acid in solution in 3 ml of DCM, 37 mg (0.20 mM) of 4-[2-(dimethylamino)-1,1-dimethylethyl]piperidine and 2 mg of HOAT(1-hydroxy-7-azabenzotriazole), are then added. The mixture is agitated for 4 hours and then the resin is separated off by filtration and rinsed with 4 ml of DCM. The combined organic phases are treated with 50 mg of Amberlite IRA 400 resin (OH⁻) for 3 hours, and then with 100 mg of isocyanate grafted polystyrene resin for 1 hour. The resin is removed by filtration and the filtrate is concentrated under reduced pressure. The product obtained is taken up into 0.5 ml of acetonitrile and 6 ml of a 1% solution of trifluoro-acetic acid in water are added. The mixture is filtered and freeze-dried. 59 mg of the compound sought after are thus obtained as an amorphous solid (yield=48%).

M.Pt.=60° C.

$^1$H NMR (250 MHz, CD$_3$CN) δ: 6.74 (s, 2H); 4.50 (m, 1H); 4.06 (m, 2H); 3.80 (s, 3H); 3.78 (m, 1H); 3.57 (t, 2H); 3.31 (t, 2H); 3.04 (s, 2H); 2.85 (s, 6H); 2.83 (m, 1H); 2.73 (s, 3H); 2.56 (s, 6H); 2.55 (m, 1H); 1.65 (m, 2H); 1.45 (m, 1H), 1.20 (m, 2H); 0.99 (s, 6H).

EXAMPLE 71

N-[2-[2-[4-[2-(dimethylamino)-1-hydroxyethyl]-1-piperidinyl]-2-oxoethoxy]ethyl]-4-methoxy-N,2,6-trimethylbenzenesulphonamide, trifluoroacetate In operating analogously to Example 70, starting with the compound obtained according to preparation LXIX, the product sought after is obtained as a colourless paste (yield=45%).

$^1$H NMR (250 MHz, CD$_3$CN) δ: 6.74 (s, 2H); 4.45 (m, 1H); 4.05 (m, 2H); 3.80 (s, 3H); 3.75 (m, 2H); 3.59 (t, 2H); 3.28 (t, 2H); 3.06 (m, 2H); 2.90 (m, 1H); 2.84 (s, 3H); 2.80 (s, 3H); 2.77 (s, 3H); 2.56 (s, 6H); 2.50 (m, 1H); 1.80 (m, 1H); 1.60 (m, 2H); 1.20 (m, 2H).

EXAMPLE 72

4-methoxy-N,2,6-trimethyl-N-[2-[2-[4-(4-methyl-1-piperazinyl)-1-piperidinyl]-2-oxoethoxy]ethyl]benzenesulphonamide A suspension is prepared of 350 mg (1.06 mM) of acid obtained according to preparation III in 3 ml of DCM and 243 mg (1.27 mM) of EDCI (1-(3-dimethylaminopropyl)-3-ethylcarbodiimide hydrochloride) and 173 mg (1.27 mM) of HOAT, are added. The mixture is agitated for 30 min at ambient temperature, and 232 mg (1.27 mM) of 1-methyl-4-(4-piperidinyl)piperazine are then added. The reaction mixture is agitated for 18 hours at ambient temperature and is then poured over 10 ml of water and extracted with DCM. The organic phase is washed with water, dried and concentrated under reduced pressure. The residue is purified by silica gel chromatography in eluting with the aid of a DCM/methanol mixture (90/10; v/v). 449 mg of the product sought after are thus obtained as a yellow oil (yield=86%).

$^1$H NMR (300 MHz, CD$_3$CN) δ: 6.74 (s, 2H); 4.35 (d, 1H); 4.01 (q, 2H); 3.81 (s, 3H); 3.69 (d, 1H); 3.56 (t, 2H); 3.26 (t, 2H); 2.89 (t, 1H); 2.75 (s, 3H); 2.58 (s, 6H); 2.40 (m, 10H); 2.17 (s, 3H); 1.75 (m, 2H); 1.27 (m, 2H).

EXAMPLE 73

4-methoxy-N,2,6-trimethyl-N-[2-[2-[4-(4-methyl-1-piperazinyl)-1-piperidinyl]-2-oxoethoxy]ethyl]benzenesulphonamide, fumarate 404 mg (0.814 mM) of the compound obtained according to Example 72 are dissolved in 5 ml of methanol and 95 mg (0.815 mM) of fumaric acid are added. The mixture is agitated for 10 min and then concentrated under reduced pressure. The residue is taken up into 10 ml of water and the solution is freeze-dried. The salt sought after is thus obtained (474 mg) as a white powder (yield=95%).

M.Pt.=90° C.

In operating analogously to Examples 72 and 73, starting with the acids and the derivatives of piperidine described above or known from the literature, the following compounds according to the invention are obtained:

EXAMPLE 74

4-methoxy-N,2,6-trimethyl-N-[2-[2-[4-(1-methyl-4-piperidinyl)-1-piperidinyl]-2-oxoethoxy]ethyl]benzenesulphonamide, fumarate White solid (yield=44%).

M.Pt.=88-89° C.

EXAMPLE 75

N-cyclopropyl-4-methoxy-2,6-dimethyl-N-[2-[2-[4-(4-methyl-1-piperazinyl)-1-piperidinyl]-2-oxoethoxy]ethyl]benzenesulphonamide, difumarate White solid (yield=76%).

M.Pt.=148° C.

EXAMPLE 76

4-methoxy-N,2,6-trimethyl-N-[2-[2-[4-[2-(1-pyrrolidinyl)ethyl]-1-piperidinyl]-2-oxoethoxy]ethyl]benzenesulphonamide, fumarate White solid (yield=87%).

M.Pt.=55° C.

$^1$H NMR (300 MHz, CD3CN) δ: 8.50 (m broad, 1H); 6.74 (s, 2H); 4.38 (m, 1H); 4.10 (d, 2H); 3.80 (s, 3H); 3.75 (m, 1H); 3.57 (m, 4H); 3.27 (t, 2H); 3.13 (m, 2H); 2.95 (m, 3H); 2.74 (s, 3H); 2.57 (s, 6H); 2.50 (m, 1H); 2.06 (m, 4H); 1.65 (m, 5H); 1.07 (m, 2H).

EXAMPLE 77

4-methoxy-N,2,6-trimethyl-N-[2-[2-[4-[4-(1-methylethyl)-1-piperazinyl]-1-piperidinyl]-2-oxoethoxy]ethyl]benzenesulphonamide, fumarate White solid (yield=92%).

M.Pt.=145° C.

EXAMPLE 78

N-ethyl-4-methoxy-2,6-dimethyl-N-[2-[2-[4-[2-(1-pyrrolidinyl)ethyl]-1-piperidinyl]-2-oxoethoxy]ethyl]benzenesulphonamide, fumarate White solid (yield=50%).

M.Pt.=50° C.

EXAMPLE 79

N-cyclopropyl-4-methoxy-2,6-dimethyl-N-[2-[2-[4-[2-(1-pyrrolidinyl)ethyl]-1-piperidinyl]-2-oxoethoxy]ethyl]benzenesulphonamide, fumarate White solid (yield=96%).

M.Pt.=50° C.

EXAMPLE 80

N-[2-[2-[4-[2-(hexahydro-4-methyl-1H-1,4-diazepin-1-yl)ethyl]-1-piperidinyl]-2-oxoethoxy]ethyl]-4-methoxy-N,2,6-trimethylbenzenesulphonamide, difumarate White solid (yield=54%).
M.Pt.=60° C.

EXAMPLE 81

4-methoxy-N,2,6-trimethyl-N-[2-[2-[4-[2-[methyl(1-methylethyl)amino]ethyl]-1-piperidinyl]-2-oxoethoxy]ethyl]-benzenesulphonamide, fumarate White solid (yield=64%).
M.Pt.=60° C.

EXAMPLE 82

4-methoxy-N,2,6-trimethyl-N-[2-[2-[4-[methyl(1-methyl-4-piperidinyl)amino]-1-piperidinyl]-2-oxoethoxy]ethyl]benzenesulphonamide, fumarate White solid (yield=66%).
M.Pt.=72° C.

EXAMPLE 83

4-methoxy-N,2,6-trimethyl-N-[2-[2-[4-[1-(1-methylethyl)-4-piperidinyl]-1-piperidinyl]-2-oxoethoxy]ethyl]benzenesulphonamide, fumarate White solid (yield=84%).
M.Pt.=62-64° C.

EXAMPLE 84

4-methoxy-N,2,6-trimethyl-N-[2-[2-[4-(1-ethyl-4-piperidinyl)-1-piperidinyl]-2-oxoethoxy]ethyl]benzenesulphonamide, fumarate Colourless oil (yield=35%).
$^1$H NMR (300 MHz, DMSO) δ: 6.80 (s, 2H); 6.51 (s, 2H); 4.32 (m, 1H); 4.06 (q, 2H); 3.80 (s, 3H); 3.67 (m, 1H); 3.53 (m, 2H); 3.22 (m, 2H); 3.15 (d, 2H); 2.86 (m, 1H); 2.69 (s, 3H); 2.61 (q, 2H); 2.53 (s, 6H); 2.45 (m, 1H); 2.27 (t, 2H); 1.66 (m, 4H); 1.30 (m, 3H); 1.07 (t, 3H); 0.96 (m, 3H).

EXAMPLE 85

4-methoxy-N,2,6-trimethyl-N-[2-[2-[4-(1-cyclopropyl-4-piperidinyl)-1-piperidinyl]-2-oxoethoxy]ethyl]benzenesulphonamide, fumarate Colourless oil (yield=63%).
$^1$H NMR (300 MHz, DMSO) δ: 6.80 (s, 2H); 6.66 (s, 2H); 4.34 (m, 1H); 4.01 (q, 2H); 3.79 (s, 3H); 3.66 (m, 1H); 3.54 (t, 2H); 3.21 (t, 2H); 2.98 (d, 2H); 2.82 (m, 1H); 2.69 (s, 3H); 2.53 (s, 6H); 2.43 (m, 1H); 2.10 (t, 2H); 1.60 (m, 5H); 1.23 (m, 1H); 1.03 (m, 5H); 0.38 (m, 2H); 0.29 (m, 2H).

EXAMPLE 86

4-methoxy-N,2,6-trimethyl-N-[2-[2-[4-[2-(4-morpholinyl)ethyl]-1-piperidinyl]-2-oxoethoxy]ethyl] benzenesulphonamide, fumarate White solid (yield=73%).
M.Pt.=50° C.

EXAMPLE 87

4-methoxy-N,2,6-trimethyl-N-[2-[2-[4-[1,1-dimethyl-2-(1-azetidinyl)ethyl]-1-piperidinyl]-2-oxoethoxy]ethyl]benzenesulphonamide, fumarate White solid (yield=67%).
M.Pt.=60-62° C.

EXAMPLE 88

N-ethyl-4-methoxy-2,6-dimethyl-N-[2-[2-[4-(1-methyl-4-piperidinyl)-1-piperidinyl]-2-oxoethoxy] ethyl]benzenesulphonamide, fumarate White solid (yield=67%).
M.Pt.=65° C.

EXAMPLE 89

N-[2-[2-[4-(hexahydro-4-methyl-1H-1,4-diazepin-1-yl)-1-piperidinyl]-2-oxoethoxy]ethyl]-4-methoxy-N,2,6-trimethylbenzenesulphonamide, fumarate Yellow oil (yield=61%).
$^1$H NMR (300 MHz, DMSO) δ: 6.80 (s, 2H); 6.50 (s, 2H); 4.36 (m, 1H); 4.11 (m, 2H); 3.80 (s, 3H); 3.73 (m, 1H); 3.55 (t, 2H); 3.24 (t, 2H); 2.87 (m, 2H); 2.85 (m, 6H); 2.69 (s, 3H); 2.67 (m, 1H); 2.53 (s, 6H); 2.46 (s, 3H); 2.42 (m, 1H); 1.81 (m, 2H); 1.69 (m, 2H); 1.21 (m, 2H).

EXAMPLE 90

N-cyclopropyl-4-methoxy-2,6-dimethyl-N-[2-[2-[4-(1-methyl-4-piperidinyl)-1-piperidinyl]-2-oxoethoxy]ethyl]benzenesulphonamide, fumarate White solid (yield=60%).
M.Pt.=80° C.

EXAMPLE 91

2,4-dichloro-N,3-dimethyl-N-[2-[2-[4-(1-methyl-4-piperidinyl)-1-piperidinyl]-2-oxoethoxy]ethyl]benzenesulphonamide, fumarate White solid (yield=39%).
M.Pt.=86-88° C.

EXAMPLE 92

4-methoxy-N,2,6-trimethyl-N-[2-[2-[4-[2-(1-azetidinyl)ethyl]-1-piperidinyl]-2-oxoethoxy]ethyl]benzenesulphonamide, fumarate White solid (yield=40%).
$^1$H NMR (300 MHz, DMSO) δ: 6.80 (s, 2H); 6.52 (s, 2H); 4.28 (m, 1H); 4.05 (m, 2H); 3.80 (s, 3H); 3.67 (m, 1H); 3.57

(m, 6H); 3.20 (t, 2H); 2.85 (m, 1H); 2.78 (t, 2H); 2.69 (s, 3H); 2.53 (s, 6H); 2.49 (m, 1H); 2.17 (quin, 2H); 1.59 (m, 2H); 1.50 (m, 1H); 1.30 (m, 2H); 0.93 (m, 2H).

EXAMPLE 93

2,6-dichloro-4-methoxy-N-methyl-N-[2-[2-[4-[2-(dimethylamino)ethyl]-1-piperidinyl]-2-oxoethoxy]ethyl]-benzenesulphonamide, fumarate White solid (yield=39%).
M.Pt.=70° C.

EXAMPLE 94

2,6-dichloro-4-methoxy-N-methyl-N-[2-[2-[4-(1-methyl-4-piperidinyl)-1-piperidinyl]-2-oxoethoxy]ethyl]benzenesulphonamide, fumarate White solid (yield=70%).
M.Pt.=67° C.

EXAMPLE 95

4-methoxy-N,2,6-trimethyl-N-[2-[2-[4-[(1-pyrrolidinyl)methyl]-1-piperidinyl]-2-oxoethoxy]ethyl]benzenesulphonamide, fumarate Colourless oil (yield=30%).
$^1$H NMR (250 MHz, DMSO) δ: 6.80 (s, 2H); 6.54 (s, 2H); 4.29 (m, 1H); 4.15 (m, 2H); 3.80 (s, 3H); 3.63 (m, 1H); 3.53 (t, 2H); 3.22 (t, 2H); 2.89 (m, 1H); 2.80 (m, 4H); 2.70 (s, 3H); 2.56 (m, 1H); 2.53 (s, 6H); 2.51 (m, 2H); 1.81 (m, 7H); 0.91 (m, 2H).

EXAMPLE 96

4-methoxy-N,2,6-trimethyl-N-[2-[2-[4-[(4-ethyl-1-piperazinyl)methyl]-1-piperidinyl]-2-oxoethoxy]ethyl]benzenesulphonamide, fumarate White solid (yield=31%).
M.Pt.=120° C.

EXAMPLE 97

N-cyclopropyl-4-methoxy-2,6-dimethyl-N-[2-[2-[4-[(4-methyl-1-piperazinyl)methyl]-1-piperidinyl]-2-oxoethoxy]ethyl]benzenesulphonamide, difumarate White solid (yield=44%).
M.Pt.=160° C.

EXAMPLE 98

N-ethyl-4-methoxy-2,6-dimethyl-N-[2-[2-[4-[(4-methyl-1-piperazinyl)methyl]-1-piperidinyl]-2-oxoethoxy]ethyl]benzenesulphonamide, difumarate White solid (yield=49%).
M.Pt.=98° C.

EXAMPLE 99

N-methyl-4-methoxy-2,6-dichloro-N-[2-[2-[4-[(4-methyl-1-piperazinyl)methyl]-1-piperidinyl]-2-oxoethoxy]ethyl]benzenesulphonamide, difumarate White solid (yield=50%).
M.Pt.=103° C.

EXAMPLE 100

4-methoxy-N,2,6-trimethyl-N-[2-[2-[4-[1,1-dimethyl-2-(1-piperidinyl)ethyl]-1-piperidinyl]-2-oxoethoxy]ethyl]benzenesulphonamide, trifluoroacetate Colourless oil (yield=47%).
$^1$H NMR (300 MHz, CD$_3$CN) δ: 7.50 (m broad, 1H); 6.74 (s, 2H); 4.49 (m, 1H); 4.01 (q, 2H); 3.81 (s, 3H); 3.78 (m, 1H); 3.57 (t, 2H); 3.43 (m, 2H); 3.28 (t, 2H); 3.01 (m, 2H); 2.98 (s, 2H); 2.90 (m, 1H); 2.74 (s, 3H); 2.63 (s, 6H); 2.45 (m, 1H); 1.85 (m, 3H); 1.66 (m, 3H); 1.51 (m, 2H); 1.19 (m, 3H); 1.00 (s, 6H).

EXAMPLE 101

4-methoxy-N,2,6-trimethyl-N-[2-[2-[4-[1,1-dimethyl-2-(1-pyrrolidinyl)ethyl]-1-piperidinyl]-2-oxoethoxy]ethyl]benzenesulphonamide, fumarate White solid (yield=61%).
M.Pt.=50° C.

EXAMPLE 102

N-[2-[2-[4-[2-(ethylmethylamino)ethyl]-1-piperidinyl]-2-oxoethoxy]ethyl]-4-methoxy-N,2,6-trimethylbenzenesulphonamide, fumarate White solid (yield=46%).
$^1$H NMR (300 MHz, DMSO) δ: 6.80 (s, 2H); 6.51 (s, 2H); 4.27 (m, 1H); 4.03 (q, 2H); 3.80 (s, 3H); 3.55 (m, 1H); 3.24 (t, 2H); 3.22 (t, 2H); 2.86 (m, 1H); 2.70 (s, 3H); 2.62 (m, 4H); 2.53 (s, 6H); 2.48 (m, 1H); 2.46 (s, 3H); 1.66 (m, 2H); 1.52 (m, 1H); 1.45 (m, 2H); 1.38 (t, 3H); 0.97 (m, 2H).

EXAMPLE 103

N-[2-[2-[4-[2-(diethylamino)ethyl]-1-piperidinyl]-2-oxoethoxy]ethyl]-4-methoxy-N,2,6-trimethylbenzenesulphonamide, fumarate White solid (yield=52%).
M.Pt.=60° C.

EXAMPLE 104

4-methoxy-N-(1-methylethyl)-2,6-dimethyl-N-[2-[2-[4-[2-(1-pyrrolidinyl)ethyl]-1-piperidinyl]-2-oxoethoxy]ethyl]benzenesulphonamide, fumarate White solid (yield=61%).
M.Pt.=56° C.

EXAMPLE 105

4-methoxy-N,2,6-trimethyl-N-[2-[2-[4-[1,1-dimethyl-2-(4-morpholinyl)ethyl]-1-piperidinyl]-2-oxoethoxy]ethyl]benzenesulphonamide, fumarate White paste (yield=50%).
$^1$H NMR (300 MHz, DMSO) δ: 6.80 (s, 2H); 6.62 (s, 2H); 4.38 (m, 1H); 4.04 (q, 2H); 3.79 (s, 3H); 3.55 (m, 1H); 3.52 (m, 6H); 3.21 (m, 2H); 2.81 (m, 1H); 2.70 (s, 3H); 2.53 (s, 6H); 2.49 (m, 4H); 2.47 (m, 1H); 2.09 (s, 2H); 1.60 (m, 2H); 1.43 (m, 1H); 1.10 (m, 2H); 0.76 (s, 6H).

EXAMPLE 106

N-[2-[2-[4-[2-(hexahydro-4-methyl-1H-1,4-diazepin-1-yl)ethyl]-1-piperidinyl]-2-oxoethoxy]ethyl]-4-methoxy-N,2,6-trimethylbenzenesulphonamide, difumarate White solid (yield=36%).
M.Pt.=125° C.

EXAMPLE 107

N-[2-[2-[4-[(hexahydro-4-methyl-1H-1,4-diazepin-1-yl)methyl]-1-piperidinyl]-2-oxoethoxy]ethyl]-4-methoxy-N,2,6-trimethylbenzenesulphonamide, difumarate White solid (yield=31%).
M.Pt.=100-102° C.

EXAMPLE 108

4-methoxy-N-[2-[2-[4-[2-(1-methyl-4-piperidinyl)ethyl]-1-piperidinyl]-2-oxoethoxy]ethyl]-N,2,6-trimethylbenzenesulphonamide, fumarate White solid (yield=24%).
M.Pt.=70° C.

In operating analogously to Example 70, starting with the acids and the derivatives of piperidine described above or known from the literature, the following compounds according to the invention are obtained:

EXAMPLE 109

4-methoxy-N-[2-[2-[4-[2-(1-piperidinyl)ethyl]-1-piperidinyl]-2-oxoethoxy]ethyl]-N,2,6-trimethylbenzenesulphonamide, fumarate White solid (yield=69%).
M.Pt.=50° C.

EXAMPLE 110

4-methoxy-N-[2-[2-[4-[2-(1-pyrrolidinyl)ethyl]-1-piperidinyl]-2-oxoethoxy]ethyl]-N-methyl-2-trifluoromethyl-benzenesulphonamide, trifluoroacetate Colourless oil (yield=99%).
$^1$H NMR (300 MHz, CD3CN) δ: 8.20 (m broad, 1H); 7.95 (d, 1H); 7.41 (d, 1H); 7.25 (dd, 1H); 4.43 (m, 1H); 4.10 (q, 2H); 3.91 (s, 3H); 3.63 (m, 1H); 3.63 (m, 4H); 3.43 (t, 2H); 3.13 (m, 2H); 2.96 (m, 2H); 2.90 (s, 3H); 2.60 (t, 1H); 2.06 (m, 6H); 1.71 (m, 4H); 1.60 (m, 2H).

EXAMPLE 111

4-methoxy-N-[2-[2-[4-[2-(1-methyl-4-piperazinyl)-2-oxoethyl]-1-piperidinyl]-2-oxoethoxy]ethyl]-N,2,6-trimethylbenzenesulphonamide, fumarate White solid (yield=33%).
M.Pt.=60° C.

EXAMPLE 112

4-methoxy-N,2,6-trimethyl-N-[2-[2-[4-[1,1-dimethyl-2-(diethylamino)ethyl]-1-piperidinyl]-2-oxoethoxy]ethyl]benzenesulphonamide, trifluoroacetate Colourless oil (yield=26%).
$^1$H NMR (300 MHz, DMSO) δ: 8.12 (m broad, 1H); 6.81 (s, 2H); 4.40 (m, 1H); 4.09 (q, 2H); 3.80 (s, 3H); 3.78 (m, 1H); 3.54 (t, 2H); 3.24 (t, 2H); 3.15 (m, 4H); 2.97 (d, 2H); 2.84 (t, 1H); 2.70 (s, 3H); 2.53 (s, 6H); 2.41 (m, 1H); 1.64 (m, 2H); 1.42 (m, 1H); 1.25 (m, 2H); 1.22 (t, 6H); 0.96 (s, 6H).

EXAMPLE 113

4-methoxy-N,2,6-trimethyl-N-[2-[2-[4-(dimethylamino)methyl]-1-piperidinyl]-2-oxoethoxy]ethyl]benzenesulphonamide, fumarate White solid (yield=63%).
M.Pt.=65° C.

EXAMPLE 114

4-methoxy-N,2,6-trimethyl-N-[2-[2-[4-[(1-azetidinyl)methyl]-1-piperidinyl]-2-oxoethoxy]ethyl]benzenesulphonamide, fumarate White solid (yield=60%).
M.Pt.=75° C.

EXAMPLE 115

N,2,4,6-tetramethyl-N-[2-[2-[4-(1-methyl-4-piperidinyl)-1-piperidinyl]-2-oxoethoxy]ethyl]benzenesulphonamide, trifluoroacetate Colourless oil (yield=97%).
$^1$H NMR (250 MHz, CD3CN) δ: 9.40 (m broad, 1H) 6.97 (s, 2H); 4.98 (m, 1H); 4.09 (q, 2H); 3.71 (m, 1H); 3.57 (t, 2H); 3.45 (d, 2H); 3.28 (t, 2H); 2.85 (m, 1H); 2.80 (m, 2H); 2.77 (s, 3H); 2.72 (d, 3H); 2.56 (s, 6H); 2.45 (m, 1H); 2.28 (s, 3H); 1.92 (m, 2H); 1.71 (m, 2H); 1.50 (m, 2H); 1.34 (m, 2H); 1.09 (m, 2H).

EXAMPLE 116

N-methyl-N-[2-[2-[4-(1-methyl-4-piperidinyl)-1-piperidinyl]-2-oxoethoxy]ethyl]-2-trifluoromethyl-benzenesulphonamide, trifluoroacetate Colourless oil (yield=98%).
$^1$H NMR (300 MHz, CD3CN) δ: 8.50 (m broad, 1H); 7.97 (m, 2H); 7.77 (m, 2H); 4.48 (m, 1H); 4.13 (q, 2H); 3.80 (m, 1H); 3.64 (m, 2H); 3.49 (t, 2H); 3.42 (m, 2H); 2.96 (s, 3H);

2.90 (m, 1H); 2.78 (m, 2H); 2.72 (d, 3H); 2.50 (m, 1H); 1.93 (m, 2H); 1.73 (m, 2H); 1.38 (m, 4H); 1.36 (m, 2H).

EXAMPLE 117

4-methoxy-N-methyl-N-[2-[2-[4-(1-methyl-4-piperidinyl]-1-piperidinyl]-2-oxoethoxy]ethyl]-2-trifluoromethylbenzenesulphonamide, trifluoroacetate Colourless oil (yield=95%).
$^1$H NMR (300 MHz, CD3CN) δ: 8.41 (m broad, 1H); 7.96 (d, 1H); 7.40 (d, 1H); 7.25 (dd, 1H); 4.45 (m, 1H); 4.10 (q, 2H); 3.91 (s, 3H); 3.80 (m, 1H); 3.61 (t, 2H); 3.42 (m, 4H); 2.90 (s, 3H); 2.89 (m, 1H); 2.79 (m, 2H); 2.73 (d, 3H); 2.50 (m, 1H); 1.92 (m, 2H); 1.73 (m, 2H); 1.37 (m, 4H); 1.07 (m, 2H).

EXAMPLE 118

N,2,4,6-tetramethyl-N-[2-[2-[4-[2-(1-pyrrolidinyl) ethyl]-1-piperidinyl]-2-oxoethoxy]ethyl]benzenesulphonamide, trifluoroacetate Colourless oil (yield=99%).
$^1$H NMR (300 MHz, CD3CN) δ: 8.40 (m broad, 1H); 7.03 (s, 2H); 4.37 (m, 1H); 4.02 (q, 2H); 3.75 (m, 1H); 3.58 (m, 4H); 3.31 (t, 2H); 3.10 (m, 2H); 2.91 (m, 3H); 2.75 (s, 3H); 2.56 (s, 6H); 2.54 (m, 1H); 2.29 (s, 3H); 2.10 (m, 4H); 1.61 (m, 5H); 1.10 (m, 2H).

EXAMPLE 119

2,6-dichloro-4-methoxy-N-methyl-N-[2-[2-[4-(1-methyl-4-piperazinyl)-1-piperidinyl]-2-oxoethoxy] ethyl]benzenesulphonamide, difumarate White solid (yield=76%).
M.Pt.=176° C.

EXAMPLE 120

4-methoxy-N,2,6-trimethyl-N-[2-[2-[4-[2-(dimethylamino)ethyl]-1-piperidinyl]-2-oxoethoxy]-ethyl] benzenesulphonamide, fumarate A solution is prepared of 200 mg (0.6 mM) of acid obtained according to preparation III in 2 ml of chloroform and 0.2 ml of dimethylformamide and 0.12 ml of oxalyl chloride are added at ambient temperature. The mixture is agitated for 1 hour at ambient temperature and concentrated under reduced pressure. The residue is taken up into 3 ml of chloroform, and 103 mg (0.66 mM) of N,N-dimethyl-4-piperidineethanamine and 92 μl of triethylamine are added, and agitation is carried out for 2 hours at ambient temperature. The reaction mixture is concentrated under reduced pressure and the residue is purified by silica gel chromatography in eluting with the aid of a dichloromethane/methanol/aqueous ammonia mixture (95/5/0.5; v/v/v). 247 mg of amide are obtained as an oil which is salified with fumaric acid according to the method applied in Example 73 to obtain the salt as a white solid (yield=83%).
M.Pt.=55° C.

EXAMPLE 121

4-methoxy-N,2,6-trimethyl-N-[2-[2-[4-(4-cyclopropyl-1-piperazinyl)-1-piperidinyl]-2-oxoethoxy]ethyl] benzenesulphonamide, fumarate 2.2 g of tetrafluorophenol resin are placed in suspension in 10 ml of dimethylformamide and 40 ml of dichloromethane and 50 mg of 4-dimethylaminopyridine, 0.66 ml of diisopropylcarbodiimide and 1 g (3.1 mM) of acid obtained according to preparation III, are added. The mixture is agitated at ambient temperature for 16 hours, and then the resin is separated off by filtration and reallowed to react in 40 ml of dichloromethane with 0.5 g (2.39 mM) of 1-cyclopropyl-4-(4-piperidinyl)piperazine, for 2 hours at ambient temperature. The reaction mixture is filtered and the filtrate is concentrated under reduced pressure. The crude product obtained is purified by silica gel chromatography in eluting with the aid of a dichloromethane/methanol mixture (99/1; v/v). 700 mg of amide are obtained as an oil which is salified with fumaric acid according to the method applied in Example 73 to obtain the salt as a white solid (yield=49%).
M.Pt.=80° C.
In operating analogously to Example 121, starting with the amines obtained according to preparations LXXXVIII and LXXIV, the following compounds according to the invention are obtained:

EXAMPLE 122

4-methoxy-N,2,6-trimethyl-N-[2-[2-[4-[4-(1,1-dimethylethyl)-1-piperazinyl]-1-piperidinyl]-2-oxoethoxy]ethyl]benzenesulphonamide, difumarate White solid (yield=48%)
M.Pt.=170° C.

EXAMPLE 123

4-methoxy-N,2,6-trimethyl-N-[2-[2-[4-[(4-methyl-1-piperazinyl)methyl]-1-piperidinyl]-2-oxoethoxy] ethyl]benzenesulphonamide, difumarate White solid (yield=39%)
M.Pt.=168° C.
In operating analogously to Examples 70 and 73, starting with the amine obtained according to preparation CVII, the following compound according to the invention is obtained

EXAMPLE 124

4-methoxy-N,2,6-trimethyl-N-[2-[2-[4-[2-(4-methyl-1-piperazinyl)ethyl]-1-piperidinyl]-2-oxoethoxy] ethyl]benzenesulphonamide, difumarate White solid (yield=59%)
M.Pt.=178-179° C.

PREPARATION CXLVII 4-methoxy-N,2,6-trimethyl-N-[2-[2-[4-(3-hydroxypropyl)-1-piperidinyl]-2-oxoethoxy]ethyl]benzenesulphonamide In operating analogously to Example 72, starting with 3-(4-piperidinyl)propanol, the product sought after is obtained as a colourless oil (yield=79%).

¹H NMR (300 MHz, DMSO) δ: 6.80 (s, 2H); 4.34 (t, 1H); 4.28 (dm, 1H); 4.03 (m, 2H); 3.79 (s, 3H); 3.64 (dm, 1H); 3.53 (t, 2H); 3.37 (d, 2H); 3.21 (t, 2H); 2.86 (t, 1H); 2.70 (s, 3H); 2.53 (s, 6H); 2.45 (m, 1H); 1.63 (d, 2H); 1.40 (m, 3H); 1.19 (m, 2H); 0.93 (m, 2H).

PREPARATION CXLVIII 4-methoxy-N,2,6-trimethyl-N-[2-[2-[4-[3-[[(4-methylphenyl)sulphonyl]oxy]propyl]-1-piperidinyl]-2-oxoethoxy]ethyl]-benzenesulphonamide A solution is prepared of 6.8 g (14.9 mM) of the compound obtained according to preparation CXLVII in 50 ml of dichloromethane and, at ambient temperature, 3.4 ml (24.6 mM) of triethylamine, and then 4.68 g (24.6 mM) of tosyl chloride and 142 mg (1.5 mM) of trimethylamine hydrochloride, are added. The mixture is agitated for 4 hours under reflux of the solvent and then cooled and hydrolysed on 50 ml of water. The organic phase is washed with water, dried over magnesium sulphate and concentrated under reduced pressure. The residue is purified by silica gel chromatography in eluting with the aid of an ethyl acetate/toluene mixture (8/2; v/v). 5.6 g of the compound sought after are obtained as a colourless oil (yield=62%).
¹H NMR (300 MHz, DMSO) δ: 7.79 (dd, 2H); 7.48 (d, 2H); 6.80 (s, 2H); 4.26 (m, 1H); 4.00 (m, 3H); 3.79 (s, 3H); 3.62 (t, 2H); 3.51 (m, 2H); 3.23 (m, 2H); 2.85 (m, 1H); 2.70 (s, 3H); 2.53 (s, 6H); 2.45 (m, 1H); 2.41 (s, 3H); 1.55 (m, 3H); 1.29 (m, 2H); 1.13 (m, 2H); 0.89 (m, 2H).

EXAMPLE 125

4-methoxy-N,2,6-trimethyl-N-[2-[2-[4-[3-(4-morpholinyl)-propyl]-1-piperidinyl]-2-oxoethoxy]ethyl] benzenesulphonamide A solution is prepared of 400 mg (0.65 mM) of the compound obtained according to preparation CXLVIII in 8 ml of dimethylformamide and, at ambient temperature, 90 mg (0.65 mM) of potassium carbonate, and then 95 μl (1 mM) of morpholine, are added. The mixture is agitated for 16 hours at 60° C. and then cooled, hydrolysed on 20 ml of water and extracted with ethyl acetate. The organic phase is washed with water, dried over magnesium sulphate and concentrated under reduced pressure. The residue is purified by silica gel chromatography in eluting with the aid of a dichloromethane/methanol mixture (98/2; v/v). 150 mg of the compound sought after are obtained as a colourless oil (yield=44%).
¹H NMR (300 MHz, DMSO) δ: 6.80 (s, 2H); 4.27 (m, 1H); 4.05 (q, 2H); 3.79 (s, 3H); 3.70 (m, 1H); 3.54 (m, 6H); 3.21 (t, 2H); 2.85 (m, 1H); 2.70 (s, 3H); 2.53 (s, 6H); 2.42 (m, 1H); 2.31 (m, 4H); 2.22 (t, 2H); 1.65 (m, 2H); 1.41 (m, 3H); 1.36 (m, 2H); 0.96 (m, 2H).

EXAMPLE 126

4-methoxy-N,2,6-trimethyl-N-[2-[2-[4-[3-(4-morpholinyl)-propyl]-1-piperidinyl]-2-oxoethoxy]ethyl] benzenesulphonamide, fumarate In operating analogously to Example 73, starting with the compound obtained according to Example 125, the product sought after is obtained as a white solid (yield=99%).
M.Pt.=50° C.

In operating analogously to Examples 125 and 126, starting with various amines, the following compounds according to the invention are obtained:

EXAMPLE 127

4-methoxy-N,2,6-trimethyl-A[2-[2-[4-[3-(1-pyrrolidinyl)propyl]-1-piperidinyl]-2-oxoethoxy]ethyl]-benzenesulphonamide Colourless oil (yield=53%).
¹H NMR (300 MHz, DMSO) δ: 6.80 (s, 2H); 4.30 (m, 1H); 4.06 (q, 2H); 3.80 (s, 3H); 3.68 (m, 1H); 3.53 (t, 2H); 3.20 (t, 2H); 2.90 (m, 1H); 2.71 (s, 3H); 2.61 (m, 6H); 2.53 (s, 6H); 2.48 (m, 1H); 1.75 (s, 4H); 1.62 (m, 2H); 1.48 (m, 2H); 1.42 (m, 1H); 1.21 (m, 2H); 0.92 (m, 2H).

EXAMPLE 128

4-methoxy-N,2,6-trimethyl-N-[2-[2-[4-[3-(1-pyrrolidinyl)propyl]-1-piperidinyl]-2-oxoethoxy]ethyl] benzenesulphonamide, fumarate White solid (yield=92%).
M.Pt.=50° C.

EXAMPLE 129

4-methoxy-N,2,6-trimethyl-N-[2-[2-[4-[3-(hexahydro-4-methyl-1H-1,4-diazepin-1-yl)propyl]-1-piperidinyl]-2-oxoethoxy]ethyl]benzenesulphonamide Colourless oil (yield=27%).
¹H NMR (300 MHz, DMSO) δ: 6.80 (s, 2H); 4.29 (m, 1H); 4.05 (q, 2H); 3.79 (s, 3H); 3.65 (m, 1H); 3.50 (t, 2H); 3.23 (t, 2H); 2.85 (m, 1H); 2.69 (s, 3H); 2.57 (m, 8H); 2.46 (t, 2H); 2.34 (s, 3H); 1.65 (m, 4H); 1.37 (m, 3H); 1.17 (m, 2H); 0.95 (m, 2H).

EXAMPLE 130

4-methoxy-N,2,6-trimethyl-N-[2-[2-[4-[3-(hexahydro-4-methyl-1H-1,4-diazepin-1-yl)propyl]-1-piperidinyl]-2-oxoethoxy]ethyl]benzenesulphonamide, difumarate White solid (yield=41%).
M.Pt.=174° C.

EXAMPLE 131

4-methoxy-N,2,6-trimethyl-N-[2-[2-[4-[3-(4-methyl-1-piperazinyl)propyl]-1-piperidinyl]-2-oxoethoxy]ethyl]benzenesulphonamide Colourless oil (yield=43%).
¹H NMR (300 MHz, DMSO) δ: 6.80 (s, 2H); 4.27 (m, 1H); 4.03 (q, 2H); 3.79 (s, 3H); 3.65 (m, 1H); 3.52 (t, 2H); 3.23 (t, 2H); 2.85 (m, 1H); 2.69 (s, 3H); 2.53 (s, 6H); 2.48 (m, 1H); 2.29 (m, 8H); 2.23 (t, 2H); 2.12 (s, 3H); 1.63 (m, 2H); 1.38 (m, 3H); 1.17 (m, 2H); 0.95 (m, 2H).

EXAMPLE 132

4-methoxy-N,2,6-trimethyl-N-[2-[2-[4-[3-(4-methyl-1-piperazinyl)propyl]-1-piperidinyl]-2-oxoethoxy]ethyl]benzenesulphonamide, difumarate White solid (yield=89%).
M.Pt.=174° C.

EXAMPLE 133

4-methoxy-N,2,6-trimethyl-N-[2-[2-[4-[3-(1-azetidinyl)propyl]-1-piperidinyl]-2-oxoethoxy]ethyl]benzenesulphonamide Colourless oil (yield=23%).

$^1$H NMR (300 MHz, DMSO) δ: 6.80 (s, 2H), 4.26 (m, 1H); 4.02 (q, 2H); 3.80 (s, 3H); 3.68 (m, 1H); 3.54 (t, 2H); 3.21 (t, 2H); 3.03 (t, 4H); 2.85 (m, 1H); 2.70 (s, 3H); 2.53 (s, 6H); 2.48 (m, 2H); 2.47 (m, 1H); 2.25 (t, 2H); 1.91 (quin, 2H); 1.60 (m, 2H); 1.40 (m, 1H); 1.18 (m, 4H); 0.89 (m, 2H).

EXAMPLE 134

4-methoxy-N,2,6-trimethyl-N-[2-[2-[4-[3-(1-azetidinyl)propyl]-1-piperidinyl]-2-oxoethoxy]ethyl]benzenesulphonamide, fumarate White solid (yield=93%).
M.Pt.=65° C.

EXAMPLE 135

4-methoxy-N,2,6-trimethyl-N-[2-[2-[4-[3-(dimethylamino)-propyl]-1-piperidinyl]-2-oxoethoxy]ethyl]benzenesulphonamide Colourless oil (yield=23%).

$^1$H NMR (250 MHz, DMSO) δ: 6.80 (s, 2H); 4.30 (m, 1H); 4.02 (q, 2H); 3.79 (s, 3H); 3.65 (m, 1H); 3.52 (t, 2H); 3.21 (t, 2H); 2.85 (m, 1H); 2.70 (s, 3H); 2.53 (s, 6H); 2.44 (m, 1H); 2.14 (t, 2H); 2.09 (s, 6H); 1.60 (m, 2H); 1.38 (m, 3H); 1.17 (m, 2H); 0.91 (m, 2H).

EXAMPLE 136

4-methoxy-N,2,6-trimethyl-N-[2-[2-[4-[3-(dimethylamino)-propyl]-1-piperidinyl]-2-oxoethoxy]ethyl]-benzenesulphonamide, fumarate White solid (yield=99%).
M.Pt.=55° C.

PREPARATION CIL

1'-[[2-[[(4-methoxy-2,6-dimethylphenyl)sulphonyl]methylamino]ethoxy]acetyl][4,4'-bipiperidine]-1-carboxylic acid, 1,1-dimethylethyl ester In operating analogously to Example 72, starting with the compound obtained according to preparation LXXXIX, the product sought after is obtained as a colourless oil (yield=88%).

$^1$H NMR (250 MHz, DMSO) δ: 6.80 (s, 2H); 4.39 (m, 1H); 3.98 (m, 4H); 3.79 (s, 3H); 3.70 (m, 1H); 3.53 (t, 2H); 3.20 (t, 2H); 2.85 (m, 1H); 2.69 (s, 3H); 2.61 (m, 2H); 2.53 (s, 6H); 2.43 (m, 1H); 1.62 (m, 4H); 1.38 (s, 9H); 1.23 (m, 2H); 1.01 (m, 4H).

EXAMPLE 137

N-[2-(2-[4,4'-bipiperidin]-1-yl-2-oxoethoxy)ethyl]-4-methoxy-N,2,6-trimethyl-benzenesulphonamide, trifluoroacetate In operating analogously to preparation CXXI, starting with the compound obtained according to preparation CIL, the product sought after is obtained as a white foam (yield=99%).

$^1$H NMR (250 MHz, CD3CN) δ: 7.00 (m broad, 1H); 6.74 (s, 2H); 4.48 (m, 1H); 4.05 (q, 2H); 3.80 (s, 3H); 3.75 (m, 1H); 3.57 (t, 2H); 3.35 (m, 2H); 3.30 (t, 2H), 2.92 (m, 3H); 2.74 (s, 3H); 2.57 (s, 6H); 2.48 (m, 1H); 1.89 (m, 2H); 1.71 (m, 2H); 1.43 (m, 4H); 1.10 (m, 2H).

PREPARATION CL

[2-[1-[[2-[[(4-methoxy-2,6-dimethylphenyl)sulphonyl]methylamino]ethoxy]acetyl]-4-piperidinyl]ethyl]methyl-carbamic acid, 1,1-dimethylethyl ester In operating analogously to Example 72, starting with the compound obtained according to preparation CXIV, the product sought after is obtained as a colourless oil (yield=82%).

$^1$H NMR (250 MHz, DMSO) δ: 6.80 (s, 2H); 4.32 (m, 1H); 4.04 (q, 2H); 3.80 (s, 3H); 3.69 (m, 1H); 3.56 (t, 2H); 3.21 (t, 2H); 3.19 (m, 2H); 2.85 (m, 1H); 2.74 (s, 3H); 2.70 (s, 3H); 2.53 (s, 6H); 2.46 (m, 1H); 1.65 (m, 2H); 1.38 (s, 9H); 1.34 (m, 3H); 1.01 (m, 2H).

EXAMPLE 138

4-methoxy-N,2,6-trimethyl-N-[2-[2-[4-[2-(methylamino)ethyl]-1-piperidinyl]-2-oxoethoxy]ethyl]benzenesulphonamide In operating analogously to preparation XXIX, starting with the compound obtained according to preparation CL, the product sought after is obtained as a colourless oil (yield=99%).

$^1$H NMR (250 MHz, DMSO) δ: 6.80 (s, 2H); 4.25 (m, 1H); 4.05 (q, 2H); 3.80 (s, 3H); 3.65 (m, 1H); 3.55 (t, 2H); 3.19 (t, 2H); 2.85 (m, 1H); 2.70 (s, 3H); 2.51 (s, 6H); 2.48 (m, 3H); 2.24 (s, 3H); 1.59 (m, 2H); is 1.52 (m, 1H); 1.34 (m, 2H); 0.92 (m, 2H).

EXAMPLE 139

4-methoxy-N,2,6-trimethyl-N-[2-[2-[4-[2-(methylamino)ethyl]-1-piperidinyl]-2-oxoethoxy]ethyl]benzenesulphonamide, fumarate In operating analogously to Example 73, starting with the compound obtained according to Example 138, the product sought after is obtained as a white solid (yield=99%).
M.Pt.=50° C.

PREPARATION CLI

[1-[[2-[[(4-methoxy-2,6-dimethylphenyl)sulphonyl]methylamino]ethoxy]acetyl]-4-piperidinyl]carbamic acid, 1,1-dimethylethyl ester In operating analogously to Example 72, starting with t-butyl(4-piperidinyl)carbamate, the product sought after is obtained as a colourless oil (yield=66%).

¹H NMR (250 MHz, DMSO) δ: 6.80 (s, 2H); 4.07 (m, 1H); 4.04 (m, 2H); 3.80 (s, 3H); 3.52 (m, 4H); 3.22 (t, 2H); 2.95 (m, 1H); 2.70 (s, 3H); 2.67 (m, 1H); 2.53 (s, 6H); 1.72 (m, 2H); 1.38 (s, 9H); 1.26 (m, 2H).

EXAMPLE 140

N-[2-[2-(4-amino-1-piperidinyl)-2-oxoethoxy]ethyl]-4-methoxy-N,2,6-trimethyl-benzenesulphonamide In operating analogously to preparation XXIX, starting with the compound obtained according to preparation CL, the product sought after is obtained as a yellow oil (yield=86%).

¹H NMR (300 MHz, DMSO) δ: 6.80 (s, 2H); 4.13 (m, 1H); 4.05 (m, 2H); 3.80 (s, 3H); 3.60 (m, 1H); 3.55 (t, 2H); 3.46 (m broad, 2H); 3.22 (t, 2H); 2.89 (m, 2H); 2.70 (s, 3H); 2.67 (m, 1H); 2.53 (s, 6H); 1.74 (m, 2H); 1.51 (m, 2H).

EXAMPLE 141

4-methoxy-N,2,6-trimethyl-N-[2-[2-[4-[(8-methyl-8-azabicyclo[3.2.1]oct-3-yl)amino]-1-piperidinyl]-2-oxoethoxy]ethyl]benzenesulphonamide In operating analogously to preparation LXXI, starting with the compound obtained according to Example 140, the product sought after is obtained as a colourless oil (yield=40%).

¹H NMR (250 MHz, DMSO) δ: 6.80 (s, 2H); 4.13 (m, 1H); 4.05 (m, 2H); 3.79 (s, 3H); 3.65 (m, 1H); 3.50 (t, 2H); 3.22 (t, 2H); 2.91 (m, 4H); 2.70 (s, 3H); 2.60 (m, 2H); 2.51 (s, 6H); 1.85 (m, 8H); 1.45 (m, 2H); 0.96 (m, 2H).

EXAMPLE 142

4-methoxy-N,2,6-trimethyl-N-[2-[2-[4-[(8-methyl-8-azabicyclo[3.2.1]oct-3-yl)amino]-1-piperidinyl]-2-oxoethoxy]-ethyl]benzenesulphonamide, bis(trifluoroacetate)

A mixture of 140 mg (0.26 mM) of the compound obtained according to Example 141 is agitated until dissolution in 4 ml of a solution of 6% trifluoroacetic acid in water. The solution is frozen and freeze-dried and 200 mg of the product sought after are thus obtained as a white solid (quantitative yield).

M.Pt.=70° C.

In operating analogously to preparation CLI and to Examples 140 to 142, starting with t-butyl methyl(4-piperidinyl)carbamate, the following compounds are obtained:

PREPARATION CLII

[1-[[2-[[(4-methoxy-2,6-dimethylphenyl)sulphonyl]methylamino]ethoxy]acetyl]-4-piperidinyl]methylcarbamic acid, 1,1-dimethylethyl ester Colourless oil (yield=49%).

¹H NMR (300 MHz, DMSO) δ: 6.80 (s, 2H); 4.38 (m, 1H); 4.32 (m, 1H); 4.07 (m, 2H); 4.01 (m, 1H); 3.80 (s, 3H); 3.74 (m, 1H); 3.54 (m, 2H); 3.23 (t, 2H); 2.93 (m, 2H); 2.70 (s, 3H); 2.63 (s, 3H); 2.53 (s, 6H); 1.53 (m, 4H); 1.39 (s, 9H).

EXAMPLE 143

4-methoxy-N,2,6-trimethyl-N-[2-[2-[4-(methylamino)-1-piperidinyl]-2-oxoethoxy]ethyl]-benzenesulphonamide Colourless oil (yield=99%).

¹H NMR (250 MHz, DMSO) δ: 6.80 (s, 2H); 4.18 (m, 1H); 4.08 (m, 2H); 3.80 (s, 3H); 3.68 (m, 1H); 3.54 (t, 2H); 3.23 (t, 2H); 2.95 (m, 1H); 2.85 (m, 1H); 2.70 (s, 3H); 2.67 (m, 1H); 2.53 (s, 6H); 2.42 (s, 3H); 1.85 (m, 2H); 1.25 (m, 2H).

EXAMPLE 144

4-methoxy-N,2,6-trimethyl-N-[2-[2-[4-[methyl(8-methyl-8-azabicyclo[3.2.1]oct-3-yl)amino]-1-piperidinyl]-2-oxoethoxy]ethyl]benzenesulphonamide Colourless oil (yield=34%).

¹H NMR (300 MHz, DMSO) δ: 6.80 (s, 2H); 4.30 (m, 1H); 4.10 (q, 2H); 3.80 (s, 3H); 3.67 (m, 1H); 3.52 (t, 2H); 3.30 (m, 2H); 3.21 (t, 2H); 2.88 (m, 1H); 2.75 (m, 2H); 2.70 (s, 3H); 2.53 (s, 6H); 2.49 (m, 1H); 2.14 (s, 3H); 2.05 (s, 3H); 1.89 (m, 2H); 1.45 (m, 8H); 1.23 (m, 2H).

EXAMPLE 145

4-methoxy-N,2,6-trimethyl-N-[2-[2-[4-[methyl(8-methyl-8-azabicyclo[3.2.1]oct-3-yl)amino]-1-piperidinyl]-2-oxoethoxy]ethyl]benzenesulphonamide, bis(trifluoroacetate)

Colourless oil (yield=99%).

¹H NMR (250 MHz, CD3CN) δ: 6.75 (s, 2H); 4.62 (m, 1H); 4.06 (m, 2H); 3.97 (m, 2H); 3.92 (m, 1H); 3.81 (s, 3H); 3.65 (m, 1H); 3.59 (m, 3H); 3.30 (t, 2H); 3.05 (m, 1H); 2.74 (s, 3H); 2.71 (d, 3H); 2.63 (s, 3H); 2.70-2.55 (m, 3H); 2.53 (s, 6H); 2.27 (m, 4H); 1.97 (m, 4H); 1.62 (m, 2H).

PREPARATION CLIII

4-[[1-[(1,1-dimethylethoxy)carbonyl]-4-piperidinyl]methyl]-1-piperazinecarboxylic acid, phenylmethyl ester In operating analogously to preparation LXXI, starting with the t-butyl ester of 4-formyl-1-piperidinecarboxylic acid and with the benzyl ester of 1-piperazinecarboxylic acid, the product sought after is obtained as a colourless oil (yield=26%).

¹H NMR (300 MHz, DMSO) δ: 7.31 (m, 5H); 5.11 (s, 2H); 3.90 (m, 2H); 3.64 (m, 4H); 2.75 (m, 8H); 1.89 (m, 1H); 1.70 (m, 2H); 1.39 (s, 9H); 1.04 (m, 2H).

PREPARATION CLIV 4-(4-piperidinylmethyl)-1-piperazinecarboxylic acid, phenylmethyl ester In operating analogously to preparation XXIX, starting with the compound obtained according to preparation CLIII, the product sought after is obtained as a colourless oil (yield=83%).

¹H NMR (250 MHz, DMSO) δ: 7.35 (m, 5H); 5.00 (s, 2H); 3.35 (m, 4H); 2.95 (m, 2H); 2.46 (m, 2H); 2.30 (m, 4H); 2.11 (m, 2H); 1.65 (m, 3H); 0.98 (m, 2H).

PREPARATION CLV

4-[[1-[[2-[[(4-methoxy-2,6-dimethylphenyl)sulphonyl]methylamino]ethoxy]acetyl]-4-piperidinyl]methyl]-1-piperazinecarboxylic acid, phenylmethyl ester In operating analogously to Example 72, starting with the compound obtained according to preparation CLIV, the product sought after is obtained as a colourless oil (yield=70%).

$^1$H NMR (250 MHz, DMSO) δ: 7.35 (m, 5H); 6.80 (s, 2H); 5.07 (s, 2H); 4.25 (m, 1H); 4.05 (m, 2H); 3.79 (s, 3H); 3.68 (m, 1H); 3.53 (t, 2H); 3.30 (m, 4H); 3.21 (t, 2H); 2.88 (m, 1H); 2.69 (s, 3H); 2.53 (s, 6H); 2.51 (m, 1H); 2.31 (m, 4H); 2.27 (m, 2H); 1.70 (m, 3H); 0.95 (m, 2H).

EXAMPLE 146

4-methoxy-N,2,6-trimethyl-N-[2-[2-oxo-2-[4-(1-piperazinyl-methyl)-1-piperidinyl]ethoxy]ethyl]benzenesulphonamide In operating analogously to preparation XXXV, starting with the compound obtained according to preparation CLV, the product sought after is obtained as a colourless oil (yield=93%).

$^1$H NMR (300 MHz, DMSO) δ: 6.80 (s, 2H); 4.25 (m, 1H); 4.05 (q, 2H); 3.79 (s, 3H); 3.54 (m, 1H); 3.51 (t, 2H); 3.23 (t, 2H); 2.87 (m, 1H); 2.70 (s, 3H); 2.66 (m, 4H); 2.53 (s, 6H); 2.50 (m, 1H); 2.46 (m, 4H); 2.05 (d, 2H); 1.74 (m, 3H); 0.98 (m, 2H).

EXAMPLE 147

4-methoxy-N,2,6-trimethyl-N-[2-[2-oxo-2-[4-(1-piperazinyl-methyl)-1-piperidinyl]ethoxy]ethyl]benzenesulphonamide, fumarate In operating analogously to Example 73, starting with the compound obtained according to Example 146, the product sought after is obtained as a white solid (yield=93%).

M.Pt.=85-87° C.

PREPARATION CLVI

1-[[2-[[(4-methoxy-2,6-dimethylphenyl)sulphonyl]methylamino]ethoxy]acetyl]-4-piperidinecarboxylic acid, ethyl ester In operating analogously to Example 70, starting with the ethyl ester of 4-piperidinecarboxylic acid, the product sought after is obtained as a colourless oil (yield=89%).

$^1$H NMR (250 MHz, DMSO) δ: 6.80 (s, 2H); 4.17 (m, 5H); 3.80 (s, 3H); 3.65 (m, 1H); 3.53 (t, 2H); 3.29 (s, 3H); 3.21 (t, 2H); 2.99 (m, 1H); 2.72 (m, 1H); 2.70 (s, 3H); 2.58 (m, 1H); 2.53 (s, 6H); 1.83 (m, 2H); 1.44 (m, 2H); 1.20 (t, 3H).

PREPARATION CLVII

1-[[2-[[(4-methoxy-2,6-dimethylphenyl)sulphonyl]methylamino]ethoxy]acetyl]-4-piperidinecarboxylic acid A solution is prepared of 2.3 g (4.89 mM) of ester obtained according to preparation CLVI in 40 ml of tetrahydrofuran and a solution of 246 mg (5.8 mM) of lithia in 3 ml of water is added. The mixture is agitated at ambient temperature overnight and then concentrated under reduced pressure. The residue is taken up into 25 ml of water, acidified up to pH 2 with an N solution of hydrochloric acid and extracted with ethyl acetate. The organic phase is dried over magnesium sulphate and concentrated under reduced pressure. The crude product is purified by silica gel chromatography in eluting with the aid of a dichloromethane/methanol mixture (95/5; v/v). 1.6 g of the compound sought after are obtained as a colourless oil (yield=74%).

$^1$H NMR (300 MHz, DMSO) δ: 6.80 (s, 2H); 4.10 (m, 1H); 4.06 (m, 2H); 3.79 (s, 3H); 3.55 (m, 1H); 3.53 (t, 2H); 3.23 (t, 2H); 2.98 (m, 1H); 2.74 (m, 1H); 2.70 (s, 3H); 2.53 (s, 3H); 2.50 (s, 6H); 2.43 (m, 1H); 1.85 (m, 2H); 1.40 (m, 2H).

EXAMPLE 148

4-methoxy-N,2,6-trimethyl-N-[2-[2-oxo-2-[4-[1-oxo-2-(4-methyl-1-piperazinyl)ethyl]-1-piperidinyl]ethoxy]-ethyl]benzenesulphonamide, bis(trifluoroacetate)

A solution is prepared of 0.65 g (1.47 mM) of acid obtained according to preparation CLVII in 20 ml of dichloromethane and 0.25 ml of oxalyl chloride are added. The mixture is agitated for 2 hours at ambient temperature and is concentrated under reduced pressure. The yellow oil obtained is taken up into 8 ml of tetrahydrofuran and 8 ml of acetonitrile and, at 0° C., 0.74 ml (1.47 mM) of a 2M solution of trimethylsilyldiazomethane in hexane are added. The mixture is agitated 1 hour at ambient temperature and then concentrated under reduced pressure. The residue is taken up into solution in 10 ml of chloroform and is added dropwise to a solution of 147 mg (1.47 mM) of N-methylpiperazine in 10 ml of chloroform, in the presence of 10 mg of chlorocyclopentadienyl-bis(triphenylphosphine)ruthenium(II), at 60° C. The reaction mixture is agitated at 60° C. for 30 min and then concentrated under reduced pressure. The crude product is purified by silica gel chromatography in eluting with the aid of a dichloromethane/methanol mixture (85/15; v/v). The oily product obtained is salified directly trifluoroacetic acid in applylng the procedure described in Example 142. 0.167 g of the compound sought after are obtained as a colourless oil (yield=21%).

$^1$H NMR (300 MHz, CD3CN) δ: 6.75 (s, 2H); 4.35 (m, 1H); 4.04 (m, 2H); 3.83 (s, 3H); 3.81 (s, 2H); 3.70 (m, 1H); 3.58 (t, 2H); 3.38 (m, 4H); 3.30 (t, 2H); 3.22 (m, 4H); 2.95 (m, 1H); 2.81 (s, 3H); 2.74 (s, 3H); 2.69 (m, 2H); 2.56 (s, 6H); 1.80 (m, 2H); 1.45 (m, 2H).

EXAMPLE 149

4-methoxy-N,2,6-trimethyl-N-[2-[2-[4-(1-methyl-4-piperidinyl)]-1-piperazinyl]-2-oxoethoxy]ethyl]benzenesulphonamide A solution is prepared of 7 g (21 mM) of acid obtained according to preparation III in 50 ml of chloroform and 0.1 ml of dimethylformamide and, at ambient temperature, a solution of 3.7 ml (42 mM) of oxalyl chloride in 8 ml of chloroform, is added dropwise. The reaction mixture is agitated for 3 hours at ambient temperature and concentrated under reduced pressure. The residue from evaporation is taken up into 20 ml of chloroform and is added slowly, at 0° C., to a solution of 4.04 g (22 mM) of 1-(1-methyl-4-piperidinyl) piperazine and 8.7 ml of triethylamine in 40 ml of chloroform. The reaction mixture is agitated for 1 hour at 0° C. and then poured over 60 ml of iced water. The mixture obtained is extracted with 100 ml of chloroform and the organic phase is washed with a solution of sodium bicarbonate, and then with water, dried over magnesium sulphate and concentrated under reduced pressure. The product sought after is thus obtained as an oil (yield=81.7%) which is used, without other purification, to obtain a salt with an acid.

EXAMPLE 150

4-methoxy-N,2,6-trimethyl-N-[2-[2-[4-(1-methyl-4-piperidinyl)]-1-piperazinyl]-2-oxoethoxy]ethyl]benzenesulphonamide, dihydrochloride A solution is prepared of 6 g (12 mM) of the compound obtained according to Example 149 in 100 ml of ethanol heated to around 65° C. 3.2 ml (36 mM) of concentrated hydrochloric acid are then added, at around 60° C. A precipitate forms rapidly. After 2 hours under agitation at ambient temperature, the suspension is cooled to 0° C. and filtered on a sinter. The solid isolated is washed with 10 ml of cold ethanol and then with 15 ml of ethyl ether and dried under reduced pressure. 5.2 g of the salt sought after are thus obtained as a white solid (yield=75%).

M.Pt.>250° C.

EXAMPLE 151

4-methoxy-N,2,6-trimethyl-N-[2-[2-[4-(1-methyl-4-piperidinyl)]-1-piperazinyl]-2-oxoethoxy]ethyl]benzenesulphonamide, difumarate In operating analogously to Example 150, with 2.5 equivalents of fumaric acid, the product sought after is obtained as a white solid (yield=76%).

M.Pt.=185° C.

TABLE I

| EX | $R_1$ | $R_2$ | $R_3(R_4)$ | $R_a$ | X | p | A | B | Salt |
|---|---|---|---|---|---|---|---|---|---|
| 1 | 4-O—CH$_3$ | 2-CH$_3$ | 6-CH$_3$ | —CH$_3$ | N | 2 | (CH$_2$)$_2$ | N-methylpyrrolidinyl | 2TFA |
| 2 | 4-CH$_3$ | 2-CH$_3$ | 6-CH$_3$ | —CH$_3$ | N | 2 | Is | methyl-bicyclic amine | 2TFA |
| 3 | 4-CH$_3$ | 2-CH$_3$ | 6-CH$_3$ | —CH$_3$ | N | 2 | Is | methyl-bicyclic amine | — |
| 4 | 4-CH$_3$ | 2-CH$_3$ | 6-CH$_3$ | —CH$_3$ | N | 2 | Is | methyl-bicyclic amine | 2F |
| 5 | 4-CH$_3$ | 2-CH$_3$ | 6-CH$_3$ | —CH$_3$ | N | 2 | Is | methyl-bicyclic amine | — |
| 6 | 4-CH$_3$ | 2-CH$_3$ | 6-CH$_3$ | —CH$_3$ | N | 2 | Is | methyl-bicyclic amine | 1F |
| 7 | 4-CH$_3$ | 2-CH$_3$ | 6-CH$_3$ | —CH$_3$ | N | 2 | Is | methyl-bicyclic amine | 1F |
| 8 | 4-CH$_3$ | 2-CH$_3$ | 6-CH$_3$ | —CH$_3$ | N | 2 | (CH$_2$)$_3$ | N-methylpyrrolidinyl | 2TFA |
| 9 | 4-O—CH$_3$ | 2-CH$_3$ | 6-CH$_3$ | —CH$_3$ | N | 2 | (CH$_2$)$_2$ | morpholinyl | 2TFA |

TABLE I-continued

| EX | R₁ | R₂ | R₃(R₄) | Rₐ | X | p | A | B | Salt |
|---|---|---|---|---|---|---|---|---|---|
| 10 | 4-O—CH₃ | 2-CH₃ | 6-CH₃ | —CH₃ | N | 2 | (CH₂)₂ | N-methylpiperidine | 2TFA |
| 11 | 4-O—CH₃ | 2-CH₃ | 6-CH₃ | —CH₃ | N | 2 | (CH₂)₃ | N-methylpiperidine | 2TFA |
| 12 | 4-O—CH₃ | 2-CH₃ | 6-CH₃ | —CH₃ | N | 2 | (CH₂)₃ | —N(CH₃)₂ | 2TFA |
| 13 | 4-O—CH₃ | 2-CH₃ | 6-CH₃ | —CH₃ | N | 2 | Is | 4-methyl-1-methylpiperidine | 2TFA |
| 14 | 4-O—CH₃ | 2-CH₃ | 6-CH₃ | —CH₃ | N | 2 | Is | N-methyltropane | 1F |
| 15 | 4-O—CH₃ | 2-CH₃ | 6-CH₃ | —CH₃ | N | 3 | Is | methylquinuclidine | 1F |
| 16 | 4-O—CH₃ | 2-CH₃ | 6-CH₃ | —CH₃ | N | 2 | (CH₂)₃ | N-methylazetidine | 2F |
| 17 | 4-O—CH₃ | 2-CH₃ | 6-CH₃ | —CH₃ | N | 2 | Is | 3-methyl-1-methylpiperidine | 2F |
| 18 | 4-O—CH₃ | 2-CH₃ | 6-CH₃ | c-Pr | N | 2 | Is | 4-methyl-1-methylpiperidine | 2F |
| 19 | 4-O—CH₃ | 2-CH₃ | 6-CH₃ | c-Pr | N | 2 | (CH₂)₂ | N-methylpyrrolidine | 2F |
| 20 | 4-O—CH₃ | 2-CH₃ | 6-CH₃ | —CH₃ | N | 2 | —CH₂— | 1,2-dimethylimidazole | 2F |
| 21 | 4-O—CH₃ | 2-CH₃ | 6-CH₃ | —C₂H₅ | N | 2 | Is | 4-methyl-1-methylpiperidine | 2F |
| 22 | 4-O—CH₃ | 2-CH₃ | 6-CH₃ | —C₂H₅ | N | 2 | (CH₂)₃ | —N(CH₃)₂ | 2F |
| 23 | 4-O—CH₃ | 2-CH₃ | 6-CH₃ | —CH₃ | N | 2 | Is | N-methyltropane (stereo) | 1F |
| 24 | 4-O—CH₃ | 2-CH₃ | 6-CH₃ | —C₂H₅ | N | 2 | (CH₂)₃ | N-methylpyrrolidine | 2F |

TABLE I-continued
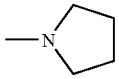
| EX | R₁ | R₂ | R₃(R₄) | R_α | X | p | A | B | Salt |
|---|---|---|---|---|---|---|---|---|---|
| 25 | 4-O—CH₃ | 2-CH₃ | 6-CH₃ | c-Pr | N | 2 | (CH₂)₃ |  | 2F |
| 26 | 4-O—CH₃ | 2-CH₃ | 6-CH₃ | —CH₃ | N | 2 | Is | 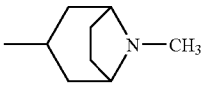 | 1F |
| 27 | 4-O—CH₃ | 2-CH₃ | 6-CH₃ | —C₂H₅ | N | 2 | Is | 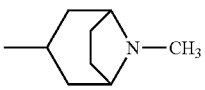 | 2F |
| 28 | 4-O—CH₃ | 2-CH₃ | 6-CH₃ | c-Pr | N | 2 | Is | 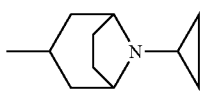 | 2F |
| 29 | 4-O—CH₃ | 2-CH₃ | 6-CH₃ | —CH₃ | N | 2 | Is | 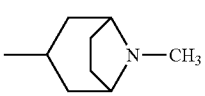 | 2F |
| 30 | 4-O—CH₃ | 2-CH₃ | 6-CH₃ | i-Pr | N | 2 | Is | 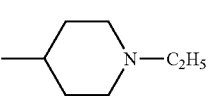 | 2F |
| 31 | 4-O—CH₃ | 2-CH₃ | 6-CH₃ | —CH₃ | N | 2 | Is | 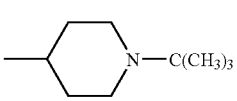 | 1F |
| 32 | 4-O—CH₃ | 2-CH₃ | 6-CH₃ | —CH₃ | N | 2 | Is | 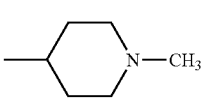 | 2F |
| 33 | 4-O—CH₃ | 2-CH₃ | 6-CH₃ | —CH₃ | N | 2 | —CH₂— | 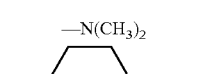 | 1F |
| 34 | 4-O—CH₃ | 2-Cl | 6-Cl | —CH₃ | N | 2 | —(CH₂)₃— | —N(CH₃)₂ | 2F |
| 35 | 4-O—CH₃ | 2-Cl | 6-Cl | —CH₃ | N | 2 | Is | 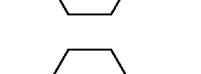 | 2F |
| 36 | 4-O—CH₃ | 2-CH₃ | 6-CH₃ | —CH₃ | N | 2 | —(CH₂)₂— | 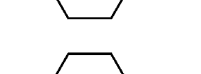 | 2F |
| 37 | 4-O—CH₃ | 2-CH₃ | 6-CH₃ | —CH₃ | N | 2 | Is | 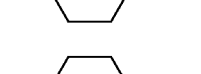 | 1F |
| 38 | 4-O—CH₃ | 2-CH₃ | 6-CH₃ | i-Pr | N | 2 | Is | 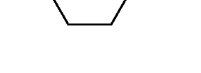 | 2F |

TABLE I-continued

| EX | R₁ | R₂ | R₃(R₄) | Rₐ | X | p | A | B | Salt |
|----|------|------|--------|------|---|---|--------|---|------|
| 39 | 4-O—CH₃ | 2-CH₃ | 6-CH₃ | —CH₃ | N | 2 | Is | 4-methyl-1-isopropylpiperidinyl | 1F |
| 40 | 4-O—CH₃ | 2-CH₃ | 6-CH₃ | —C₂H₅ | N | 2 | (CH₂)₃ | 1-methylpiperidinyl | 2F |
| 41 | 4-Cl | 2-Cl | 6-O—CH₃ | —CH₃ | N | 2 | Is | 4-methyl-1-methylpiperidinyl | 2F |
| 42 | 4-O—CH₃ | 2-Cl | 6-Cl | —CH₃ | N | 2 | Is | 4-methyl-1-ethylpiperidinyl | 1F |
| 43 | 4-O—CH₃ | 2-Cl | 6-Cl | —CH₃ | N | 2 | Is | quinuclidinyl | 1F |
| 44 | 4-O—CH₃ | 2-CH₃ | 6-CH₃ | —CH₃ | N | 2 | Is | 2,2,6,6-tetramethyl-1-methylpiperidinyl | 2TFA |
| 45 | 4-O—CH₃ | 2-CH₃ | 6-CH₃ | —CH₃ | N | 2 | (CH₂)₃ | 4-methylpiperazinyl | 2F |
| 46 | 4-O—CH₃ | 2-CH₃ | 6-CH₃ | —CH₃ | N | 2 | Is | 1-ethyltropanyl | 2F |
| 47 | 4-O—CH₃ | 2-CH₃ | 6-CH₃ | —CH₃ | N | 2 | (CH₂)₃ | 4-methyl-1,4-diazocanyl | 2F |
| 48 | 4-O—CH₃ | 2-CH₃ | 6-CH₃ | —CH₃ | N | 2 | Is | 1-isopropyltropanyl | 2F |
| 49 | 4-O—CH₃ | 2-CH₃ | 6-CH₃ | —CH₃ | N | 2 | —(CH₂)₂—CO— | 4-methyl-1,4-diazocanyl | 2TFA |
| 50 | 4-O—CH₃ | 2-CH₃ | 6-CH₃ | —CH₃ | N | 2 | (CH₂)₂ | 4-methyl-1,4-diazocanyl | 3F |

TABLE I-continued
| EX | R1 | R2 | R3(R4) | Ra | X | p | A | B | Salt |
|---|---|---|---|---|---|---|---|---|---|
| 51 | 4-O—CH3 | 2-CH3 | 6-CH3 | c-Pr | N | 2 | Is |  | 2F |
| 52 | 4-O—CH3 | 2-CH3 | 6-CH3 | —C2H5 | N | 2 | Is |  | 2F |
| 53 | 4-O—CH3 | 2-CH3 | 6-CH3 | —CH3 | N | 2 | (CH2)2 | —N(C2H5)2 | 1F |
| 54 | 4-F | 2-Cl | 6-Cl | —CH3 | N | 2 | Is | 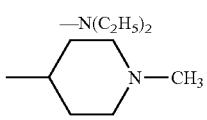 | base |
| 55 | 4-F | 2-Cl | 6-Cl | —CH3 | N | 2 | Is | 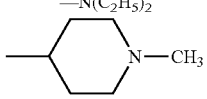 | 2F |
| 56 | 4-Br | 2-Cl | 6-Cl | —CH3 | N | 2 | Is | 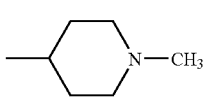 | base |
| 57 | 4-Br | 2-Cl | 6-Cl | —CH3 | N | 2 | Is | 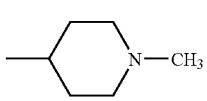 | 2F |
| 58 | 4-Cl | 2-Cl | 6-Cl | —CH3 | N | 2 | Is | 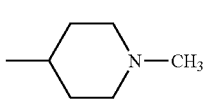 | base |
| 59 | 4-Cl | 2-Cl | 6-Cl | —CH3 | N | 2 | Is | 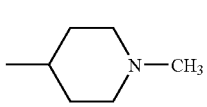 | 2F |
| 60 | 4-Cl | 2-Cl | 6-CH3 | —CH3 | N | 2 | Is | 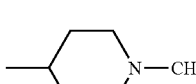 | base |
| 61 | 4-Cl | 2-Cl | 6-CH3 | —CH3 | N | 2 | Is | 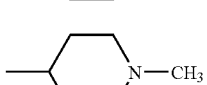 | 2F |
| 62 | 4-O—CH3 | 2-CH3 | 3,6-diCH3 | —CH3 | N | 2 | Is | 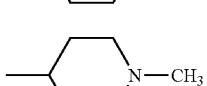 | base |
| 63 | 4-O—CH3 | 2-CH3 | 3,6-diCH3 | —CH3 | N | 2 | Is | 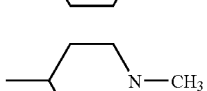 | 2F |
| 64 | 4-O—CH3 | 2-CH3 | 6-CH3 | —CH3 | N | 2 | (CH2)3 | 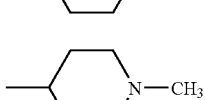 | base |

TABLE I-continued

| EX | R₁ | R₂ | R₃(R₄) | Rₐ | X | p | A | B | Salt |
|---|---|---|---|---|---|---|---|---|---|
| 65 | 4-O—CH₃ | 2-CH₃ | 6-CH₃ | —CH₃ | N | 2 | (CH₂)₃ | 4-methyl-1-methylpiperidine | base |
| 66 | 4-O—CH₃ | 2-CH₃ | 6-CH₃ | —CH₃ | N | 2 | (CH₂)₃ | 4-methyl-1-methylpiperidine | 2F |
| 67 | 4-O—CH₃ | 2-CH₃ | 6-CH₃ | —CH₃ | N | 2 | Is | 4-methylpiperidine | 2TFA |
| 68 | 4-O—CH₃ | 2-CH₃ | 6-CH₃ | —CH₃ | N | 2 | Is | 2-amino-5-methylpyridine | base |
| 69 | 4-O—CH₃ | 2-CH₃ | 6-CH₃ | —CH₃ | N | 2 | Is | 2-amino-5-methylpyridine | 1F |
| 70 | 4-O—CH₃ | 2-CH₃ | 6-CH₃ | —CH₃ | CH | 2 | —C(CH₃)₂—CH₂— | —N(CH₃)₂ | 1TFA |
| 71 | 4-O—CH₃ | 2-CH₃ | 6-CH₃ | —CH₃ | CH | 2 | —CH(OH)—CH₂— | —N(CH₃)₂ | 1TFA |
| 72 | 4-O—CH₃ | 2-CH₃ | 6-CH₃ | —CH₃ | CH | 2 | Is | 1-methylpiperazine | base |
| 73 | 4-O—CH₃ | 2-CH₃ | 6-CH₃ | —CH₃ | CH | 2 | Is | 1-methylpiperazine | 1F |
| 74 | 4-O—CH₃ | 2-CH₃ | 6-CH₃ | —CH₃ | CH | 2 | Is | 4-methyl-1-methylpiperidine | 1F |
| 75 | 4-O—CH₃ | 2-CH₃ | 6-CH₃ | CPr | CH | 2 | Is | 4-methyl-1-methylpiperidine | 2F |
| 76 | 4-O—CH₃ | 2-CH₃ | 6-CH₃ | —CH₃ | CH | 2 | (CH₂)₂ | pyrrolidine | 1F |
| 77 | 4-O—CH₃ | 2-CH₃ | 6-CH₃ | —CH₃ | CH | 2 | Is | 1-methyl-4-isopropylpiperazine | 1F |
| 78 | 4-O—CH₃ | 2-CH₃ | 6-CH₃ | —C₂H₅ | CH | 2 | (CH₂)₂ | pyrrolidine | 1F |
| 79 | 4-O—CH₃ | 2-CH₃ | 6-CH₃ | cPr | CH | 2 | (CH₂)₂ | pyrrolidine | 1F |

TABLE I-continued

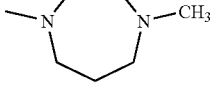

| EX | R₁ | R₂ | R₃(R₄) | Rₐ | X | p | A | B | Salt |
|---|---|---|---|---|---|---|---|---|---|
| 80 | 4-O—CH₃ | 2-CH₃ | 6-CH₃ | —CH₃ | CH | 2 | (CH₂)₂ | 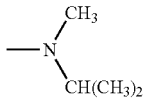 | 2F |
| 81 | 4-O—CH₃ | 2-CH₃ | 6-CH₃ | —CH₃ | CH | 2 | (CH₂)₂ | 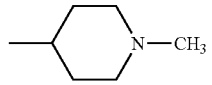 | 1F |
| 82 | 4-O—CH₃ | 2-CH₃ | 6-CH₃ | —CH₃ | CH | 2 | —N(CH₃)— | 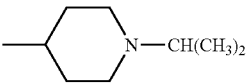 | 1F |
| 83 | 4-O—CH₃ | 2-CH₃ | 6-CH₃ | —CH₃ | CH | 2 | Is | 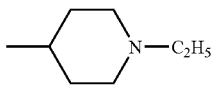 | 1F |
| 84 | 4-O—CH₃ | 2-CH₃ | 6-CH₃ | —CH₃ | CH | 2 | Is | 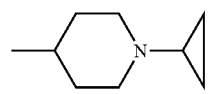 | 1F |
| 85 | 4-O—CH₃ | 2-CH₃ | 6-CH₃ | —CH₃ | CH | 2 | Is | 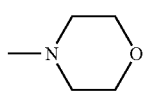 | 1F |
| 86 | 4-O—CH₃ | 2-CH₃ | 6-CH₃ | —CH₃ | CH | 2 | (CH₂)₂ | 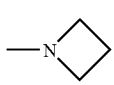 | 1F |
| 87 | 4-O—CH₃ | 2-CH₃ | 6-CH₃ | —CH₃ | CH | 2 | —C(CH₃)₂—CH₂— | 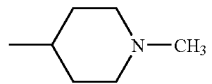 | 1F |
| 88 | 4-O—CH₃ | 2-CH₃ | 6-CH₃ | —C₂H₅ | CH | 2 | Is | 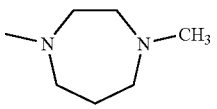 | 1F |
| 89 | 4-O—CH₃ | 2-CH₃ | 6-CH₃ | —CH₃ | CH | 2 | Is | 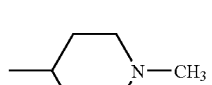 | 1F |
| 90 | 4-O—CH₃ | 2-CH₃ | 6-CH₃ | cPr | CH | 2 | Is | 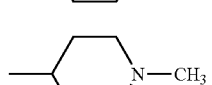 | 1F |
| 91 | 4-O—CH₃ | 2-CH₃ | 6-CH₃ | —CH₃ | CH | 2 | Is | 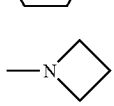 | 1F |
| 92 | 4-O—CH₃ | 2-CH₃ | 6-CH₃ | —CH₃ | CH | 2 | —(CH₂)₂— |  | 1F |
| 93 | 4-O—CH₃ | 2-Cl | 6-Cl | —CH₃ | CH | 2 | (CH₂)₂ | —N(CH₃)₂ | 1F |

TABLE I-continued

| EX | R₁ | R₂ | R₃(R₄) | Rₐ | X | p | A | B | Salt |
|---|---|---|---|---|---|---|---|---|---|
| 94 | 4-O—CH₃ | 2-Cl | 6-Cl | —CH₃ | CH | 2 | Is | 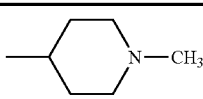 | 1F |
| 95 | 4-O—CH₃ | 2-CH₃ | 6-CH₃ | —CH₃ | CH | 2 | —CH₂— | 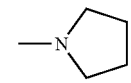 | 1F |
| 96 | 4-O—CH₃ | 2-CH₃ | 6-CH₃ | —CH₃ | CH | 2 | —CH₂— | 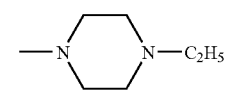 | 1F |
| 97 | 4-O—CH₃ | 2-CH₃ | 6-CH₃ | cPr | CH | 2 | —CH₂— | 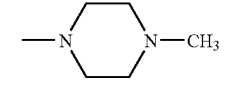 | 2F |
| 98 | 4-O—CH₃ | 2-CH₃ | 6-CH₃ | —C₂H₅ | CH | 2 | —CH₂— | 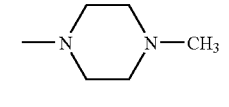 | 2F |
| 99 | 4-O—CH₃ | 2-CH₃ | 6-CH₃ | —CH₃ | CH | 2 | —CH₂— | 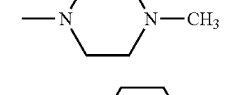 | 2F |
| 100 | 4-O—CH₃ | 2-CH₃ | 6-CH₃ | —CH₃ | CH | 2 | —C(CH₃)₂'CH₂— | 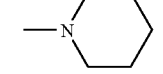 | 1TFA |
| 101 | 4-O—CH₃ | 2-CH₃ | 6-CH₃ | —CH₃ | CH | 2 | —C(CH₃)₂'CH₂— | 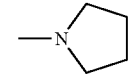 | 1F |
| 102 | 4-O—CH₃ | 2-CH₃ | 6-CH₃ | —CH₃ | CH | 2 | (CH₂)₂ | 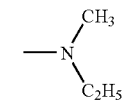 | 1F |
| 103 | 4-O—CH₃ | 2-CH₃ | 6-CH₃ | —CH₃ | CH | 2 | (CH₂)₂ | —N(C₂H₅)₂ | 1F |
| 104 | 4-O—CH₃ | 2-CH₃ | 6-CH₃ | iPr | CH | 2 | (CH₂)₂ | 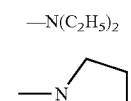 | 1F |
| 105 | 4-O—CH₃ | 2-CH₃ | 6-CH₃ | —CH₃ | CH | 2 | —C(CH₃)₂—CH₂— | 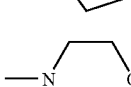 | 1F |
| 106 | 4-O—CH₃ | 2-CH₃ | 6-CH₃ | —CH₃ | CH | 2 | (CH₂)₂ | 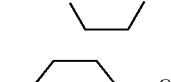 | 2F |
| 107 | 4-O—CH₃ | 2-CH₃ | 6-CH₃ | —CH₃ | CH | 2 | —CH₂— | 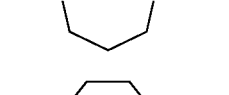 | 2F |

TABLE I-continued

| EX | R1 | R2 | R3(R4) | Ra | X | p | A | B | Salt |
|---|---|---|---|---|---|---|---|---|---|
| 108 | 4-O—CH3 | 2-CH3 | 6-CH3 | —CH3 | CH | 2 | (CH2)2 | 4-methyl-1-methylpiperidine | 1F |
| 109 | 4-O—CH3 | 2-CH3 | 6-CH3 | —CH3 | CH | 2 | (CH2)2 | 1-methylpiperidine | 1F |
| 110 | 4-O—CH3 | 2-CF3 | H | —CH3 | CH | 2 | (CH2)2 | 1-methylpyrrolidine | 1TFA |
| 111 | 4-O—CH3 | 2-CH3 | 6-CH3 | —CH3 | CH | 2 | —CH2—CO— | 1,4-dimethylpiperazine | 1F |
| 112 | 4-O—CH3 | 2-CH3 | 6-CH3 | —CH3 | CH | 2 | —C(CH3)2—CH2— | —N(C2H5)2 | 1TFA |
| 113 | 4-O—CH3 | 2-CH3 | 6-CH3 | —CH3 | CH | 2 | —CH2— | —N(CH3)2 | 1F |
| 114 | 4-O—CH3 | 2-CH3 | 6-CH3 | —CH3 | CH | 2 | —CH2— | N-methylazetidine | 1F |
| 115 | 4-CH3 | 2-CH3 | 6-CH3 | —CH3 | CH | 2 | Is | 4-methyl-1-methylpiperidine | 1TFA |
| 116 | H | 2-CF3 | H | —CH3 | CH | 2 | Is | 4-methyl-1-methylpiperidine | 1TFA |
| 117 | 4-O—CH3 | 2-CF3 | H | —CH3 | CH | 2 | Is | 4-methyl-1-methylpiperidine | 1TFA |
| 118 | 4-CH3 | 2-CH3 | 6-CH3 | —CH3 | CH | 2 | (CH2)2 | 1-methylpyrrolidine | 1TFA |
| 119 | 4-O—CH3 | 2-Cl | 6-Cl | —CH3 | CH | 2 | Is | 1,4-dimethylpiperazine | 2F |
| 120 | 4-O—CH3 | 2-CH3 | 6-CH3 | —CH3 | CH | 2 | (CH2)2 | —N(CH3)2 | 1F |
| 121 | 4-O—CH3 | 2-CH3 | 6-CH3 | —CH3 | CH | 2 | Is | 1-cyclopropyl-4-piperazine | 1F |
| 122 | 4-O—CH3 | 2-CH3 | 6-CH3 | —CH3 | CH | 2 | Is | 1-tert-butyl-4-piperazine | 2F |
| 123 | 4-O—CH3 | 2-CH3 | 6-CH3 | —CH3 | CH | 2 | —CH2— | 1,4-dimethylpiperazine | 2F |

TABLE I-continued

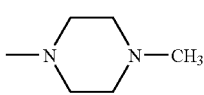

| EX | R₁ | R₂ | R₃(R₄) | Rₐ | X | p | A | B | Salt |
|---|---|---|---|---|---|---|---|---|---|
| 124 | 4-O—CH₃ | 2-CH₃ | 6-CH₃ | —CH₃ | CH | 2 | (CH₂)₂ | 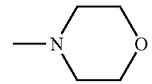 | 2F |
| 125 | 4-O—CH₃ | 2-CH₃ | 6-CH₃ | —CH₃ | CH | 2 | (CH₂)₃ | 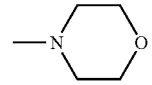 | base |
| 126 | 4-O—CH₃ | 2-CH₃ | 6-CH₃ | —CH₃ | CH | 2 | (CH₂)₃ | 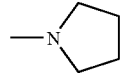 | 1F |
| 127 | 4-O—CH₃ | 2-CH₃ | 6-CH₃ | —CH₃ | CH | 2 | (CH₂)₃ | 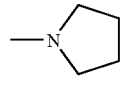 | base |
| 128 | 4-O—CH₃ | 2-CH₃ | 6-CH₃ | —CH₃ | CH | 2 | (CH₂)₃ | 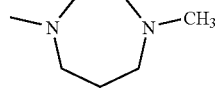 | 1F |
| 129 | 4-O—CH₃ | 2-CH₃ | 6-CH₃ | —CH₃ | CH | 2 | (CH₂)₃ | 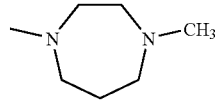 | base |
| 130 | 4-O—CH₃ | 2-CH₃ | 6-CH₃ | —CH₃ | CH | 2 | (CH₂)₃ | 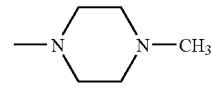 | 2F |
| 131 | 4-O—CH₃ | 2-CH₃ | 6-CH₃ | —CH₃ | CH | 2 | (CH₂)₃ | 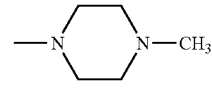 | base |
| 132 | 4-O—CH₃ | 2-CH₃ | 6-CH₃ | —CH₃ | CH | 2 | (CH₂)₃ | 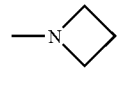 | 2F |
| 133 | 4-O—CH₃ | 2-CH₃ | 6-CH₃ | —CH₃ | CH | 2 | (CH₂)₃ | 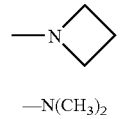 | base |
| 134 | 4-O—CH₃ | 2-CH₃ | 6-CH₃ | —CH₃ | CH | 2 | (CH₂)₃ |  | 1F |
| 135 | 4-O—CH₃ | 2-CH₃ | 6-CH₃ | —CH₃ | CH | 2 | (CH₂)₃ | —N(CH₃)₂ | base |
| 136 | 4-O—CH₃ | 2-CH₃ | 6-CH₃ | —CH₃ | CH | 2 | (CH₂)₃ | N(CH₃)₂ | 1F |
| 137 | 4-O—CH₃ | 2-CH₃ | 6-CH₃ | —CH₃ | CH | 2 | Is |  | 1FTA |
| 138 | 4-O—CH₃ | 2-CH₃ | 6-CH₃ | —CH₃ | CH | 2 | (CH₂)₂ | —NH(CH₃) | Base |
| 139 | 4-O—CH₃ | 2-CH₃ | 6-CH₃ | —CH₃ | CH | 2 | (CH₂)₂ | —NH(CH₃) | 1F |
| 140 | 4-O—CH₃ | 2-CH₃ | 6-CH₃ | —CH₃ | CH | 2 | Is | —NH₂ | base |

TABLE I-continued

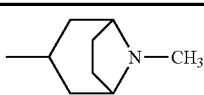

| EX | R$_1$ | R$_2$ | R$_3$(R$_4$) | R$_a$ | X | p | A | B | Salt |
|---|---|---|---|---|---|---|---|---|---|
| 141 | 4-O—CH$_3$ | 2-CH$_3$ | 6-CH$_3$ | —CH$_3$ | CH | 2 | —NH— | 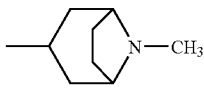 | base |
| 142 | 4-O—CH$_3$ | 2-CH$_3$ | 6-CH$_3$ | —CH$_3$ | CH | 2 | —NH— | 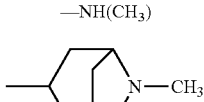 | 2TFA |
| 143 | 4-O—CH$_3$ | 2-CH$_3$ | 6-CH$_3$ | —CH$_3$ | CH | 2 | ls | —NH(CH$_3$) | base |
| 144 | 4-O—CH$_3$ | 2-CH$_3$ | 6-CH$_3$ | —CH$_3$ | CH | 2 | —N(CH$_3$)— | 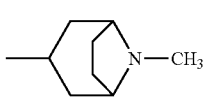 | base |
| 145 | 4-O—CH$_3$ | 2-CH$_3$ | 6-CH$_3$ | —CH$_3$ | CH | 2 | —N(CH$_3$)— | 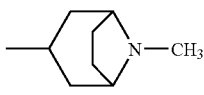 | 2TFA |
| 146 | 4-O—CH$_3$ | 2-CH$_3$ | 6-CH$_3$ | —CH$_3$ | CH | 2 | —CH$_2$— | 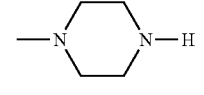 | base |
| 147 | 4-O—CH$_3$ | 2-CH$_3$ | 6-CH$_3$ | —CH$_3$ | CH | 2 | —CH$_2$— | 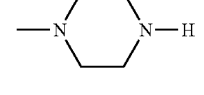 | 1F |
| 148 | 4-O—CH$_3$ | 2-CH$_3$ | 6-CH$_3$ | —CH$_3$ | CH | 2 | —CO—CH$_2$— | 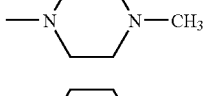 | 2TFA |
| 149 | 4-O—CH$_3$ | 2-CH$_3$ | 6-CH$_3$ | —CH$_3$ | N | 2 | ls | 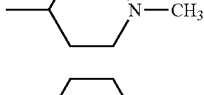 | base |
| 150 | 4-O—CH$_3$ | 2-CH$_3$ | 6-CH$_3$ | —CH$_3$ | N | 2 | ls | 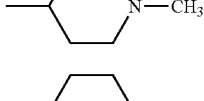 | 2HCl |
| 151 | 4-O—CH$_3$ | 2-CH$_3$ | 6-CH$_3$ | —CH$_3$ | N | 2 | ls | 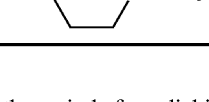 | 2F |

In the above table, ls means a single bond, TFA means that the compound is in the form of a salt with trifluoroacetic acid, F means that the compound is in the form of a salt with fumaric acid. HCl means that the compound is in the form of a salt with hydrochloric acid.

Biological Activity

The compounds of the present invention were evaluated for their analgesic property using the formalin-induced pain response test in mice (Shibata, M., Ohkubo, T., Takahashi, H. & R. Inoki. Modified formalin test: characteristic biphasic pain response. *Pain*, 38, 347-352). To summarize, formalin (0.92% in physiological saline) is injected into the hind paw and the period of paw licking, which represents pain intensity, is recorded from 0 to 5 min (1$^{st}$ phase) and from 15 to 30 min (2$^{nd}$ phase) after the injection. According to this test, the percentage inhibition of the second paw licking phase induced by formalin is 43% for the compound of example 4 administered via the oral route at a dose of 3 mg/kg and 40% for the compound of example 6 administered via the oral route at a dose of 1 mg/kg.

These results demonstrate a substantial lowering of pain response after administering the compounds.

Subsequent to the results of the preceding test, the compounds of the invention were subjected to a test intended to demonstrate their mode of action and involving the $B_1$ receptor of bradykinin.

This test uses the human umbilical vein and is conducted as per the following protocol:

Human umbilical cords 15-25 cm long are recovered just after delivery and are immediately placed in a flask containing a Krebs solution of composition (in mM): 119 NaCl 119, 4.7 KCl, 1.18 $KH_2PO_4$, 1.17 $MgSO_4$, 25 $NaHCO_3$, 2.5 $CaCl_2$, 5.5 Glucose, 0.026 EDTA then stored at 4° C.

The cord is dissected in Krebs solution to release the umbilical vein. The vein is cleansed of all adhering tissue and cut into small rings 3-4 mm in width. The endothelium is carefully removed by inserting a fine n° 1 catheter, made slightly abrasive, into the vessel lumen.

To induce expression of the $B_1$ receptor of bradykinin, the vein segments are allowed to incubate at 37° C. in a 25 ml chamber for 16 hours in an EMEM culture medium oxygenated by a 95% $O_2$+5% $CO_2$ mixture to which antibiotics are added: penicillin 10 000 IU/ml and streptomycin 10 000 IU/ml. The following day, the vein rings are mounted on a stainless steel support connected to an isometric sensor and placed in a 8 ml isolated organ bath chamber thermostated at 37° C., containing the Krebs solution oxygenated by a 95% $O_2$+5% $CO_2$ mixture.

After a rest period of one hour during which the rings are rinsed 5 to 6 times with the Krebs solution (maintained at 37° C. throughout the entire handling procedure and oxygenated by a 95% $O_2$+5% $CO_2$ mixture), the vein is gradually subjected to a 1 g load. When the load is stable, after approximately 45 minutes, the Krebs solution is replaced by a hyperpotassium solution (KPSS: at a temperature of 37° C.) of the same composition but containing 125 mM KCl and not NaCl.

After a series of rinsings, rests and load readjustments, the maximum contraction of each segment is determined by further depolarisation with the KPSS solution.

After a new rest period during which the 1 g load is constantly readjusted, the following compounds are added to the isolated organ bath: Mepyramine (1 µM), Atropine (1 µM), Indometacine (3 µM), LNA (30 µM), Captopril (10 µM), DL-Thiorphan (1 µM) and Nifedipine (0.1 µM).

After 20 minutes, the molecule to be tested or the molecule solvent is added to the isolated organ bath. The molecules are examined at 10 µM; should a molecule show a sufficient level of activity, it is examined at lower concentrations (eg: 1-0.1-0.01 µM).

After 15 minutes incubation, the vein segments are contracted through the addition of increasing concentrations of des-Arg10-Kallidin (0.1 nM to 30 000 nM) in the chamber.

The $EC_{50}$ values (effective concentrations of agonists required to produce 50% of the maximum response obtained with KPSS) are calculated using the least square method.

The $pK_B = [-\log K_B]$ is obtained from the equation:

$$K_B = [A]/(\text{concentration ratio} - 1)$$

in which [A] is the concentration of antagonist and the (concentration ratio) represents the ratio between $EC_{50}$ in the presence of an antagonist and $EC_{50}$ in the absence of antagonist.

According to this test, the compounds of the invention cited in the description show a $pK_B$ value of more than 7.

By way of example, the $pK_B$ values of some compounds of the invention are given in table II:

|  | Ex. | | | | | | | | | | | | | |
| --- | --- | --- | --- | --- | --- | --- | --- | --- | --- | --- | --- | --- | --- | --- |
|  | 13 | 19 | 21 | 32 | 33 | 45 | 46 | 74 | 76 | 77 | 79 | 84 | 89 | 99 | 120 |
| $pK_B$ | 8.4 | 7.5 | 7.8 | 9.2 | 8.6 | 7.9 | 8.6 | 9 | 8 | 8.5 | 8.1 | 9.2 | 8.1 | 8 | 7.6 |

The compounds of the present invention may be used to treat various forms of pain such as inflammatory hyperalgesia, allodynia, neuropathic pain assoicated with, for example, diabetes, with neuropathies (constriction of sciatica nerve, lumbago), with any form of trauma, surgery (tooth extraction, tonsil removal), interstitial cystitis, inflammatory colon disease, or with cancer.

The compounds of the present invention may also be used to treat any pathology associated with neutrophil migration such as acute respiratory distress syndrome for example, or psoriasis, chronic lung obstructions, inflammatory diseases, in particular inflammatory diseases of the colon, rheumatoid polyarthritis.

The activity of the compounds of the invention, evidenced during the biological tests, is indicative of analgesic properties and permits their considered use for therapy.

According to the invention, the use is advocated of compounds defined by formula I and of their salts with non-toxic acids, preferably their pharmaceutically acceptable salts, as active ingredients in medicinal products intended for the treatment of mammals, notably in man, suffering from pain or certain diseases generally characterized by massive neutrophil migration.

Among the diseases which can be treated by administering a therapeutically efficient quantity of at least one of the formula I compounds, mention may be made of inflammatory hyperalgesia, neuropathic pain, pain assoicated with trauma or with cancer, inflammatory diseases of the colon, rheumatoid polyarthritis, psoriasis, chronic lung obstructions or acute respiratory distress syndrome.

The invention also concerns a method for treating pain or the above-mentioned diseases which consists of administering a therapeutically efficient quantity of a formula I compound to patients in need thereof.

The dose of active ingredient is dependent upon the mode of administration and type of pathology; it is generally between 0.05 and 10 mg/kg of the treated patient. In relation to the intended treatment, the formula I compounds or their salts may be associated with other active ingredients and are to be formulated with routinely used excipients.

To obtain swift action, notably for the treatment of acute pain, the method of administration of the medicinal product is preferably by injection, for example via the intramuscular or the subcutaneous route. For chronic pain, the medicinal product may be administered in common galenic formulations, for example via the oral route in capsule or tablet form, in which a compound of the invention is associated with excipients known to persons skilled in the art, or in adhesive patch form in which a compound of the invention is formulated with excipients known to persons skilled in the art to promote transdermal passing of the active ingredient.

The invention claimed is:

1. A compound, selected from the group consisting of:
   a) a compound of formula:

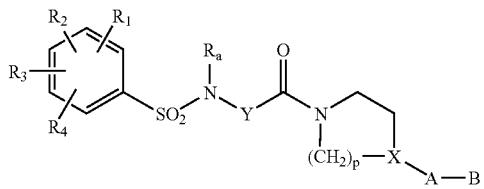

in which,
R$_1$ represent a hydrogen, a halogen, a C$_1$-C$_3$ alkyl group, or a C$_1$-C$_3$ alkoxy group,
R$_2$ represents a hydrogen, a halogen, a C$_1$-C$_3$ alkyl group, a C$_1$-C$_3$ alkoxy group, or a CF$_3$ groups,
R$_3$ represents a hydrogen, a halogen, a C$_1$-C$_3$ alkyl group or a C$_1$-C$_3$ alkoxy group,
R$_4$ represents a hydrogen or a C$_1$-C$_3$ alkyl group,
R$_a$ represents a C$_1$-C$_4$ alkyl group,
Y represents a —CH$_2$—CH$_2$—O—CH$_2$— group,
X represents CH or a nitrogen atom,
p represents 2 or 3,
A represents a single bond, a nitrogen atom optionally substituted with a methyl group, or a straight or branched C$_1$-C$_5$ alkylene group optionally hydroxylated or of which one of the carbon atoms is oxidized into a ketone function, provided that A and X together do not represent a nitrogen atom,
   B represents a nitrogen-containing heterocycle or an amine group optionally substituted with one or two C$_1$-C$_4$ alkyl groups, or
   b) addition salts of the above formula I compound with an acid.

2. A compound according to claim 1, wherein R$_2$ and R$_3$ represent a methyl group at position 2,6 on the aromatic ring.

3. A method for preparing a formula I compound as defined in claim 1, and its addition salts, comprising:
   a) allowing an acid of formula:

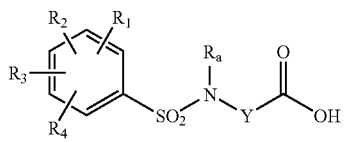

in which
R$_1$ represents a hydrogen, a halogen, a C$_1$-C$_3$ alkyl group, C$_1$-C$_3$ alkoxy group,
R$_2$ represents a hydrogen, a halogen, C$_1$-C$_3$ alkyl groups, C$_1$-C$_3$ alkoxy group, or a CF$_3$ group,
R$_3$ represents a hydrogen, a halogen, a C$_1$-C$_3$ alkyl group, C$_1$-C$_3$ alkoxy group,
R$_4$ represents a hydrogen or a C$_1$-C$_3$ alkyl group,
R$_a$ represents a C$_1$-C$_4$ alkyl group,
Y represents a —CH$_2$—CH$_2$—O—CH$_2$— group,
to react with a nitrogen-containing heterocycle of formula:

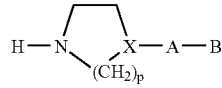

in which
X represents CH or a nitrogen atom,
p represents 2 or 3,
A represents a single bond, a nitrogen atom optionally substituted with a methyl group (if X does not represent a nitrogen atom), or a straight or branched C$_1$-C$_5$ alkylene group, optionally hydroxylated or of which one of the carbon atoms is oxidized into a ketone function,
B represents a nitrogen-containing heterocycle or an amine group optionally substituted with one or two C$_1$-C$_4$ alkyl groups, on the understanding that, should a non-substituted nitrogen atom be present, this nitrogen atom is protected by an amino-protecting group,
in a solvent, in the presence of activators, at a temperature lying between ambient temperature and the boiling point of the solvent, for about 2 to 15 hours, to obtain the amide of formula:

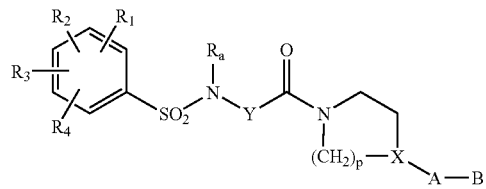

in which R$_1$, R$_2$, R$_3$, R$_4$, R$_a$, Y, p, X, A and B maintain the same meaning as in the starting products,
b) optionally, removing the amino-protecting groups, and
c) optionally, obtaining an addition salt of the formula I compound with a mineral or organic acid.

4. A method for preparing a compound of formula:

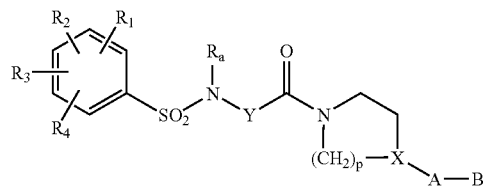

in which
R$_1$ represents a hydrogen, a halogen, a C$_1$-C$_3$ alkyl group or a C$_1$-C$_3$ alkoxy group,
R$_2$ represents a hydrogen, a halogen, a C$_1$-C$_3$ alkyl group or a C$_1$-C$_3$ alkoxy group, or a CF$_3$ group,
R$_3$ represents a hydrogen, a halogen, a C$_1$-C$_3$ alkyl group or a C$_1$-C$_3$ alkoxy group,
R$_4$ represents a hydrogen, a halogen, a C$_1$-C$_3$ alkyl group,
R$_a$ represents a C$_1$-C$_4$ alkyl group,
Y represents a —CH$_2$—CH$_2$—O—CH$_2$— group,
X represents CH or a nitrogen atom,
p represents 2 or 3,
A represents a single bond, a nitrogen atom optionally substituted with a methyl group, or a straight or branched $C_1$-$C_5$ alkylene group optionally hydroxylated or of which one of the carbon atoms is oxidized into a ketone function, provided that A and X together do not represent a nitrogen atom, B represents a nitrogen-containing heterocycle or an amine group optionally substituted with one or two $C_1$-$C_4$ alkyl groups, and its addition salts, the method comprising:
a) allowing an acid of formula:

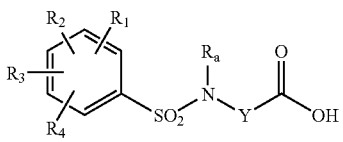
II in which;
$R_1$ represents a hydrogen, a halogen, a $C_1$-$C_3$ alkyl group or a $C_1$-$C_3$ alkoxy group, $R_2$ represents a hydrogen, a halogen, a $C_1$-$C_3$ alkyl group or a $C_1$-$C_3$ alkoxy group, or a $CF_3$ group, $R_3$ represents a hydrogen, a halogen, a $C_1$-$C_3$ alkyl group or a $C_1$-$C_3$ alkoxy group, $R_4$ represents a hydrogen or a $C_1$-$C_3$ alkyl group, $R_a$ represents a $C_1$-$C_4$ alkyl group, Y represents a —$CH_2$—$CH_2$—O—$CH_2$— group, to react with a chlorination agent, to obtain the acid chloride of formula:

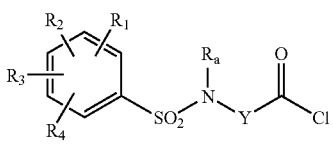
IIa in which $R_1$, $R_2$, $R_3$, $R_4$, $R_a$ and Y have the same meaning as in the starting compound, and b) allowing the acid chloride of formula IIa to react with an amine of formula III as defined in claim 3, to obtain the compound of formula I, and c) optionally, obtaining an addition salt of the formula I compound with a mineral or organic acid.

5. A method for preparing a formula I compound such as defined in claim 1, and its addition salts, comprising:

a) allowing an acid compound of formula:

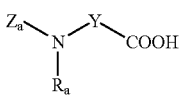
VII in which Ra represents a $C_1$-$C_4$ alkyl group,
Y represents a —$CH_2$—$CH_2$—O—$CH_2$— group, and $Z_a$ represents an amino-protcting group,
to react with a nitrogen-containing heterocycle of formula:

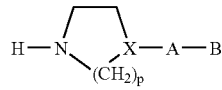
III in which
X represents CH or a nitrogen atom,
p represents 2 or 3,
A represents a single bond, a nitrogen atom optionally substituted with a methyl group (if X does not also represent a nitrogen atom) or a straight or branched $C_1$-$C_5$ alkylene group, optionally hydroxylated or of which one of the carbon atoms is oxidized into a ketone function, B represents a nitrogen-containing heterocycle or an amine group optionally substituted with one or two $C_1$-$C_4$ alkyl groups, on the understanding that, should a non-substituted nitrogen atom be present on said nitrogen-containing heterocycle, this nitrogen atom is protected by a different amino-protecting group to the amino-protecting group used for acid compound VII, in a solvent, in the presence of activators, at a temperature generally lylng between ambient temperature and the boiling point of the solvent, for about 2 to 15 hours, to obtain the amide of formula:

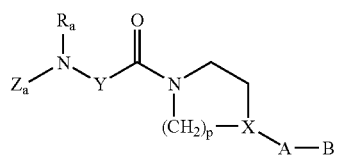
VIII in which $Z_a$, $R_a$, Y, p, X, A and B maintain the same meaning as in the starting compounds, b) removing the $Z_a$ amino-protecting group to obtain the secondary amine of formula:

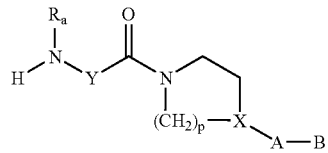
IX in which $R_a$, Y, p, X, A and B maintain the same meaning as in the preceding compound, c) allowing this secondary amine IX to react with a benzenesulphonyl chloride of formula:

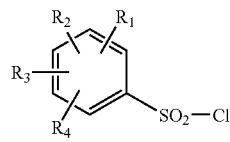
IV in which

R₁ represents one atom or group of atoms selected from a hydrogen atom, the halogens, $C_1$-$C_3$ alkyl groups, $C_1$-$C_3$ alkoxy groups, R₂ represents one atom or group of atoms selected from a hydrogen atom, the halogens, $C_1$-$C_3$ alkyl groups, $C_1$-$C_3$ alkoxy groups, or $CF_3$, R₃ represents one atom or group of atoms selected from a hydrogen atom, the halogens, $C_1$-$C_3$ alkyl groups, $C_1$-$C_3$ alkoxy groups, R₄ represents one atom or group of atoms selected from a hydrogen atom or $C_1$-$C_3$ alkyl groups, in a solvent, in the presence of an aprotic organic base, at a temperature between about 0 and 50° C., for about 1 to 3 hours, to obtain the sulphonamide of formula:

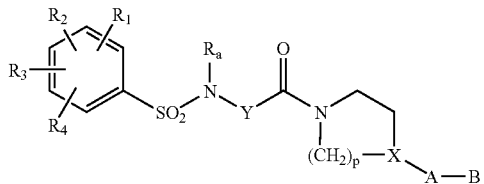

I in which R₁, R₂, R₃, R₄, R_a, Y, p, X, A and B maintain the same meaning as in the starting compounds, d) optionally, removing the amino-protecting groups, and
e) optionally necessary, obtaining an addition salt of the formula I compound with a mineral or organic acid.

6. A therapeutic composition, wherein, in association with at least one physiologically acceptable excipient, it contains at least one formula I compound according to claim 1, or one of its pharmaceutically acceptable addition salts with an acid.

7. The compound of claim 1, which is selected from the group consisting of:

1-[[2-[[(4-methoxy-2,6-dimethylphenyl)sulphonyl]methylamino]-ethoxy]acetyl]-4-[2-(1-pyrrolidinyl)ethyl]piperazine, bis-trifluoroacetate;

N-[2-[2-[4-[(3RS)-1-azabicyclo[2.2.2]oct-3-yl]-1-piperazinyl]-2-oxo-ethoxy]ethyl]-N,2,4,6-tetramethylbenzenesulphonamide, bis trifluoro-acetate;

N-[2-[2-[4-[(3RS)-1-azabicyclo[2.2.2]oct-3-yl]-1-piperazinyl]-2-oxo-ethoxy]ethyl]-4-methoxy-N,2,6-trimethylbenzenesulphonamide;

N-[2-[2-[4-[(3RS)-1-azabicyclo[2.2.2]oct-3-yl]-1-piperazinyl]-2-oxo-ethoxy]ethyl]-4-methoxy-N,2,6-trimethylbenzenesulphonamide, difumarate;

N-[2-[2-[4-[(3S)-1-azabicyclo[2.2.2]oct-3-yl]-1-piperazinyl]-2-oxo-ethoxy]ethyl]-4-methoxy-N,2,6-trimethylbenzenesulphonamide;

N-[2-[2-[4-v(3S)-1-azabicyclo[2.2.2]oct-3-yl]-1-piperazinyl]-2-oxo-ethoxy]ethyl]-4-methoxy-N,2,6-trimethylbenzenesulphonamide, fumarate;

N-[2-[2-[4-[(3R)-1-azabicyclo[2.2.2]oct-3-yl]-1-piperazinyl]-2-oxo-ethoxy]ethyl]-4-methoxy-N,2,4,6-tetramethylbenzenesulphonamide, fumarate;

1-[[2-[[(4-methoxy-2,6-dimethylphenyl)suphonyl]methylamino]-ethoxy]-acetyl]-4-[3-(1-pyrrolidinyl)propyl]piperazine, bis-trifluoroacetate;

1-[[2-[[(4-methoxy-2,6-dimethylphenyl)suphonyl]methylamino]-ethoxy]-acetyl]-4-[2-(4-morpholinyl)ethyl]piperazine, bis-trifluoroacetate;

1-[[2-[[(4-methoxy-2,6-dimethylphenyl)sulphonyl]methylamino]-ethoxy]-acetyl]-4-[2-(4-morpholinyl)ethyl]piperazine, bis-trifluoroacetate;

1-[[2-[[(4-methoxy-2,6-dimethylphenyl)sulphonyl]methylamino]ethoxy]acetyl]-4-[3-(1-piperidinyl)propyl]piperazine, bis-trifluoroacetate;

1-[[2-[[(4-methoxy-2,6-dimethylphenyl)sulphonyl]methylamino]-ethoxy]-acetyl]-4-[3-(dimethylamino)propyl]piperazine, bis-trifluoroacetate;

4-methoxy-N,2,6-trimethyl-N-[2-[2-[4-(1-methyl-4-piperidinyl)-1-piperazinyl]-2-oxoethoxy]ethyl]benzenesulphonamide, bis trifluoroacetate;

4-methoxy-N,2,6-trimethyl-N-[2-[2-[4-(8-methyl-8-azabicyclo[3.2.1]-oct-3-yl)-1-piperazinyl]-2-oxoethoxy]ethyl]-benzenesulphonamide, fumarate;

1-(1-azabicyclo[2.2.2]oct-3-yl)hexahydro-4-[[2-[[(4-methoxy-2,6-dimethylphenyl)sulphonyl]methylamino]ethoxy]acetyl]-1H-1,4-diazepine, fumarate;

N-[2-[2-[4-[3-(1-azetidinyl)propyl]-1-piperazinyl]-2-oxo-ethoxy]ethyl]-4-methoxy-N,2,6-trimethylbenzenesulphonamide, difumarate;

N-[2-[2-[4-(1-methyl-3-piperidinyl)-1-piperazinyl]-2-oxo-ethoxy]ethyl]-4-methoxy-N,2,6-trimethylbenzenesulphonamide, difumarate;

N-[2-[2-[4-(1-methyl-4-piperidinyl)-1-piperazinyl]-2-oxo-ethoxy]ethyl]-4-methoxy-N-cyclopropyl-2,6-dimethylbenzenesulphonamide, difumarate;

N-[2-[2-[4-[2-(1-pyrrolidinyl)ethyl]-1-piperazinyl]-2-oxo-ethoxy]ethyl]-4-methoxy-N-cyclopropyl-2,6-dimethylbenzenesulphonamide, difumarate;

N-[2-[2-[4-[(1-methyl-2-imidazolyl)methyl]-1-piperazinyl]-2-oxo-ethoxy]ethyl]-4-methoxy-N,2,6-trimethylbenzenesulphonamide, difumarate;

N-[2-[2-[4-(1-methyl-4-piperidinyl)-1-piperazinyl]-2-oxo-ethoxy]ethyl]-4-methoxy-N-ethyl-2,6-dimethylbenzenesulphonamide, difumarate;

N-[2-[2-[4-[3-(dimethylamino)propyl]-1-piperazinyl]-2-oxo-ethoxy]ethyl]-4-methoxy-N-ethyl-2,6-dimethylbenzenesulphonamide, difumarate;

N-[2-[2-[4-(9-methyl-9-azabicyclo[3.3.1]non-3-yl)-1-piperazinyl]-2-oxo-ethoxy]ethyl]-4-methoxy-N,2,6-trimethylbenzenesulphonamide, fumarate;

N-[2-[2-[4-[3-(1-pyrrolidinyl)propyl]-b 1-piperazinyl]-2-oxo-ethoxy]ethyl]-4-methoxy-N-ethyl-2,6-dimethylbenzenesulphonamide, difumarate;

N-[2-[2-[4-[3-(1-pyrrolidinyl)propyl]-1-piperazinyl]-2-oxo-ethoxy]ethyl]-4-methoxy-N-cyclopropyl-2,6-dimethylbenzenesulphonamide, difumarate;

N-[2-[2-[4-(8-cyclopropyl-8-azabicyclo[3.2.1]oct-3-yl)-1-piperazinyl]-2-oxo-ethoxy]ethyl]-4-methoxy-N,2,6-trimethylbenzenesulphonamide, fumarate;

N-[2-[2-[4-(8-methyl-8-azabicyclo[3.2.1]oct-3-yl)-1-piperazinyl]-2-oxo-ethoxy]ethyl]-4-methoxy-N-ethyl-2,6-dimethylbenzenesulphonamide, difumarate;

N-[2-[2-[4-(8-methyl-8-azabicyclo[3.2.1]oct-3-yl)-1-piperazinyl]-2-oxo-ethoxy]ethyl]-4-methoxy-N-cyclopropyl-2,6-dimethylbenzenesulphonamide, difumarate;

N-[2-[2-[4-(1-cyclopropyl-4-piperidinyl)-1-piperazinyl]-2-oxo-ethoxy]ethyl]-4-methoxy-N,2,6-trimethylbenzenesulphonamide, difumarate;

N-[2-[2-[4-(8-methyl-8-azabicyclo[3.2.1]oct-3-yl)-1-piperazinyl]-2-oxo-ethoxy]ethyl]-4-methoxy-N-(1-methylethyl)-2,6-dimethylbenzenesulphonamide, difumarate.

N-[2-[2-[4-(1-ethyl-4-piperidinyl)-1-piperazinyl]-2-oxo-ethoxy]ethyl]-4-methoxy-N,2,6-trimethylbenzenesulphonamide, fumarate;

N-[2-[2-[4-[1-(1,1-dimethylethyl)-4-piperidinyl]-1-piperazinyl]-2-oxo-ethoxy]ethyl]-4-methoxy-N,2,6-trimethylbenzenesulphonamide, difumarate;

N-[2-[2-[4-[(1-methyl-4-piperidinyl)methyl]-1-piperazinyl]-2-oxo-ethoxy]ethyl]-4-methoxy-N,2,6-trimethylbenzenesulphonamide, fumarate;

N-[2-[2-[4-[3-(dimethylamino)propyl]-1-piperazinyl]-2-oxo-ethoxy]ethyl]-2,6-dichloro-4-methoxy-N-methylbenzenesulphonamide, difumarate;

N-[2-[2-[4-(1-methyl-4-piperidinyl)-1-piperazinyl]-2-oxo-ethoxy]ethyl]-2,6-dichloro-4-methoxy-N-methylbenzenesulphonamide, difumarate;

N-[2-[2-[4-[2-(1-methyl-4-piperidinyl)ethyl]-1-piperazinyl]-2-oxo-ethoxy]ethyl]-4-methoxy-N,2,6-trimethylbenzenesulphonamide, difumarate;

N-[2-[2-[4-(1-methyl-4-piperidinyl)hexahydro-1H-1,4-diazepin-1-yl]-2-oxo-ethoxy]ethyl]-4-methoxy-N,2,6-trimethylbenzenesulphonamide, fumarate;

N-[2-[2-[4-(1-methyl-4-piperidinyl)-1-piperazinyl]-2-oxo-ethoxy]ethyl]-4-methoxy-N-(1-methylethyl)-2,6-dimethylbenzenesulphonamide, difumarate;

N-[2-[2-[4-[1-(1-methylethyl)-4-piperidinyl]-1-piperazinyl]-2-oxo-ethoxy]ethyl]-4-methoxy-N,2,6-trimethylbenzenesulphonamide, fumarate;

N-[2-[2-[4-[3-(1-piperidinyl)propyl]-1-piperazinyl]-2-oxo-ethoxy]ethyl]-4-methoxy-N-ethyl-2,6-dimethylbenzenesulphonamide, difumarate;

N-[2-[2-[4-(1-methyl-4-piperidinyl)-1-piperazinyl]-2-oxo-ethoxy]ethyl]-2,4-dichloro-6-methoxy-N-methylbenzenesulphonamide, difumarate;

N-[2-[2-[4-(1-ethyl-4-piperidinyl)-1-piperazinyl]-2-oxo-ethoxy]ethyl]-2,6-dichloro-4-methoxy-N-methyl-benzenesulphonamide, fumarate;

N-[2-[2-[4-((3S)-1-azabicyclo[2.2.2]oct-3-yl)-1-piperazinyl]-2-oxo-ethoxy]ethyl]-4-methoxy-N-methyl-2,6-dichlorobenzenesulphonamide, fumarate;

N-[2-[2-[4-(1,2,2,6,6-pentamethyl-4-piperidinyl)-1-piperazinyl]-2-oxo-ethoxy]ethyl]-4-methoxy-N,2,6-trimethylbenzenesulphonamide, bis(trifluoroacetate);

N-[2-[2-[4-[3-(4-methyl-1-piperazinyl)propyl]-1-piperazinyl]-2-oxo-ethoxy]ethyl]-4-methoxy-N,2,6-trimethylbenzenesulphonamide, difumarate;

N-[2-[2-[4-[3-(4-methyl-hexahydro-1H-1,4-diazepin-1-yl)propyl]-1-piperazinyl]-2-oxo-ethoxy]ethyl]-4-methoxy-N,2,6-trimethylbenzenesulphonamide, difumarate;

N-[2-[2-[4-[8-(1-methylethyl)-8-azabicyclo[3.2.1]oct-3-yl]-1-piperazinyl]-2-oxo-ethoxy]ethyl]-4-methoxy-N,2,6-trimethylbenzenesulphonamide, difumarate;

N-[2-[2-[4-[3-(4-methyl-hexahydro-1H-1,4-diazepin-1-yl)-3-oxo-propyl]-1-piperazinyl]-2-oxo-ethoxy]ethyl]-4-methoxy-N,2,6-trimethylbenzenesulphonamide, bis(trifluoroacetate);

N-[2-[2-[4-[2-(4-methyl-hexahydro-1H-1,4-diazepin-1-yl)ethyl]-1-piperazinyl]-2-oxo-ethoxy]ethyl]-4-methoxy-N,2,6-trimethylbenzenesulphonamide, trifumarate;

N-[2-[2-[4-((3S)-1-azabicyclo[2.2.2]oct-3-yl)-1-piperazinyl]-2-oxo-ethoxy]ethyl]-4-methoxy-N-cyclopropyl-2,6-dimethylbenzenesulphonamide, difumarate;

N-[2-[2-[4-((3S)-1-azabicyclo[2.2.2]oct-3-yl)-1-piperazinyl]-2-oxo-ethoxy]ethyl]-4-methoxy-N-ethyl-2,6-dimethylbenzenesulphonamide, difumarate;

N-[2-[2-[4-[2-(diethylamino)ethyl]-1-piperazinyl]-2-oxo-ethoxy]ethyl]-4-methoxy-N,2,6-trimethylbenzenesulphonamide, fumarate;

N-[2-[2-[4-(1-methyl-4-piperidinyl)-1-piperazinyl]-2-oxo-ethoxy]ethyl]-2,6-dichloro-4-fluoro-N-methyl-benzenesulphonamide;

N-[2-[2-[4-(1-methyl-4-piperidinyl)-1-piperazinyl]-2-oxo-ethoxy]ethyl]-2,6-dichloro-4-fluoro-N-methyl-benzenesulphonamide, difumarate;

N-[2-[2-[4-(1-methyl-4-piperidinyl)-1-piperazinyl]-2-oxo-ethoxy]ethyl]-4-bromo-2,6-dichloro-N-methyl-benzenesulphonamide;

N-[2-[2-[4-(1-methyl-4-piperidinyl)-1-piperazinyl]-2-oxo-ethoxy]ethyl]-4-bromo-2,6-dichloro-N-methyl-benzenesulphonamide, difumarate;

N-[2-[2-[4-(1-methyl-4-piperidinyl)-1-piperazinyl]-2-oxo-ethoxy]ethyl]-2,4,6-trichloro-N-methyl-benzenesulphonamide;

N-[2-[2-[4-(1-methyl-4-piperidinyl)-1-piperazinyl]-2-oxo-ethoxy]ethyl]-2,4,6-trichloro-N-methyl-benzenesulphonamide, difumarate;

N-[2-[2-[4-(1-methyl-4-piperidinyl)-1-piperazinyl]-2-oxo-ethoxy]ethyl]-2,4-dichloro-6-methyl-N-methyl-benzenesulphonamide;

N-[2-[2-[4-(1-methyl-4-piperidinyl)-1-piperazinyl]-2-oxo-ethoxy]ethyl]-2,4-dichloro-6-methyl-N-methyl-benzenesulphonamide, difumarate;

N-[2-[2-[4-(1-methyl-4-piperidinyl)-1-piperazinyl]-2-oxo-ethoxy]ethyl]-4-methoxy-2,3,6-trimethyl-N-methyl-benzenesulphonamide;

4-methoxy-N,2,6-trimethyl-N-[2-[2-oxo-2-[4-[3-(4-piperidinyl)-propyl]-1-piperazinyl]ethoxy]ethyl]benzenesulphonamide;

4-methoxy-N,2,6-trimethyl-N-[2-[2-oxo-2-[4-[3-(1-methyl-4-piperidinyl)propyl]-1-piperazinyl]ethoxy]ethyl]benzenesulphonamide;

4-methoxy-N,2,6-trimethyl-N-[2-[2-oxo-2-[4-[3-(1-methyl-4-piperidinyl)propyl]-1-piperazinyl]ethoxy]ethyl]benzenesulphonamide, difumarate;

4-methoxy-N,2,6-trimethyl-N-[2-[2-oxo-2-[4-(4-piperidinyl)-1-piperazinyl]ethoxy]ethyl]benzenesulphonamide, bis(trifluoroacetate);

4-methoxy-N,2,6-trimethyl-N-[2-[2-oxo-2-[4-(6-amino-3-pyridinyl)-1-piperazinyl]ethoxy]ethyl]benzenesulphonamide;

4-methoxy-N,2,6-trimethyl-N-[2-[2-oxo-2-[4-(6-amino-3-pyridinyl)-1-piperazinyl]ethoxy]ethyl]benzenesulphonamide, fumarate;

N-[2-[2-[4-[2-(dimethylamino)-1,1-dimethylethyl]-1-piperidinyl]-2-oxoethoxy]ethyl]-4-methoxy-N,2,6-trimethylbenzenesulphonamide, trifluoroacetate;

N-[2-[2-[4-[2-(dimethylamino)-1-hydroxyethyl]-1-piperidinyl]-2-oxoethoxy]ethyl]-4-methoxy-N,2,6-trimethylbenzenesulphonamide, trifluoroacetate;

4-methoxy-N,2,6-trimethyl-N-[2-[2-[4-(4-methyl-1-piperazinyl)-1-piperidinyl]-2-oxoethoxy]ethyl]benzenesulphonamide;

4-methoxy-N,2,6-trimethyl-N-[2-[2-[4-(4-methyl-1-piperazinyl)-1-piperidinyl]-2-oxoethoxy]ethyl]benzenesulphonamide, fumarate;

4-methoxy-N,2,6-trimethyl-N-[2-[2-[4-(1-methyl-4-piperidinyl)-1-piperidinyl]-2-oxoethoxy]ethyl]benzenesulphonamide, fumarate;

N-cyclopropyl-4-methoxy-2,6-dimethyl-N-[2-[2-[4-(4-methyl-1-piperazinyl)-1-piperidinyl]-2-oxoethoxy]ethyl]benzenesulphonamide, difumarate;

4-methoxy-N,2,6-trimethyl-N-[2-[2-[4-[2-(1-pyrrolidinyl)ethyl]-1-piperidinyl]-2-oxoethoxy]ethyl]benzenesulphonamide, fumarate;

4-methoxy-N,2,6-trimethyl-N-[2-[2-[4-[4-(1-methylethyl)-1-piperazinyl]-1-piperidinyl]-2-oxoethoxy]ethyl]benzenesulphonamide, fumarate;

N-ethyl-4-methoxy-2,6-dimethyl-N-[2-[2-[4-[2-(1-pyrrolidinyl)ethyl]-1-piperidinyl]-2-oxoethoxy]ethyl]benzenesulphonamide, fumarate;

N-cyclopropyl-4-methoxy-2,6-dimethyl-N-[2-[2-[4-[2-(1-pyrrolidinyl)ethyl]-1-piperidinyl]-2-oxoethoxy]ethyl]benzenesulphonamide, fumarate;

N-[2-[2-[4-[2-(hexahydro-4-methyl-1H-1,4-diazepin-1-yl)ethyl]-1-piperidinyl]-2-oxoethoxy]ethyl]-4-methoxy-N,2,6-trimethyl-benzenesulphonamide, difumarate;

4-methoxy-N,2,6-trimethyl-N-[2-[2-[4-[2-[methyl(1-methylethyl)amino]ethyl]-1-piperidinyl]-2-oxoethoxy]ethyl]-benzenesulphonamide, fumarate;

4-methoxy-N,2,6-trimethyl-N-[2-[2-[4-[methyl(1-methyl-4-piperidinyl)amino]-1-piperidinyl]-2-oxoethoxy]ethyl]benzenesulphonamide, fumarate;

4-methoxy-N,2,6-trimethyl-N-[2-[2-[4-[1-(1-methylethyl)-4-piperidinyl]-1-piperidinyl]-2-oxoethoxy]ethyl]benzenesulphonamide, fumarate;

4-methoxy-N,2,6-trimethyl-N-[2-[2-[4-(1-ethyl-4-piperidinyl)-1-piperidinyl]-2-oxoethoxy]ethyl]benzenesulphonamide, fumarate;

4-methoxy-N,2,6-trimethyl-N-[2-[2-[4-(1-cyclopropyl-4-piperidinyl)-1-piperidinyl]-2-oxoethoxy]ethyl]benzenesulphonamide, fumarate;

4-methoxy-N,2,6-trimethyl-N-[2-[2-[4-[2-(4-morpholinyl)ethyl]-1-piperidinyl]-2-oxoethoxy]ethyl]benzenesulphonamide, fumarate;

4-methoxy-N,2,6-trimethyl-N-[2-[2-[4-[1,1-dimethyl-2-(1-azetidinyl)ethyl]-1-piperidinyl]-2-oxoethoxy]ethyl]benzenesulphonamide, fumarate;

N-ethyl-4-methoxy-2,6-dimethyl-N-[2-[2-[4-(1-methyl-4-piperidinyl)-1-piperidinyl]-2-oxoethoxy]ethyl]benzenesulphonamide, fumarate;

N-[2-[2-[4-(hexahydro-4-methyl-1H-1,4-diazepin-1-yl)-1-piperidinyl]-2-oxoethoxy]ethyl]-4-methoxy-N,2,6-trimethyl-benzenesulphonamide, fumarate;

N-cyclopropyl-4-methoxy-2,6-dimethyl-N-[2-[2-[4-(1-methyl-4-piperidinyl)-1-piperidinyl]-2-oxoethoxy]ethyl]benzenesulphonamide, fumarate;

2,4-dichloro-N,3-dimethyl-N-[2-[2-[4-(1-methyl-4-piperidinyl)-1-piperidinyl]-2-oxoethoxy]ethyl]benzenesulphonamide, fumarate;

4-methoxy-N,2,6-trimethyl-N-[2-[2-[4-[2-(1-azetidinyl)ethyl]-1-piperidinyl]-2-oxoethoxy]ethyl]benzenesulphonamide, fumarate;

2,6-dichloro-4-methoxy-N-methyl-N-[2-[2-[4-[2-(dimethylamino)ethyl]-1-piperidinyl]-2-oxoethoxy]ethyl]-benzenesulphonamide, fumarate;

2,6-dichloro-4-methoxy-N-methyl-N-[2-[2-[4-(1-methyl-4-piperidinyl)-1-piperidinyl]-2-oxoethoxy]ethyl]benzenesulphonamide, fumarate;

4-methoxy-N,2,6-trimethyl-N-[2-[2-[4-[(1-pyrrolidinyl)methyl]-1-piperidinyl]-2-oxoethoxy]ethyl]benzenesulphonamide, fumarate;

4-methoxy-N,2,6-trimethyl-N-[2-[2-[4-[(4-ethyl-1-piperazinyl)methyl]-1-piperidinyl]-2-oxoethoxy]ethyl]benzenesulphonamide, fumarate;

N-cyclopropyl-4-methoxy-2,6-dimethyl-N-[2-[2-[4-[(4-methyl-1-piperazinyl)methyl]-1-piperidinyl]-2-oxoethoxy]ethyl]benzenesulphonamide, difumarate;

N-ethyl-4-methoxy-2,6-dimethyl-N-[2-[2-[4-[(4-methyl-1-piperazinyl)methyl]-1-piperidinyl]-2-oxoethoxy]ethyl]benzenesulphonamide, difumarate;

N-methyl-4-methoxy-2,6-dichloro-N-[2-[2-[4-[(4-methyl-1-piperazinyl)methyl]-1-piperidinyl]-2-oxoethoxy]ethyl]benzenesulphonamide, difumarate;

4-methoxy-N,2,6-trimethyl-N-[2-[2-[4-[1,1-dimethyl-2-(1-piperidinyl)ethyl]-1-piperidinyl]-2-oxoethoxy]ethyl]benzenesulphonamide, trifluoroacetate;

4-methoxy-N,2,6-trimethyl-N-[2-[2-[4-[1,1-dimethyl-2-(1-pyrrolidinyl)ethyl]-1-piperidinyl]-2-oxoethoxy]ethyl]benzenesulphonamide, fumarate;

N-[2-[2-[4-[2-(ethylmethylamino)ethyl]-1-piperidinyl]-2-oxoethoxy]ethyl]-4-methoxy-N,2,6-trimethylbenzenesulphonamide, fumarate;

N-[2-[2-[4-[2-(diethylamino)ethyl]-1-piperidinyl]-2-oxoethoxy]ethyl]-4-methoxy-N,2,6-trimethylbenzenesulphonamide, fumarate;

4-methoxy-N-(1-methylethyl)-2,6-dimethyl-N-[2-[2-[4-[2-(1-pyrrolidinyl)ethyl]-1-piperidinyl]-2-oxoethoxy]ethyl]benzenesulphonamide, fumarate;

4-methoxy-N,2,6-trimethyl-N-[2-[2-[4-[1,1-dimethyl-2-(4-morpholinyl)ethyl]-1-piperidinyl]-2-oxoethoxy]ethyl]benzenesulphonamide, fumarate;

N-[2-[2-[4-[2-(hexahydro-4-methyl-1H-1,4-diazepin-1-yl)ethyl]-1-piperidinyl]-2-oxoethoxy]ethyl]-4-methoxy-N,2,6-trimethylbenzenesulphonamide, difumarate;

N-[2-[2-[4-[(hexahydro-4-methyl-1H-1,4-diazepin-1-yl)methyl]-1-piperidinyl]-2-oxoethoxy]ethyl]-4-methoxy-N,2,6-trimethylbenzenesulphonamide, difumarate;

4-methoxy-N-[2-[2-[4-[2-(1-methyl-4-piperidinyl)ethyl]-1-piperidinyl]-2-oxoethoxy]ethyl]-N,2,6-trimethylbenzenesulphonamide, fumarate;

4-methoxy-N-[2-[2-[4-[2-(1-piperidinyl)ethyl]-1-piperidinyl]-2-oxoethoxy]ethyl]-N,2,6-trimethylbenzenesulphonamide, fumarate;

4-methoxy-N-[2-[2-[4-[2-(1-pyrrolidinyl)ethyl]-1-piperidinyl]-2-oxoethoxy]ethyl]-N-methyl-2-trifluoromethyl-benzenesulphonamide, trifluoroacetate;

4-methoxy-N-[2-[2-[4-[2-(1-methyl-4-piperazinyl)-2-oxoethyl]-1-piperidinyl]-2-oxoethoxy]ethyl]-N,2,6-trimethylbenzenesulphonamide, fumarate;

4-methoxy-N,2,6-trimethyl-N-[2-[2-[4-[1,1-dimethyl-2-(diethylamino)ethyl]-1-piperidinyl]-2-oxoethoxy]ethyl]benzenesulphonamide, trifluoroacetate;

4-methoxy-N,2,6-trimethyl-N-[2-[2-[4-(dimethylamino)methyl]-1-piperidinyl]-2-oxoethoxy]ethyl]benzenesulphonamide, fumarate;

4-methoxy-N,2,6-trimethyl-N-[2-[2-[4-[(1-azetidinyl)methyl]-1-piperidinyl]-2-oxoethoxy]ethyl]benzenesulphonamide, fumarate;

N,2,4,6-tetramethyl-N-[2-[2-[4-(1-methyl-4-piperidinyl)-1-piperidinyl]-2-oxoethoxy]ethyl]benzenesulphonamide, trifluoroacetate;

N-methyl-N-[2-[2-[4-(1-methyl-4-piperidinyl)-1-piperidinyl]-2-oxoethoxy]ethyl]-2-trifluoromethyl-benzenesulphonamide, trifluoroacetate;

4-methoxy-N-methyl-N-[2-[2-[4-(1-methyl-4-piperidinyl)-1-piperidinyl]-2-oxoethoxy]ethyl]-2-trifluoromethyl-benzenesulphonamide, trifluoroacetate;

N,2,4,6-tetramethyl-N-[2-[2-[4-[2-(1-pyrrolidinyl)ethyl]-1-piperidinyl]-2-oxoethoxy]ethyl]benzenesulphonamide, trifluoroacetate;

2,6-dichloro-4-methoxy-N-methyl-N-[2-[2-[4-(1-methyl-4-piperazinyl)-1-piperidinyl]-2-oxoethoxy]ethyl]benzenesulphonamide, difumarate;

4-methoxy-N,2,6-trimethyl-N-[2-[2-[4-[2-(dimethylamino)ethyl]-1-piperidinyl]-2-oxoethoxy]-ethyl]benzenesulphonamide, fumarate;

4-methoxy-N,2,6-trimethyl-N-[2-[2-[4-(4-cyclopropyl-1-piperazinyl)-1-piperidinyl]-2-oxoethoxy]ethyl]benzenesulphonamide, fumarate;

4-methoxy-N,2,6-trimethyl-N-[2-[2-[4-[4-(1,1-dimethylethyl)-1-piperazinyl]-1-piperidinyl]-2-oxoethoxy]ethyl]benzenesulphonamide, difumarate;
4-methoxy-N,2,6-trimethyl-N-[2-[2-[4-[(4-methyl-1-piperazinyl)methyl]-1-piperidinyl]-2-oxoethoxy]ethyl]benzenesulphonamide, difumarate;
4-methoxy-N,2,6-trimethyl-N-[2-[2-[4-[2-(4-methyl-1-piperazinyl)ethyl]-1-piperidinyl]-2-oxoethoxy]ethyl]benzenesulphonamide, difumarate;
4-methoxy-N,2,6-trimethyl-N-[2-[2-[4-[3-(4-morpholinyl)-propyl]-1-piperidinyl]-2-oxoethoxy]ethyl]benzenesulphonamide;
4-methoxy-N,2,6-trimethyl-N-[2-[2-[4-[3-(4-morpholinyl)-propyl]-1-piperidinyl]-2-oxoethoxy]ethyl]benzenesulphonamide, fumarate;
4-methoxy-N,2,6-trimethyl-N-[2-[2-[4-[3-(1-pyrrolidinyl)propyl]-1-piperidinyl]-2-oxoethoxy]ethyl]-benzenesulphonamide;
4-methoxy-N,2,6-trimethyl-N-[2-[2-[4-[3-(1-pyrrolidinyl)propyl]-1-piperidinyl]-2-oxoethoxy]ethyl]benzenesulphonamide, fumarate;
4-methoxy-N,2,6-trimethyl-N-[2-[2-[4-[3-(hexahydro-4-methyl-1H-1,4-diazepin-1-yl)propyl]-1-piperidinyl]-2-oxoethoxy]ethyl]benzenesulphonamide;
4-methoxy-N,2,6-trimethyl-N-[2-[2-[4-[3-(hexahydro-4-methyl-1H-1,4-diazepin-1-yl)propyl]-1-piperidinyl]-2-oxoethoxy]ethyl]benzenesulphonamide, difumarate;
4-methoxy-N,2,6-trimethyl-N-[2-[2-[4-[3-(4-methyl-1-piperazinyl)propyl]-1-piperidinyl]-2-oxoethoxy]ethyl]benzenesulphonamide;
4-methoxy-N,2,6-trimethyl-N-[2-[2-[4-[3-(4-methyl-1-piperazinyl)propyl]-1-piperidinyl]-2-oxoethoxy]ethyl]benzenesulphonamide, difumarate;
4-methoxy-N,2,6-trimethyl-N-[2-[2-[4-[3-(1-azetidinyl)propyl]-1-piperidinyl]-2-oxoethoxy]ethyl]benzenesulphonamide;
4-methoxy-N,2,6-trimethyl-N-[2-[2-[4-[3-(1-azetidinyl)propyl]-1-piperidinyl]-2-oxoethoxy]ethyl]benzenesulphonamide, fumarate;
4-methoxy-N,2,6-trimethyl-N-[2-[2-[4-[3-(dimethylamino)-propyl]-1-piperidinyl]-2-oxoethoxy]ethyl]benzenesulphonam ide;
4-methoxy-N,2,6-trimethyl-N-[2-[2-[4-[3-(dimethylamino)-propyl]-1-piperidinyl]-2-oxoethoxy]ethyl]-benzenesulphonamide, fumarate;
N-[2-(2-[4,4'-bipiperidin]-1-yl-2-oxoethoxy)ethyl]-4-methoxy-N,2,6-trimethylbenzenesulphonamide, trifluoroacetate;
4-methoxy-N,2,6-trimethyl-N-[2-[2-[4-[2-(methylamino)ethyl]-1-piperidinyl]-2-oxoethoxy]ethyl]benzenesulphonamide;
4-methoxy-N,2,6-trimethyl-N-[2-[2-[4-[2-(methylamino)ethyl]-1-piperidinyl]-2-oxoethoxy]ethyl]benzenesulphonamide, fumarate;
N-[2-[2-(4-amino-1-piperidinyl)-2-oxoethoxy]ethyl]-4-methoxy-N,2,6-trimethylbenzenesulphonamide;
4-methoxy-N,2,6-trimethyl-N-[2-[2-[4-[(8-methyl-8-azabicyclo[3.2.1]oct-3-yl)amino]-1-piperidinyl]-2-oxoethoxy]ethyl]benzenesulphonamide;
4-methoxy-N,2,6-trimethyl-N-[2-[2-[4-[(8-methyl-8-azabicyclo[3.2.1]oct-3-yl)amino]-1-piperidinyl]-2-oxoethoxy]-ethyl]benzenesulphonamide, bis(trifluoroacetate);
4-methoxy-N,2,6-trimethyl-N-[2-[2-[4-(methylamino)-1-piperidinyl]-2-oxoethoxy]ethyl]-benzenesulphonamide;
4-methoxy-N,2,6-trimethyl-N-[2-[2-[4-[methyl(8-methyl-8-azabicyclo[3.2.1]oct-3-yl)amino]-1-piperidinyl]-2-oxoethoxy]ethyl]benzenesulphonamide;
4-methoxy-N,2,6-trimethyl-N-[2-[2-[4-[methyl(8-methyl-8-azabicyclo[3.2.1]oct-3-yl)amino]-1-piperidinyl]-2-oxoethoxy]ethyl]benzenesulphonamide, bis(trifluoroacetate);
4-methoxy-N,2,6-trimethyl-N-[2-[2-oxo-2-[4-(1-piperazinyl-methyl)-1-piperidinyl]ethoxy]ethyl]benzenesulphonamide;
4-methoxy-N,2,6-trimethyl-N-[2-[2-oxo-2-[4-(1-piperazinyl-methyl)-1-piperidinyl]ethoxy]ethyl]benzenesulphonamide, fumarate;
4-methoxy-N,2,6-trimethyl-N-[2-[2-oxo-2-[4-[1-oxo-2-(4-methyl-1-piperazinyl)ethyl]-1-piperidinyl]ethoxy]ethyl]benzenesulphonamide, bis(trifluoroacetate);
4-methoxy-N,2,6-trimethyl-N-[2-[2-[4-(1-methyl-4-piperidinyl)]-1-piperazinyl]-2-oxoethoxy]ethyl]benzenesulphonamide;
4-methoxy-N,2,6-trimethyl-N-[2-[2-[4-(1-methyl-4-piperidinyl)]-1-piperazinyl]-2-oxoethoxy]ethyl]benzenesulphonamide, dihydrochioride; and
4-methoxy-N,2,6-trimethyl-N-[2-[2-[4-(1-methyl-4-piperidinyl)]-1-piperazinyl]-2-oxoethoxy]ethyl]benzenesulphonamide, difumarate.

8. A therapeutic composition comprising a formula I compound of claim 7 or a salt thereof and a physiologically acceptable excipient.

* * * * *

UNITED STATES PATENT AND TRADEMARK OFFICE
CERTIFICATE OF CORRECTION

PATENT NO. : 7,538,111 B2  
APPLICATION NO. : 10/549546  
DATED : May 26, 2009  
INVENTOR(S) : Barth et al.

It is certified that error appears in the above-identified patent and that said Letters Patent is hereby corrected as shown below:

Col. 45, line 14: "EXAMPIE 51" should read --EXAMPLE 51--

Col. 47, line 9: "CXXXXVI, the product sought" should read --CXXXVI, the product sought--

Cols. 71-72, Table I: "3    4-$CH_3$" should read --3    4-O-$CH_3$--

Cols. 71-72, Table I: "4    4-$CH_3$" should read --4    4-O-$CH_3$--

Cols. 71-72, Table I: "5    4-$CH_3$" should read --5    4-O-$CH_3$--

Cols. 71-72, Table I: "6    4-$CH_3$" should read --6    4-O-$CH_3$--

Cols. 71-72, Table I: "7    4-$CH_3$" should read --7    4-O-$CH_3$--

Cols. 71-72, Table I: "8    4-$CH_3$" should read --8    4-O-$CH_3$--

Cols. 75-76, Table I-continued: "37    4-O-$CH_3$    2-$CH_3$    6-$CH_3$ -$CH_3$ N 2" should read --4-O-$CH_3$    2-$CH_3$    6-$CH_3$    -$CH_3$    N    3--

Cols. 83-84, Table I-continued: "91    4-O-$CH_3$    2-$CH_3$    6-$CH_3$" should read --91    4-Cl    2-Cl    3-$CH_3$--

Cols. 85-86, Table I-continued: "99    4-O-$CH_3$    2-$CH_3$    6-$CH_3$" should read --99    4-O-$CH_3$    2-Cl    6-Cl--

Signed and Sealed this

Twenty-fourth Day of November, 2009

David J. Kappos  
*Director of the United States Patent and Trademark Office*